(12) United States Patent
Eckhardt et al.

(10) Patent No.: US 11,992,494 B2
(45) Date of Patent: May 28, 2024

(54) CYCLOPENTATHIOPHENE CARBOXAMIDE DERIVATIVES AS PLATELET ACTIVATING FACTOR RECEPTOR ANTAGONISTS

(71) Applicant: Boehringer Ingelheim International GmbH, Ingelheim am Rhein (DE)

(72) Inventors: Matthias Eckhardt, Biberach an der Riss (DE); Ferenc Kontes, Biberach an der Riss (DE); Christofer Siegfried Tautermann, Biberach an der Riss (DE); Dieter Wiedenmayer, Biberach an der Riss (DE); Marina Kristina Willwacher, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 18/083,602

(22) Filed: Dec. 19, 2022

(65) Prior Publication Data
US 2023/0190763 A1  Jun. 22, 2023

(30) Foreign Application Priority Data

Dec. 22, 2021  (EP) ..................................... 21216739

(51) Int. Cl.
*C07D 495/14* (2006.01)
*A61K 31/551* (2006.01)
*C07D 519/00* (2006.01)

(52) U.S. Cl.
CPC .......... *A61K 31/551* (2013.01); *C07D 495/14* (2013.01); *C07D 519/00* (2013.01)

(58) Field of Classification Search
CPC ............................ C07D 495/14; C07D 519/00
See application file for complete search history.

(56) References Cited

U.S. PATENT DOCUMENTS

| 5,104,543 | A  | 4/1992  | Brandt et al. |
| 5,155,103 | A  | 10/1992 | Weber et al. |
| 5,532,233 | A  | 7/1996  | Weber et al. |
| 7,015,213 | B1 | 3/2006  | Bigg et al. |
| 2005/0032713 | A1 | 2/2005 | Wurtman et al. |

FOREIGN PATENT DOCUMENTS

| CA | 1269373   | A  | 5/1990 |
| CA | 2012411   | A1 | 9/1990 |
| DE | 4132763   | A1 | 4/1993 |
| EP | 194416    | A1 | 9/1986 |
| EP | 0254245   | A1 | 1/1988 |
| EP | 368175    | A1 | 5/1990 |
| EP | 388789    | A1 | 9/1990 |
| EP | 0450504   | A1 | 10/1991 |
| EP | 480455    | A1 | 4/1992 |
| WO | 2008063667 | A1 | 5/2008 |

OTHER PUBLICATIONS

Weber, Hetrapezines as Antagonists of Platelt Activating Factor, Medicinal Research Reviews, vol. 9, 1989, p. 181-218.
Miyazawa, Structure-Activity Studies on Triazolothienodiazepine Derivatives as Platelet-Activating Factor Antagonists, Chem. Pharm. Bull. vol. 39, vol. 12, 1991, p. 3215-3220.
Summers, Platelet Activating Factor Antagonists, Current Pharmaceutical Design, vol. 1, 1995, p. 161-190.
Gallo, Acid Catalyzed Hydrolysis of Brtizolam, Deapartmento of Quimica, vol. 205, 1988, 3 pages.
Legouin, Isolation and Structural Data of the opened ring Derivative of a 1,2,4-Triaxololotieno-1,4-Diazepine, UFR Sciences Pharmacetiques et Biologiques, vol. 37, 2000, p. 127-129.
Sung, Asymmetric Synthesis and Structure-Activity Relationship of the Four Steroisomers of the Antiobiotic Amidinomycin, Arch. Pahmr. Med. Chem, vol. 329, 1996, 10 pages.
Fier, An atom—Economical Method to preapre Enantiopure Benzodiazepines with N-Carboxyhydrides, Organic Letters, vol. 19, 2017, 4 pages.
Brenna, Biocatalytic Synthesis of chiral cyclic y-oxoesters by sequential C—H hydroxylation, alcohol oxidation and alkene reduction, Green Chemistrym vol. 19, 2017, 9 pages.
Filippakopoulos, Selective inhibition of BET bromodomains, Nature, vol. 10, 2010, 7 pages.
Syeda, Scalable syntheses of the BET bromodomain inhibitor JQ1, Tetrahedron letters, 2015, 4 pages.
Yeo, Methadone is not a mechanism-based inhibitor of cytochrome P450 2D6, Br. J. Clin. Pharacol., vol. 57, 2003, 2 bages.
Yeo, Methadone is not a mechanism-based inhibitor of cytochrome P450 2D6, Br. J. Clin. Pharacol., vol. 57, 2003, 2 pages.
International Search Report and Written opinion for PCT/EP2022/086670 mailed on Jul. 6, 2023.
Database pubchem, [9-2-Chlorophenyl)-3-methyl-16-thia-2,4,5,8-tetrazatetracyclo{8.60.02,6.011 . . . , 2020.
Summers, Platelet activating Factor Antagonists, Curr. Pharm. Design, 1995, 2 pages.
Gallo, Acid Catalyzed Hydrolysis of Brotizolam, J. Heterocyclic Chem, vol. 25, 1988, 3 pages.
Legouin, Isolation and Structural Data of the Opened Ring Derivative, J. Heterocyclic Chem., vol. 37, 2000, 3 pages.
Dupre, Inverse Agonist Activity Of Selected Ligands of Platelet, J. Pharm. Ecp. Ther., vol. 299, 2001, 8 pages.

(Continued)

*Primary Examiner* — Susanna Moore
(74) *Attorney, Agent, or Firm* — David L. Kershner

(57) ABSTRACT

Cyclopentathiophene carboxamides of formula (I),

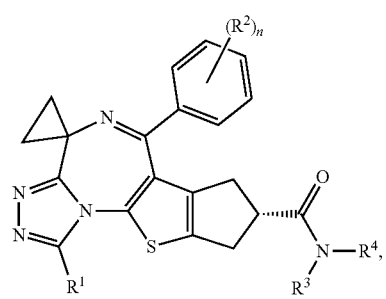

wherein $R^1$, $R^2$, $R^3$, $R^4$, and n are as defined herein, and pharmaceutically acceptable salts thereof. The compounds of formula (I) can be used in methods for the treatment of diseases which can be influenced by antagonizing the activity mediated by the platelet activating factor receptor.

13 Claims, No Drawings

(56) References Cited

OTHER PUBLICATIONS

Cellai, mechanistic Insight into WEB-2170-indiced apoptosis, vol. 37, 2009, 31 pages.
Tahara, Synthesis and Structure activity Relationships of 6-Aryl 4-H, Arzneimittel-forsching, vol. 11, 1978, 6 pages.
Sung, Asymetric Synthesis and Structure—Activity Relationship, Archiv de Pharmzie, vol. 329, 1996, 10 pages.
Abstract in English for DE4132763 cited herein dated Aug. 4, 1993.
International Search Report for PCT/EP2021/081459 mailed Dec. 23, 2021.
Wahlers, Future horizons of lung preservation by appplication of platelet activating factor antagonist compared with current clinical standards, Journal of thoracic and Cardiovascular surgery, vol. 103, 1992, p. 200-205.
De Sant'Anna, Toward a platelet activating factor pseudoreceptor 2 three dimensional semiempirical models for agonist and antagonist binding, J. of molecular structure, vol. 490, 1999, p. 167-180.
Braquet, Recent progress in ginkgolide research, Medicinal research reviews, vol. 11, 1991, p. 295-355.
Zhang, A novel platelet activating factor receptor antagonist inhibits choroidal neovascularization and subretinal fibrosis, PLOS, Vo. 8, 2013, p. 9 pages.

CYCLOPENTATHIOPHENE CARBOXAMIDE DERIVATIVES AS PLATELET ACTIVATING FACTOR RECEPTOR ANTAGONISTS

This invention relates to novel cyclopentathiophene carboxamide derivatives and pharmaceutically acceptable salts thereof, that are platelet activating factor receptor antagonists. In addition, the invention relates to pharmaceutical compositions and combinations comprising said compounds and to their use in methods for the treatment of diseases which can be influenced by antagonizing the platelet activating factor receptor. Particularly, the pharmaceutical compositions of the invention are suitable for the prophylaxis and/or therapy of ocular diseases, allergies and inflammation-related conditions and diseases, in particular dry and wet age-related macular degeneration, geographic atrophy, urticaria and NASH.

BACKGROUND OF THE INVENTION

Platelet activating factor (PAF) is an ether-phospholipid and the most potent lipid mediator known. PAF is synthesized constitutively or under specific stimuli by a variety of cells like platelets, macrophages, monocytes, neutrophils, basophils, eosinophils, mast cells and endothelial cells. PAF, PAF-like lipids (PAFLL) and some oxidized phospholipids are structurally defined ligands of the PAF receptor (PAFR), a G protein-coupled receptor. The PAFR has restricted expression on specific target cells of the immune, haemostatic and inflammatory systems. Signalling functions of PAF are mostly associated with acute and chronic inflammation in essentially all organs.

PAF is thought to play a role in a number of inflammatory disorders and may have numerous implications in ocular diseases, cardiovascular diseases, cancer, neurological and neurodegenerative disorders, renal disorders, liver diseases and allergies. The suppression of PAFR activation, e.g., via PAFR antagonists, is thus considered to be useful in the treatment of a wide range of disorders which can be influenced by antagonizing PAFR, e.g., as mentioned hereinbefore and hereinafter; in particular, PAFR antagonists should be useful for the prevention or treatment of ocular diseases, e.g., dry or wet age-related macular degeneration and geographic atrophy, or allergies and inflammation-related disorders, e.g., urticaria and non-alcoholic steatohepatitis (NASH).

PAFR antagonists suitable for therapeutic use should bind potently and with high selectivity to PAFR. They should be well absorbed from the gastrointestinal tract, be sufficiently metabolically stable and possess favorable pharmacokinetic properties. They should be non-toxic and demonstrate no or few side-effects.

Low molecular weight PAFR antagonists are known in the art, for example, the compounds described in EP0194416A1, EP0254245A1, EP0368175A1, and EP0480455A1, by Weber et al. (Med. Res. Rev. 1989, 9, 181-218), Miyazawa et al. (Chem. Pharm. Bull. 1991, 39, 3215-3220), and Summers et al. (Curr. Pharm. Des. 1995, 1, 161-190). Compounds of the thienotriazolodiazepine class as disclosed therein have been reported to undergo hydrolytic degradation in acidic solution (e.g., Gallo et al., J. Heterocyclic Chem. 1988, 25, 867-869; Legouin et al., J. Heterocyclic Chem. 2000, 37, 127-129).

Further methods useful for the synthesis and characterization of said and related compounds are disclosed in EP0388789A1, Sung et al. (Archiv der Pharmazie 1996, 329, 291-300), Fier et al. (Org. Lett. 2017, 19, 1454-1457), Brenna et al. (Green Chem. 2017, 19, 5122-5130), Filippakopoulos et al. (Nature 2010, 468, 1067-1073), Syeda at al. (Tetrahedron Lett. 2015, 56, 3454-3457), and Yeo et al. (Br. J. Clin. Pharmacol. 2004, 57, 687-688).

SUMMARY OF THE INVENTION

In a first aspect, the present invention relates to a compound of formula (I)

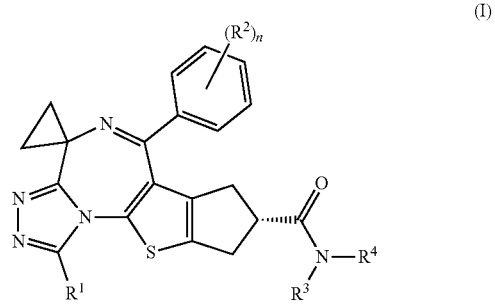

wherein
$R^1$ is selected from the group $R^1$-G1 consisting of $C_{1-4}$-alkyl optionally substituted with 1 to 3 F and $C_{3-4}$-cycloalkyl;
n is selected from the group n-G1 consisting of 0, 1, 2, and 3;
$R^2$ is independently selected from the group $R^2$-G1 consisting of F, Cl, Br, I, $C_{1-4}$-alkyl optionally substituted with 1 to 3 F or optionally substituted with 1 —CN, with 1 OH, or with 1 O—$C_{1-4}$-alkyl, further consisting of $C_{3-4}$-cycloalkyl, —CN, —CONH$_2$, —CONH($C_{1-4}$-alkyl), —CON($C_{1-4}$-alkyl)$_2$, —COOH, —COO—$C_{1-4}$-alkyl, NH$_2$, OH, —O—$C_{1-4}$-alkyl optionally substituted with 1 to 3 F, and consisting of —S(O)$_r$$C_{1-4}$-alkyl with r=0, 1, or 2;
$R^3$ is selected from the group $R^3$-G1 consisting of H and $C_{1-4}$-alkyl optionally substituted with 1 to 5 F; and
$R^4$ is selected from the group $R^4$-G1a consisting of $C_{1-6}$-alkyl
optionally substituted with 1 to 3 F and optionally substituted with 1 to 2 substituents independently selected from —CN, —CONH$_2$, —CONH($C_{1-4}$-alkyl), —CON($C_{1-4}$-alkyl)$_2$, —COOH, —COO—$C_{1-4}$-alkyl, $C_{1-3}$-alkyl-CO—NH—, $C_{1-3}$-alkyl-S(=O)$_2$—NH—, OH, and —O—$C_{1-3}$-alkyl optionally substituted with 1 to 3 F;
or
$R^4$ is selected from the group $R^4$-G1b consisting of —$C_{0-3}$-alkylene-$C_{3-10}$-cycloalkyl and —$C_{0-3}$-alkylene-$C_{3-10}$-heterocyclyl
wherein said alkylene is optionally substituted with 1 to 2 substituents selected from F and CH$_3$,
wherein 1 >CH$_2$ group of said alkylene is optionally replaced by a

moiety,
wherein said cycloalkyl and heterocyclyl are saturated mono- or bicyclic ring systems, wherein said heterocyclyl contains 1 to 2 ring members independently selected from N, NH, >N(C$_{1-4}$-alkyl), >NCO(C$_{1-4}$-alkyl), >NCOO(C$_{1-4}$-alkyl), >NS(=O)$_2$(C$_{1-4}$-alkyl), >N-phenyl, >N-pyridinyl, >N-pyrimidinyl, and O, and optionally 1 ring member selected from >C=O, >S(=O)$_r$, with r=0, 1, or 2, provided that said heterocyclyl does not contain any heteroatom-heteroatom bonds other than N—N, N—O, and N—S(=O)$_{r=1,2}$ between ring members, and wherein said cycloalkyl and heterocyclyl are optionally substituted with 1 to 2 F and optionally substituted with 1 to 2 substituents independently selected from Cl, —CN, —CONH$_2$, —CONH(C$_{1-4}$-alkyl), —CON(C$_{1-4}$-alkyl)$_2$, —OOOH, —COO—C$_{1-4}$-alkyl, OH, —O—C$_{1-3}$-alkyl optionally substituted with 1 to 3 F, from >S(=O)$_2$—C$_{1-4}$-alkyl and C$_{1-4}$-alkyl optionally substituted with 1 to 3 F or with 1 substituent selected from —CN, OH, —O—C$_{1-4}$-alkyl;

or

R$^4$ is selected from the group R$^4$-G1c consisting of —C$_{0-3}$-alkylene-phenyl and —C$_{0-3}$-alkylene-heteroaryl wherein said alkylene is optionally substituted with 1 to 2 substituents selected from F and CH$_3$, wherein 1 >CH$_2$ group of said alkylene is optionally replaced by a

moiety or by a

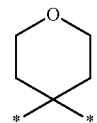

moiety or wherein 1 —CH$_2$—CH$_2$— group of said alkylene is optionally replaced by a

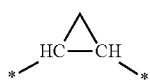

moiety or by a

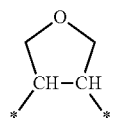

moiety, wherein said heteroaryl is a 5-membered monocycle containing 1 ring member selected from N, NH, O, and S and optionally further containing 1 to 2 ring members N, or a 6-membered monocycle containing 1 to 2 ring members N, and wherein said phenyl and heteroaryl are optionally substituted with 1 to 3 substituents independently selected from F, C, Br, C$_{3-4}$-cycloalkyl, —CN, —CONH$_2$, —CONH(C$_{1-4}$-alkyl), —CON(C$_{1-4}$-alkyl)$_2$, —OOOH, —COO—C$_{1-4}$-alkyl, —NHCO—C$_{1-4}$-alkyl, —NHS(=O)$_2$—C$_{1-4}$-alkyl, —S(=O)$_r$—C$_{1-4}$-alkyl with r=0, 1, or 2, from —O—C$_{1-4}$-alkyl optionally substituted with 1 to 3 F, and from C$_{1-4}$-alkyl optionally substituted with 1 to 3 F or with 1 substituent selected from —CN, OH, and —O—C$_{1-4}$-alkyl;

or

R$^4$ is selected from the group R$^4$-G1d consisting of 7- to 12-membered fused bicyclic aryl, heteroaryl, or heterocyclyl wherein said bicyclic aryl, heteroaryl, or heterocyclyl consists of one non-aromatic ring that is attached to the amide N atom in formula (I) and optionally contains 1 to 2 ring members independently selected from >N—, >NH, >N(C$_{1-4}$-alkyl), >N(CO—C$_{1-3}$-alkyl), >N(S(=O)$_2$—C$_{1-3}$-alkyl), and O, and optionally contains 1 ring member selected from C=O and S(=O)$_r$, with r=0, 1, or 2, and of one aromatic ring selected from phenyl, pyrrole, furan, and thiophene in each of which 1 to 2 CH ring members are optionally replaced with N, wherein said bicyclic aryl, heteroaryl, or heterocyclyl is optionally substituted with 1 to 4 F, is optionally substituted with 1 to 4 C$_{1-3}$-alkyl optionally substituted with 1 to 4 F, and is optionally substituted with 1 to 2 substituents selected from the group consisting of Cl, —CN, —CONH$_2$, —CONH(C$_{1-4}$-alkyl), —CON(C$_{1-4}$-alkyl)$_2$, —OOOH, —COO—C$_{1-4}$-alkyl, HO—C$_{1-3}$-alkylene-, C$_{1-3}$-alkyl-O—C$_{1-3}$-alkylene-, NH$_2$, C$_{1-3}$-alkyl-CO—NH—, C$_{1-3}$-alkyl-S(=O)$_2$—NH—, OH, and C$_{1-3}$-alkyl-O— optionally substituted with 1 to 3 F;

or

R$^3$ and R$^4$ are selected from the group R$^{3/4}$-G1a in which R$^3$ and R$^4$, together with the amide N atom they are attached to, form a saturated 3- to 8-membered monocyclic heterocyclyl optionally further containing 1 to 2 ring members independently selected from >NH, >N(C$_{1-4}$-alkyl), >N(CO—C$_{1-3}$-alkyl), >N(S(=O)$_2$—C$_{1-3}$-alkyl), and O, and optionally containing 1 ring member selected from >C=O and >S(=O)$_r$, with r=0, 1, or 2, provided that said heterocyclyl does not contain any heteroatom-heteroatom bonds other than N—N, N—O, and N—S(=O)$_{r=1,2}$ between ring members, wherein said heterocyclyl is optionally substituted with 1 to 4 F, is optionally substituted with 1 to 4 C$_{1-3}$-alkyl optionally substituted with 1 to 3 F, and is optionally substituted with 1 to 2 substituents selected from C, —CN, —CONH$_2$, —CONH(C$_{1-4}$-alkyl), —CON(C$_{1-4}$-alkyl)$_2$, —OOOH, —COO—C$_{1-4}$-alkyl, HO—C$_{1-3}$-alkylene-, C$_{1-3}$-alkyl-O—C$_{1-3}$-alkylene-, C$_{1-3}$-alkyl-CO—NH—, C$_{1-3}$-alkyl-S(=O)$_2$—NH—, OH, and C$_{1-3}$-alkyl-O— optionally substituted with 1 to 3 F;

or

R³ and R⁴ are selected from the group R$^{3/4}$-G1b in which R³ and R⁴, together with the amide N atom they are attached to, form a saturated 5- to 12-membered bicyclic heterocyclyl
  optionally further containing 1 to 3 ring members independently selected from >N—, >NH, >N($C_{1-4}$-alkyl), >N(CO—$C_{1-3}$-alkyl), >N(S(=O)$_2$—$C_{1-3}$-alkyl), and O, and
  optionally containing 1 ring member selected from >C=O and >S(=O)$_r$, with r=0, 1, or 2,
  provided that said heterocyclyl does not contain any heteroatom-heteroatom bonds other than N—N, N—O, and N—S(=O)$_{r=1,2}$ between ring members
    wherein said heterocyclyl is optionally substituted with 1 to 6 F,
    is optionally substituted with 1 to 4 $C_{1-3}$-alkyl optionally substituted with 1 to 3 F, and
    is optionally substituted with 1 to 2 substituents selected from Cl, —CN, —CONH$_2$, —CONH($C_{1-4}$-alkyl), —CON($C_{1-4}$-alkyl)$_2$, —COOH, —COO—$C_{1-4}$-alkyl, HO—$C_{1-3}$-alkylene-, $C_{1-3}$-alkyl-O—$C_{1-3}$-alkylene-, $C_{1-3}$-alkyl-CO—NH—, $C_{1-3}$-alkyl-S(=O)$_2$—NH—, OH, and $C_{1-3}$-alkyl-O—;

wherein in any definition mentioned hereinbefore and if not specified otherwise, any alkyl or alkylene group may be straight-chained or branched, the isomers, stereoisomers, tautomers, metabolites, prodrugs, solvates, hydrates, cocrystals, and the salts thereof, particularly the pharmaceutically acceptable salts thereof, or the combinations thereof.

In a second aspect, the present invention relates to a pharmaceutical composition comprising one or more compounds of formula (I), as defined hereinbefore or hereinafter, or pharmaceutically acceptable salts thereof, optionally together with one or more inert carriers and/or diluents.

In a third aspect, the present invention relates to a pharmaceutical composition comprising one or more compounds of formula (I), as defined hereinbefore or hereinafter, or pharmaceutically acceptable salts thereof, and one or more additional therapeutic agents, optionally together with one or more inert carriers and/or diluents.

In a fourth aspect, the present invention relates to a compound of formula (I), as defined hereinbefore or hereinafter, or a pharmaceutically acceptable salt thereof for use as a medicament.

In a fifth aspect, the present invention relates to a method for the treatment of diseases or conditions which can be influenced by antagonizing the platelet activating factor receptor in a patient in need thereof, the method comprising administering to the patient one or more compounds of formula (I), as defined hereinbefore or hereinafter, or pharmaceutically acceptable salts thereof.

In addition, the present invention relates to the use of one or more compounds of formula (I), as defined hereinbefore or hereinafter, or pharmaceutically acceptable salts thereof in the manufacture of a medicament for the treatment of diseases or conditions which can be influenced by antagonizing the platelet activating factor receptor.

Furthermore, the present invention relates to a compound of formula (I), as defined hereinbefore or hereinafter, or a pharmaceutically acceptable salt thereof for use in a method for the treatment of diseases or conditions which can be influenced by antagonizing the platelet activating factor receptor, in a patient in need thereof.

Further aspects of the present invention will become apparent to the person skilled in the art directly from the foregoing and following description and the examples.

General Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of formula (I) according to the present invention including their tautomers, stereoisomers and mixtures thereof and the salts thereof, in particular the pharmaceutically acceptable salts thereof, and the solvates, hydrates and cocrystals of such compounds, including the solvates, hydrates and cocrystals of such tautomers, stereoisomers, and salts thereof.

Also, unless specifically indicated, throughout the specification and the appended claims, a given chemical formula or name shall encompass tautomers and all stereo, optical, and geometrical isomers (e.g., enantiomers, diastereomers, E/Z isomers, etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof, and solvates thereof, such as for instance hydrates, including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid, and tartaric acid.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent such as ether, EtOAc, EtOH, isopropanol, or MeCN, or a mixture thereof.

Salts of other acids than those mentioned above which for example are useful for purifying or isolating the compounds of the present invention (e.g., trifluoro acetate salts) also comprise a part of the invention.

In case a compound of the present invention is depicted in the form of a chemical name and as a formula, in case of any discrepancy the formula shall prevail.

In the groups, radicals, or moieties defined below, the number of carbon atoms is often specified preceding the group, for example, $C_{1-6}$-alkyl means an alkyl group or radical having 1 to 6 carbon atoms.

An asterisk may be used in sub-formulas to indicate the bond which is connected to the core molecule as defined. E.g., in the case of more than one attachment point, i.e., more than one asterisk, in a sub-formula, the asterisks may be further specified by a bracketed designation of the connected part of the core molecule.

The numeration of the atoms of a substituent starts with the atom which is closest to the core or to the group to which the substituent is attached.

For example, the term "3-carboxypropyl-group" represents the following substituent:

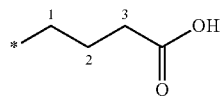

wherein the carboxy group is attached to the third carbon atom of the propyl group. The terms "1-methylpropyl-", "2,2-dimethylpropyl-" or "cyclopropylmethyl-" group represent the following groups:

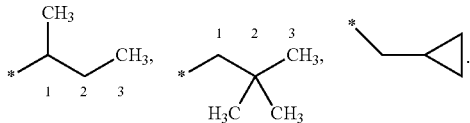

The term "substituted" as used herein, means that one or more hydrogens on the designated atom are replaced by a chemical group selected from a defined group of substituents, provided that the designated atom's normal valence is not exceeded, and that the substitution results in an acceptably stable compound. Likewise, the term "substituted" may be used in connection with a chemical moiety instead of a single atom, e.g., "substituted alkyl", "substituted aryl" or the like.

In a definition of a group, the term "wherein each X, Y, and Z group is optionally substituted with" and the like denotes that each group X, each group Y, and each group Z either each as a separate group or each as part of a composed group may be substituted as defined. For example a definition "$R^{ex}$ denotes H, $C_{1-3}$-alkyl, $C_{3-6}$-cycloalkyl, $C_{1-3}$-alkyl-$C_{3-6}$-cycloalkylene-, or $C_{1-3}$-alkyl-O—, wherein each alkyl group is optionally substituted with one or more $L^{ex}$." or the like means that in each of the before mentioned groups which comprise the term alkyl, i.e., in each of the groups $C_{1-3}$-alkyl, $C_{1-3}$-alkyl-$C_{3-6}$-cycloalkylene-, and $C_{1-3}$-alkyl-O—, the alkyl moiety may be substituted with $L^{ex}$ as defined.

The term "$C_{1-n}$-alkyl", wherein n is an integer greater than 1, either alone or in combination with another radical, denotes an acyclic, saturated, linear or branched hydrocarbon radical with 1 to n carbon atoms. For example the term $C_{1-5}$-alkyl includes $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$—, and $H_3C$—$CH_2$—$CH(CH_2CH_3)$—.

The term "$C_{3-n}$-alkylene" wherein n is an integer greater than 1, either alone or in combination with another radical, denotes an acyclic, saturated, linear or branched divalent alkyl radical with 1 to n carbon atoms. For example the term $C_{1-4}$-alkylene includes —$CH_2$—, —$CH_2$—$CH_2$—, —$CH(CH_3)$—, —$CH_2$—$CH_2$—$CH_2$—, —$C(CH_3)_2$—, —$CH(CH_2CH_3)$—, —$CH(CH_3)$—$CH_2$—, —$CH_2$—$CH(CH_3)$—, —$CH_2$—$CH_2$—$CH_2$—$CH_2$—, —$CH_2$—$CH_2$—$CH(CH_3)$—, —$CH(CH_3)$—$CH_2$—$CH_2$—, —$CH_2$—$CH(CH_3)$—$CH_2$—, —$CH(CH_3)$—$CH_2$—, —$CH_2$—$C(CH_3)_2$—, —$C(CH_3)_2$—$CH_2$—, —$CH(CH_3)$—$CH(CH_3)$—, —$CH_2$—$CH(CH_2CH_3)$—, —$CH(CH_2CH_3)$—$CH_2$—, —$CH(CH_2CH_2CH_3)$—, —$CH(CH(CH_3))_2$—, and —$C(CH_3)(CH_2CH_3)$—.

The term "$C_{3-n}$-cycloalkyl", wherein n is an integer greater than 3, either alone or in combination with another radical, denotes a cyclic, saturated, unbranched hydrocarbon radical with 3 to n carbon atoms. The cyclic group may be mono-, bi-, tri-, or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1.]octyl, spiro[4.5]decyl, norpinyl, norbonyl, norcaryl, adamantyl, etc.

The term "heterocyclyl" means a saturated or unsaturated mono- or polycyclic ring system, which optionally comprises aromatic rings, that contains one or more heteroatoms selected from N, O, or $S(O)_r$, wherein r=0, 1, or 2, consisting of 3 to 14 ring atoms wherein none of the heteroatoms is part of an aromatic ring. The term "heterocyclyl" is intended to include all the possible isomeric forms.

Thus, the term "heterocyclyl" includes the following exemplary structures; they are not depicted as radicals as each form is optionally attached through a covalent bond to any atom so long as appropriate valences are maintained:

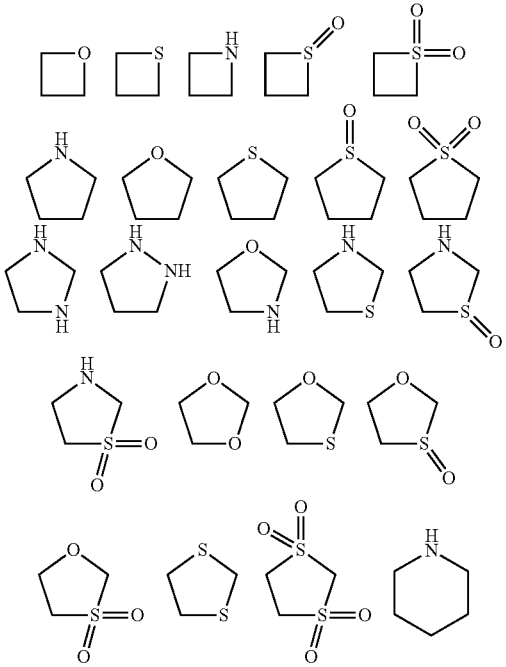

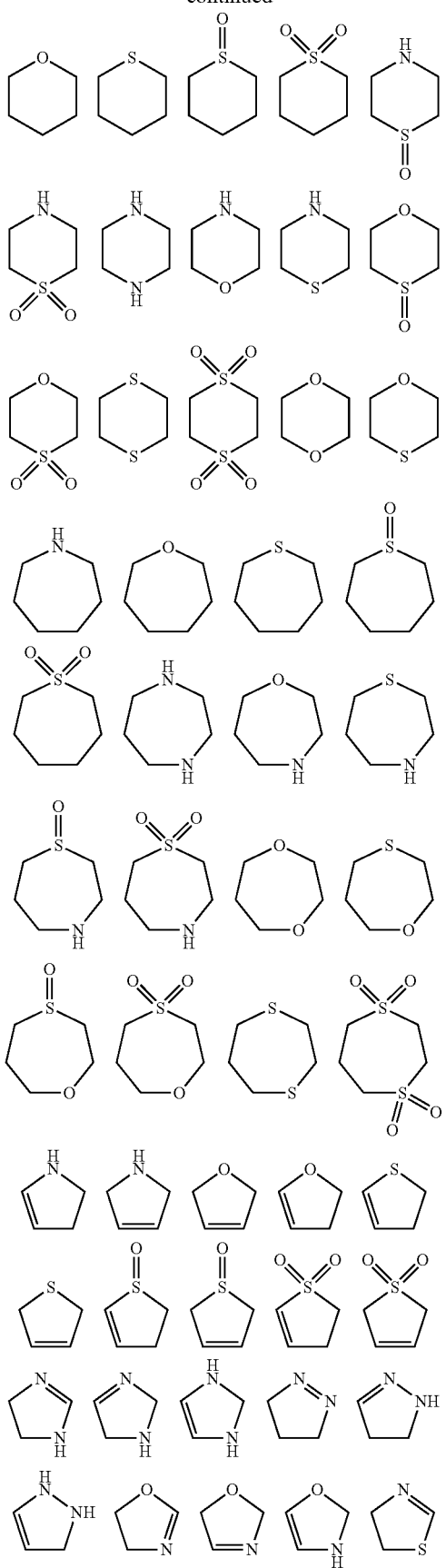
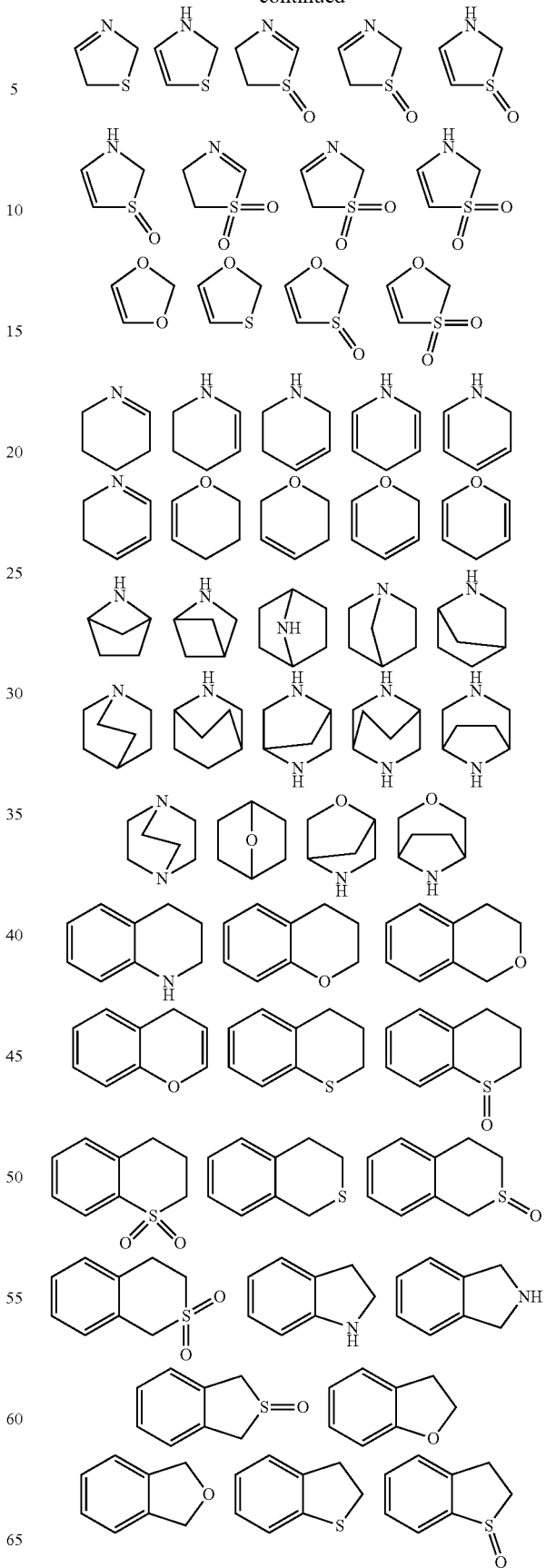

-continued

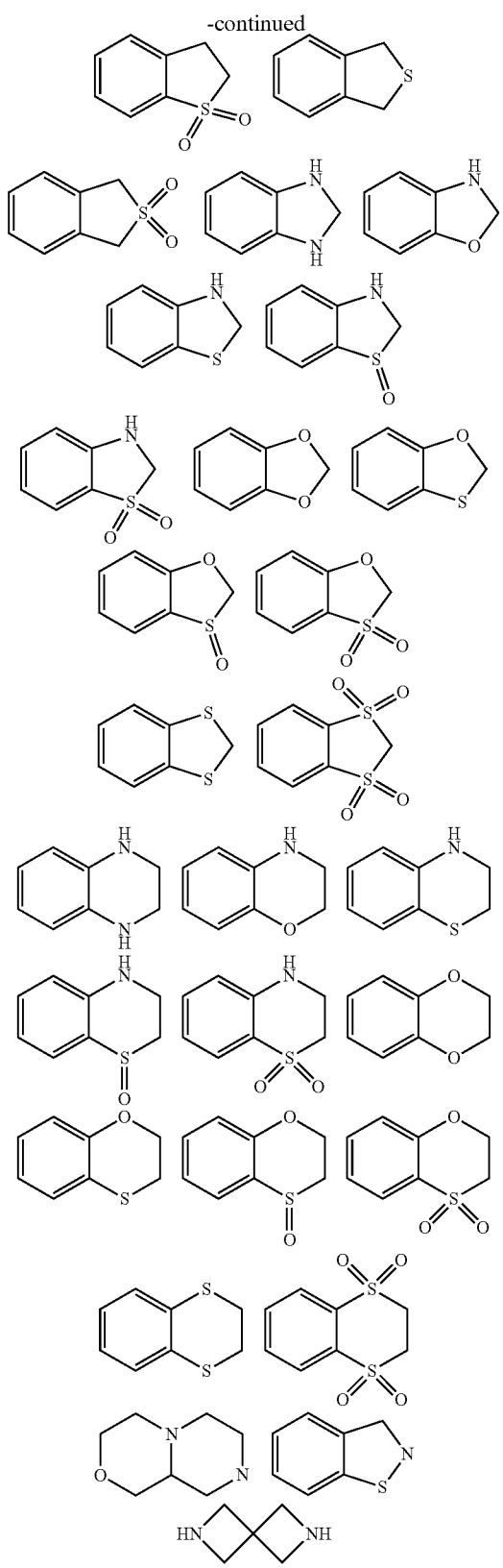

The term "aryl" as used herein, either alone or in combination with another radical, denotes a carbocyclic aromatic monocyclic group containing 6 carbon atoms which is optionally further fused to a second five- or six-membered, carbocyclic group which is aromatic, saturated or unsaturated. Aryl includes, but is not limited to, phenyl, indanyl, indenyl, naphthyl, anthracenyl, phenanthrenyl, tetrahydronaphthyl and, dihydronaphthyl.

The term "heteroaryl" means a mono- or polycyclic ring system, comprising at least one aromatic ring, containing one or more heteroatoms selected from N, O, or $S(O)_r$, wherein r=0, 1, or 2, consisting of 5 to 14 ring atoms wherein at least one of the heteroatoms is part of an aromatic ring. The term "heteroaryl" is intended to include all the possible isomeric forms.

Thus, the term "heteroaryl" includes the following exemplary structures; they are not depicted as radicals as each form is optionally attached through a covalent bond to any atom so long as appropriate valences are maintained:

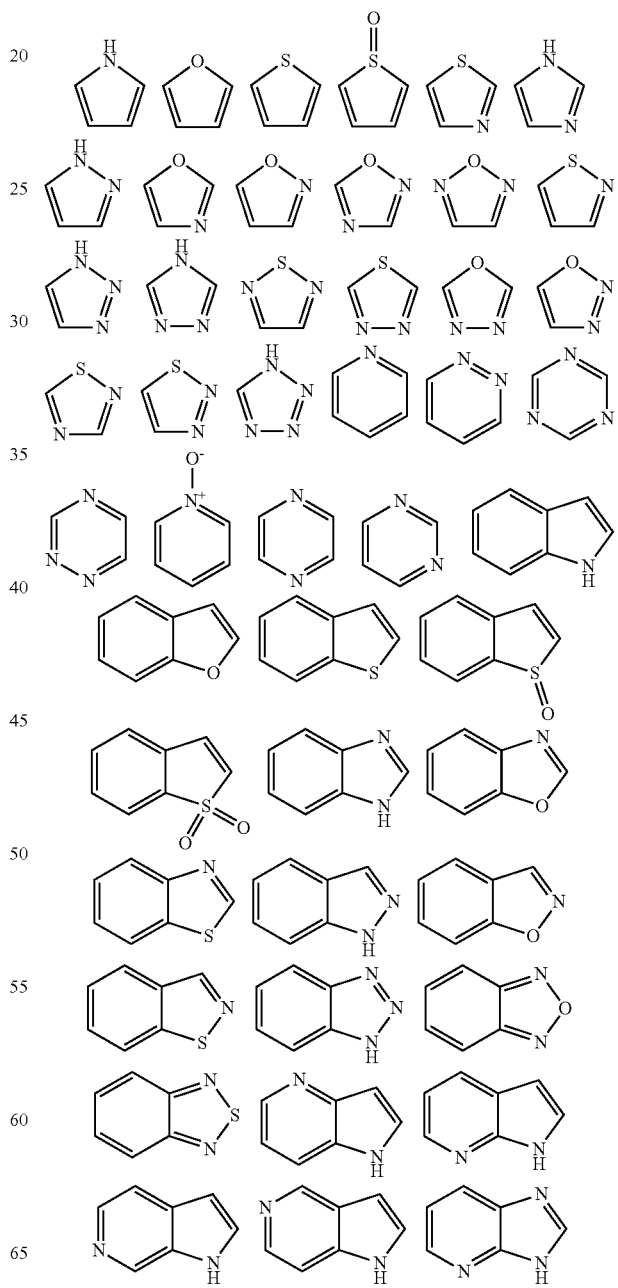

-continued

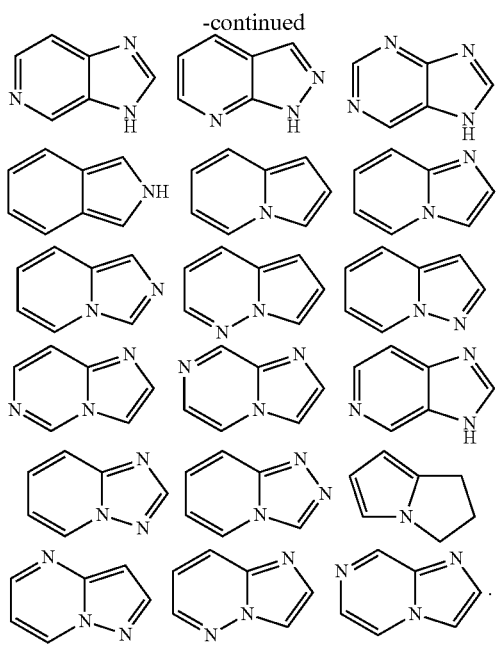

The term "bicyclic ring systems" means groups consisting of 2 joined cyclic substructures including spirocyclic, fused, and bridged ring systems.

Many of the terms given above may be used repeatedly in the definition of a formula or group and in each case have one of the meanings given above, independently of one another.

The terms "treatment" and "treating" as used herein encompass both therapeutic, i.e., curative and/or palliative, and preventative, i.e., prophylactic, treatment.

Therapeutic treatment refers to the treatment of patients having already developed one or more of said conditions in manifest, acute, or chronic form. Therapeutic treatment may be symptomatic treatment in order to relieve the symptoms of the specific indication or causal treatment in order to reverse or partially reverse the conditions of the indication or to stop or slow down progression of the disease.

Preventative treatment ("prevention") refers to the treatment of patients at risk of developing one or more of said conditions, prior to the clinical onset of the disease in order to reduce said risk.

The terms "treatment" and "treating" include the administration of one or more active compounds in order to prevent or delay the onset of the symptoms or complications and to prevent or delay the development of the disease, condition or disorder and/or in order to eliminate or control the disease, condition, or disorder as well as to alleviate the symptoms or complications associated with the disease, condition, or disorder.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

DETAILED DESCRIPTION OF THE INVENTION

The present invention discloses novel cyclopentathiophene carboxamide derivatives, which are effective platelet activating receptor (PAFR) antagonists and possess suitable pharmacological and pharmacokinetic properties to use them as medicaments for the prevention or treatment of diseases and/or conditions that may be influenced by PAFR antagonism, including but not limited to ocular diseases and inflammation-related conditions and diseases, in particular geographic atrophy, wet age-related macular degeneration, allergies, and NASH.

The compounds of the present invention may provide several advantages, such as enhanced potency, high metabolic and/or chemical stability, high selectivity, safety and tolerability, enhanced solubility, enhanced permeability, desirable plasma protein binding, enhanced bioavailability, and improved pharmacokinetic profiles.

Compounds of the Invention

In a first aspect of the present invention, it is found that compounds of formula (I)

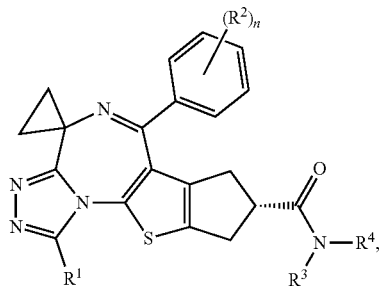

(I)

wherein $R^1$, $R^2$, $R^3$, $R^4$, and n are defined as hereinbefore and hereinafter, are potent antagonists of PAFR and may exhibit favorable properties with regard to selectivity, safety and tolerability, metabolic and/or chemical stability, pharmacokinetic and physicochemical characteristics, solubility, permeability, plasma protein binding, and bioavailability. In particular, they provide surprisingly high in vitro potencies as PAFR antagonists and show good in vivo efficacies in an animal model of choroidal neovascularization. In addition, the compounds according to the invention display advantageous chemical stabilities, particularly at low pH values. They exhibit a favorably low cytotoxicity as well as a balanced metabolism, i.e., their metabolism is not mediated predominantly by one single cytochrome P450 (CYP) enzyme like CYP3A4, and thus bear a low risk of relevant drug-drug interactions; at the same time, their renal clearances remain adequately low.

Therefore, the compounds of formula (I), as defined hereinbefore or hereinafter, or pharmaceutically acceptable salts thereof, are expected to be useful in the treatment of diseases and/or conditions that can be influenced by PAFR antagonism.

Surprisingly, it could also be shown that the compounds of formula (I) extensively bind to melanin, which impacts their biodistribution and pharmacokinetic properties; in particular, this results in their accumulation and in a prolonged drug retention in the eye. Therefore, the compounds of the invention may be particularly suitable for the treatment of ocular diseases.

Thus, according to one aspect of the present invention, a compound of formula (I)

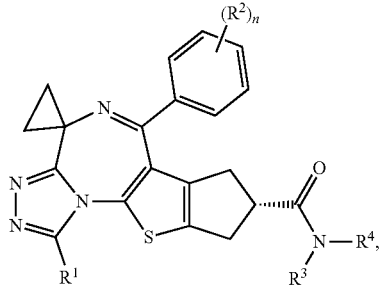

wherein $R^1$, $R^2$, $R^3$, $R^4$, and n are defined as hereinbefore and hereinafter, is provided as well as the isomers, stereoisomers, tautomers, metabolites, prodrugs, solvates, hydrates, cocrystals, and the salts thereof, particularly the pharmaceutically acceptable salts thereof.

Unless otherwise stated, the groups, residues, and substituents, particularly $R^1$, $R^2$, $R^3$, $R^4$, and n are defined as hereinbefore and hereinafter. Some preferred meanings of the substituents $R^1$, $R^2$, $R^3$, $R^4$, and n as well as of the phenyl substitution pattern of the compounds of formula (I) will be given hereinafter as embodiments of the invention. Any and each of these definitions and embodiments may be combined with one another.

$R^1$:

According to one embodiment, $R^1$ is selected from the group $R^1$-G1 consisting of
$C_{1-4}$-alkyl optionally substituted with 1 to 3 F and $C_{3-4}$-cycloalkyl.

According to another embodiment, $R^1$ is selected from the group $R^1$-G2 consisting of
$CH_3$, $CH_2CH_3$, $CH_2CH_2CH_3$, $CHF_2$, $CF_3$, and cyclopropyl.

According to another embodiment, $R^1$ is selected from the group $R^1$-G3 consisting of
$CH_3$ and $CH_2CH_3$.

According to another embodiment, $R^1$ is selected from the group $R^1$-G4 consisting of $CH_3$.

According to another embodiment, $R^1$ is selected from the group $R^1$-G5 selected from $CH_2CH_3$.

n:

According to one embodiment, n is selected from the group n-G1 consisting of 0, 1, 2, and 3.

According to another embodiment, n is selected from the group n-G2 consisting of 0, 1, and 2.

According to another embodiment, n is the group n-G3 consisting of 0.

According to another embodiment, n is the group n-G4 consisting of 1.

According to another embodiment, n is the group n-G5 consisting of 2.

$R^2$:

In cases where more than one substituent $R^2$ is present in a compound of formula (I), i.e., n=2 or 3, each $R^2$ is selected independently of one another from the embodiments and groups $R^2$-G1 to $R^2$-G6 defined hereinafter.

According to one embodiment, $R^2$ is independently selected from the group $R^2$-G1 consisting of
F, Cl, Br, I, $C_{1-4}$-alkyl optionally substituted with 1 to 3 F or optionally substituted with 1 —CN, with 1 OH, or with 1 O—$C_{1-4}$-alkyl, further consisting of $C_{3-4}$-cycloalkyl, —CN, —$CONH_2$, —$CONH(C_{1-4}$-alkyl), —$CON(C_{1-4}$-alkyl)$_2$, —OOOH, —COO—$C_{1-4}$-alkyl, $NH_2$, OH, —O—$C_{1-4}$-alkyl optionally substituted with 1 to 3 F, and consisting of —S(O)$_r C_{1-4}$-alkyl with r=0, 1, or 2.

According to another embodiment, $R^2$ is independently selected from the group $R^2$-G2 consisting of
F, Cl, Br, $C_{1-3}$-alkyl optionally substituted with 2 or 3 F, further consisting of cyclopropyl, —CN, —$C_{1-3}$-alkylene-OH, —$C_{1-2}$-alkylene-O—$C_{1-2}$-alkyl, $NH_2$, OH, —O—$C_{1-3}$-alkyl optionally substituted with 2 or 3 F, and consisting of —S—$C_{1-3}$-alkyl.

According to another embodiment, $R^2$ is independently selected from the group $R^2$-G3 consisting of
Cl, Br, $CH_3$, —CN, $NH_2$, OH, and $OCH_3$.

According to another embodiment, $R^2$ is independently selected from the group $R^2$-G4 consisting of Cl, Br, and —CN, preferably Cl.

According to another embodiment, $R^2$ is independently selected from the group $R^2$-G5 consisting of $CH_3$ and $OCH_3$.

According to another embodiment, $R^2$ is independently selected from the group $R^2$-G6 consisting of $NH_2$ and OH.

Phenyl Substitution Pattern:

For describing the substitution pattern of the phenyl ring shown in formula (I), the following carbon atom numbering is used:

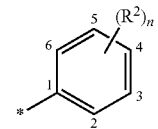

In general, the n substituents $R^2$ may be attached to any of the carbon atoms C-2 to C-6 and to any combinations thereof, respectively.

In case n=1, according to one embodiment, $R^2$ is attached to carbon atom 2.

In case n=2, according to one embodiment, one $R^2$ is attached to carbon atom 2 and the other $R^2$ is attached to carbon atom 5.

$R^2$, n and Phenyl Substitution Pattern:

According to one embodiment, $R^2$, n, and the phenyl substitution pattern are selected such that the resulting substituted phenyl ring shown in formula (I) is selected from the group Ph-G1 consisting of

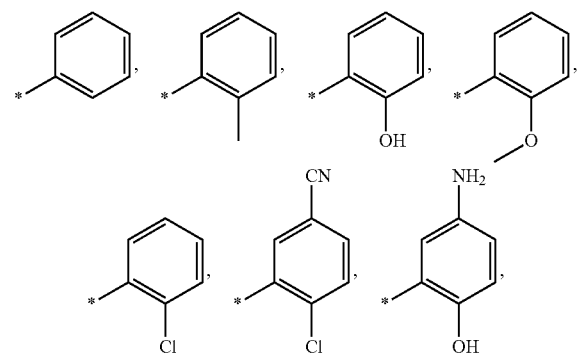

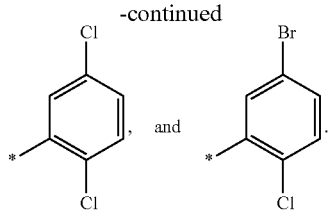, and

According to another embodiment, $R^2$, n, and the phenyl substitution pattern are selected such that the resulting substituted phenyl ring shown in formula (I) is selected from the group Ph-G2 consisting of

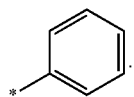

According to another embodiment, $R^2$, n and the phenyl substitution pattern are selected such that the resulting substituted phenyl ring shown in formula (I) is selected from the group Ph-G3 consisting of

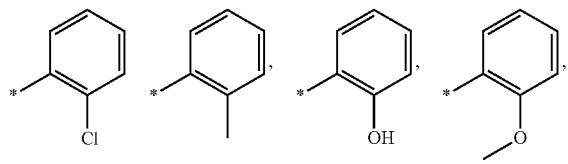

preferably

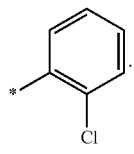

According to another embodiment, $R^2$, n, and the phenyl substitution pattern are selected such that the resulting substituted phenyl ring shown in formula (I) is selected from the group Ph-G4 consisting of

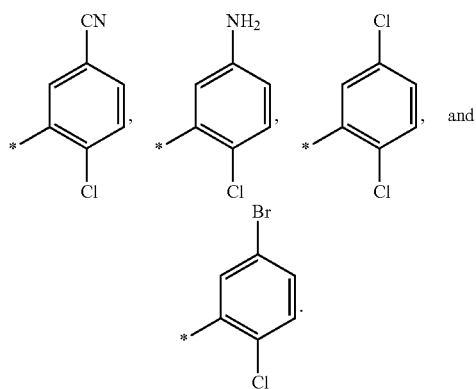

According to another embodiment, $R^2$, n, and the phenyl substitution pattern are selected such that the resulting substituted phenyl ring shown in formula (I) is selected from the group Ph-G5 consisting of

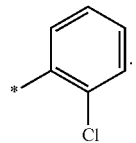

$R^3$ and $R^4$:

According to one embodiment, $R^3$ is selected from the group $R^3$-G1 consisting of H and $C_{1-4}$-alkyl optionally substituted with 1 to 5 F.

According to another embodiment, $R^3$ is selected from the group $R^3$-G2 consisting of H and $C_{1-3}$-alkyl optionally substituted with 1 to 3 F.

According to another embodiment, $R^3$ is selected from the group $R^3$-G3 consisting of H, $CH_3$, $CH_2CH_3$, and $CH_2CH_2CH_3$.

According to another embodiment, $R^3$ is selected from the group $R^3$-G4 consisting of H.

According to another embodiment, $R^3$ is selected from the group $R^3$-G5 consisting of $CH_3$, $CH_2CH_3$, and $CH_2CH_2CH_3$.

According to one embodiment, $R^4$ is selected from the group $R^4$-G1a consisting of $C_{1-6}$-alkyl
optionally substituted with 1 to 3 F and
optionally substituted with 1 to 2 substituents independently selected from —CN, —CONH$_2$, —CONH($C_{1-4}$-alkyl), —CON($C_{1-4}$-alkyl)$_2$, —OOOH, —COO—$C_{1-4}$-alkyl, $C_{1-3}$-alkyl-CO—NH—, $C_{1-3}$-alkyl-S(=O)$_2$—NH—, OH, and —O—$C_{1-3}$-alkyl optionally substituted with 1 to 3 F.

According to another embodiment, $R^4$ is selected from the group $R^4$-G2a consisting of $C_{1-6}$-alkyl
optionally substituted with 1 to 3 F and
optionally substituted with 1 substituent selected from —CN, —CONH$_2$, —CONH($C_{1-2}$-alkyl), —CON($C_{1-2}$-alkyl)$_2$, —OOOH, —COO—$C_{1-2}$-alkyl, $C_{1-2}$-alkyl-CO—NH—, $C_{1-2}$-alkyl-S(=O)$_2$—NH—, OH, and —O—$C_{1-2}$-alkyl optionally substituted with 1 to 3 F.

According to another embodiment, $R^4$ is selected from the group $R^4$-G3a consisting of $C_{1-4}$-alkyl
optionally substituted with 1 to 3 F and
optionally substituted with 1 substituent selected from —CN, —CONH$_2$, —OOOH, OH, and —O—$C_{1-2}$-alkyl optionally substituted with 1 to 3 F.

According to another embodiment, $R^4$ is selected from the group $R^4$-G4a consisting of $C_{1-4}$-alkyl
optionally substituted with 1 group selected from F and OCF$_3$.

According to another embodiment, $R^4$ is selected from the group $R^4$-G5a consisting of

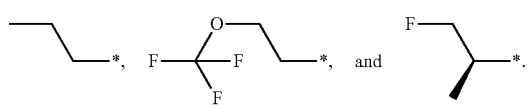

According to one embodiment, $R^4$ is selected from the group $R^4$-G1b consisting of —$C_{0-3}$-alkylene-$C_{3-10}$-cycloalkyl and —$C_{0-3}$-alkylene-$C_{3-10}$-heterocyclyl
wherein said alkylene is optionally substituted with 1 to 2 substituents selected from F and $CH_3$, wherein 1 >CH$_2$ group of said alkylene is optionally replaced by a

moiety,
wherein said cycloalkyl and heterocyclyl are saturated mono- or bicyclic ring systems,
wherein said heterocyclyl contains 1 to 2 ring members independently selected from N, NH, >N(C$_{1-4}$-alkyl), >NCO(C$_{1-4}$-alkyl), >NCOO(C$_{1-4}$-alkyl), >NS(=O)$_2$(C$_{1-4}$-alkyl), >N-phenyl, >N-pyridinyl, >N-pyrimidinyl, and O, and
optionally 1 ring member selected from >C=O, >S(=O)$_r$, with r=0, 1, or 2,
provided that said heterocyclyl does not contain any heteroatom-heteroatom bonds other than N—N, N—O, and N—S(=O)$_{r=1,2}$ between ring members, and
wherein said cycloalkyl and heterocyclyl are optionally substituted with 1 to 2 F and optionally substituted with 1 to 2 substituents independently selected from Cl, —CN, —CONH$_2$, —CONH(C$_{1-4}$-alkyl), —CON(C$_{1-4}$-alkyl)$_2$, —COOH, —COO—C$_{1-4}$-alkyl, OH, —O—C$_{1-3}$-alkyl optionally substituted with 1 to 3 F, from >S(=O)$_2$—C$_{1-4}$-alkyl and C$_{1-4}$-alkyl optionally substituted with 1 to 3 F or with 1 substituent selected from —CN, OH, —O—C$_{1-4}$-alkyl.

According to another embodiment, R$^4$ is selected from the group R$^4$-G2b consisting of —C$_{0-2}$-alkylene-C$_{3-8}$-cycloalkyl and —C$_{0-2}$-alkylene-C$_{3-9}$-heterocyclyl
wherein said cycloalkyl and heterocyclyl are saturated mono- or bicyclic ring systems,
wherein said heterocyclyl contains 1 ring member selected from N, NH, >NCOCH$_3$, >NCOO(C$_{1-2}$-alkyl), >NS(=O)$_2$CH$_3$, >N-pyrimidinyl, O, and >S(=O)$_2$,
wherein said cycloalkyl and heterocyclyl are optionally substituted with 1 to 2 F and are optionally substituted with 1 to 2 substituents independently selected from —CN, OH, —OCH$_3$, >S(=O)$_2$CH$_3$ and C$_{1-3}$-alkyl optionally substituted with 2 to 3 F or with 1 group selected from —CN, OH, —O—C$_{1-4}$-alkyl.

According to another embodiment, R$^4$ is selected from the group R$^4$-G3b consisting of —C$_{0-1}$-alkylene-C$_{3-7}$-cycloalkyl and C$_{3-9}$-heterocyclyl
wherein said cycloalkyl and heterocyclyl are saturated mono- or bicyclic ring systems,
wherein said heterocyclyl contains 1 ring member selected from N, NH, >NCOCH$_3$, >NCOO(C$_{1-2}$-alkyl), >NS(=O)$_2$CH$_3$, >N-pyrimidinyl, O, and >S(=O)$_2$,
wherein said cycloalkyl is optionally substituted with 1 to 2 F or optionally substituted with 1 to 2 CH$_3$ groups or optionally substituted with 1 substituent selected from CH$_2$CH$_3$, —CN, CH$_2$OH, C(CH$_3$)$_2$OH, CHF$_2$, CF$_3$, OH, —OCH$_3$, and >S(=O)$_2$CH$_3$,
wherein said heterocyclyl is optionally substituted with 2 F or optionally substituted with 1 to 2 CH$_3$ groups or optionally substituted with 1 substituent selected from CH$_2$CH$_3$ and C(CH$_3$)$_2$H.

According to another embodiment, R$^4$ is selected from the group R$^4$-G4b consisting of

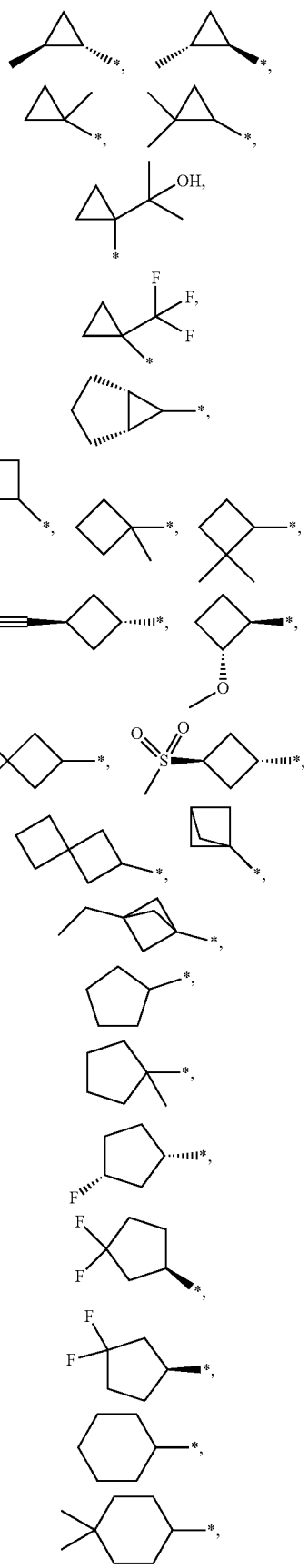

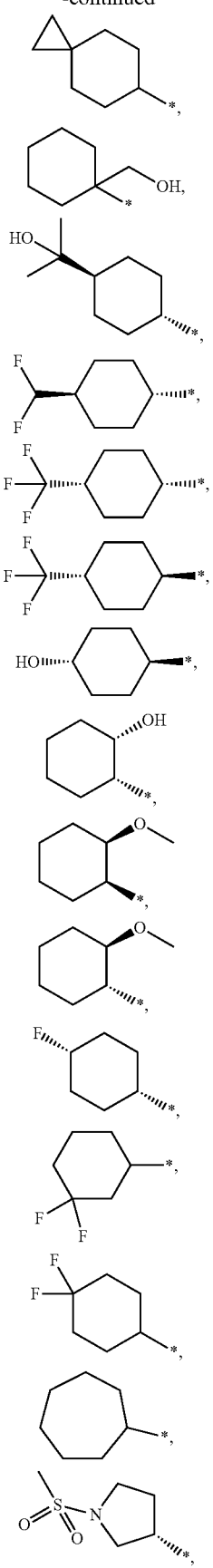
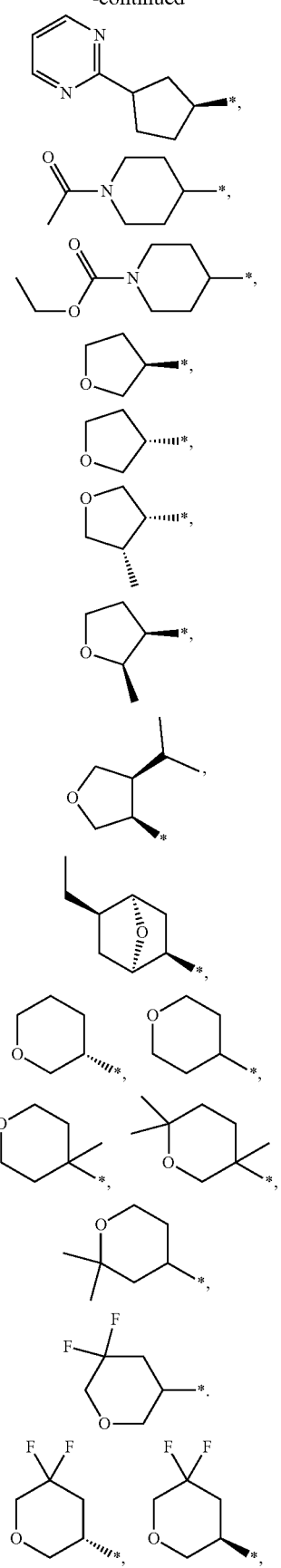

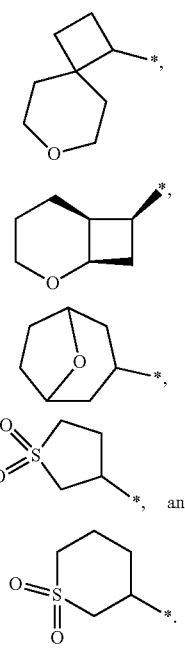

According to another embodiment, R⁴ is selected from the group R⁴-G5b consisting of

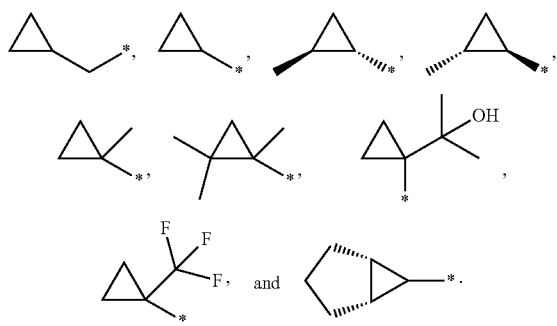

According to another embodiment, R⁴ is selected from the group R⁴-G6b consisting of

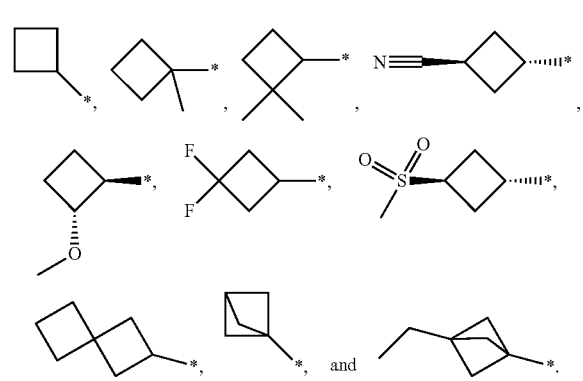

According to another embodiment, R⁴ is selected from the group R⁴-G7b consisting of

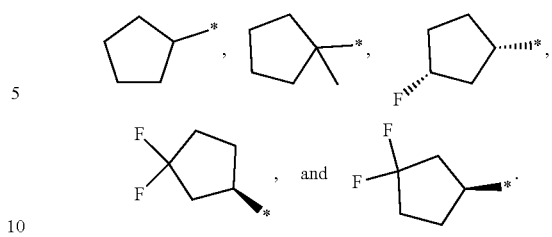

According to another embodiment, R⁴ is selected from the group R⁴-G8b consisting of

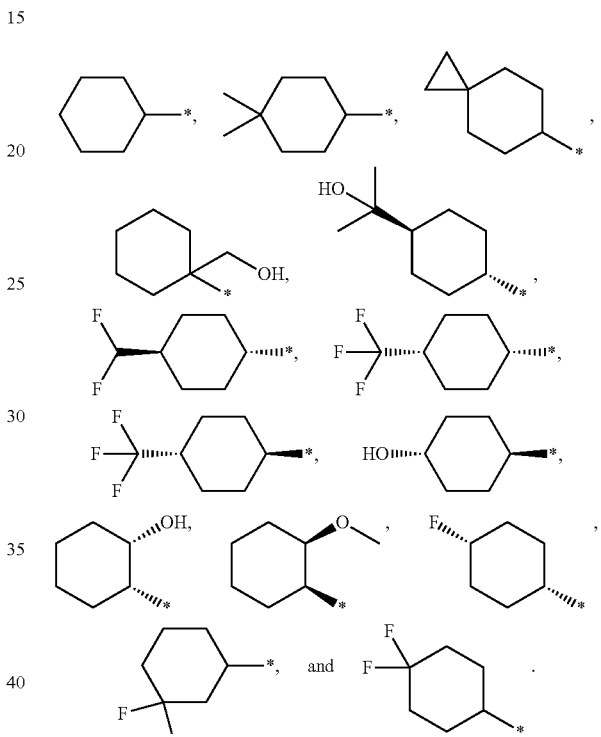

According to another embodiment, R⁴ is selected from the group R⁴-G9b consisting of

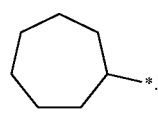

According to another embodiment, R⁴ is selected from the group R⁴-G10b consisting of

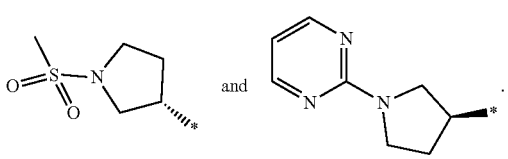

According to another embodiment, R⁴ is selected from the group R⁴-G11b consisting of

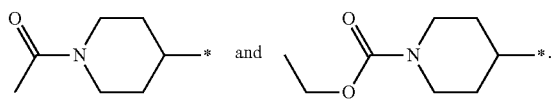 and

According to another embodiment, R⁴ is selected from the group R⁴-G12b consisting of

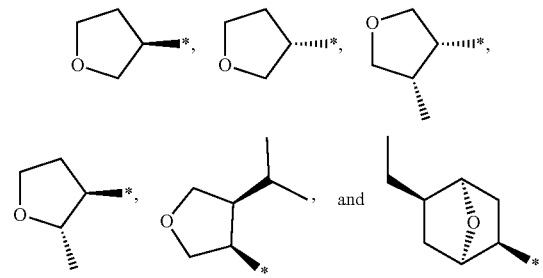

According to another embodiment, R⁴ is selected from the group R⁴-G13b consisting of

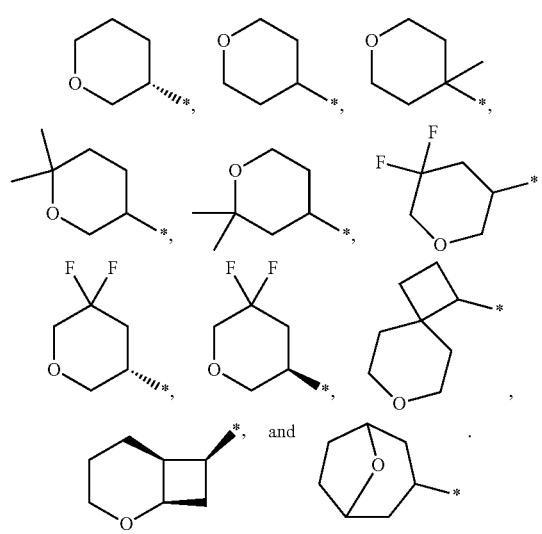

According to another-embodiment R⁴ is selected from the group R⁴-G14b consisting of

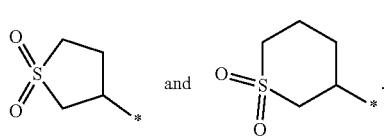 [SMILES: *C1CCS(=O)(=O)C1 ; *C1CCCS(=O)(=O)C1]

According to one embodiment, R⁴ is selected from the group R⁴-G1c consisting of —C₀₋₃-alkylene-phenyl and —C₀₋₃-alkylene-heteroaryl wherein said alkylene is optionally substituted with 1 to 2 substituents selected from F and CH₃, wherein 1 >CH₂ group of said alkylene is optionally replaced by a

moiety or by a

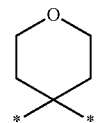

moiety or wherein 1 —CH₂—CH₂— group of said alkylene is optionally replaced by a

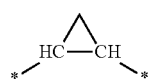

moiety or by a

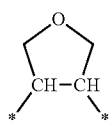

moiety, wherein said heteroaryl is a 5-membered monocycle containing 1 ring member selected from N, NH, O, and S and optionally further containing 1 to 2 ring members N, or a 6-membered monocycle containing 1 to 2 ring members N, and wherein said phenyl and heteroaryl are optionally substituted with 1 to 3 substituents independently selected from F, Cl, Br, C₃₋₄-cycloalkyl, —CN, —CONH₂, —CONH(C₁₋₄-alkyl), —CON(C₁₋₄-alkyl)₂, —OOOH, —COO—C₁₋₄-alkyl, —NHCO—C₁₋₄-alkyl, —NHS(=O)₂—C₁₋₄-alkyl, —S(=O)C₁₋₄-alkyl with r=0, 1, or 2, from —O—C₁₋₄-alkyl optionally substituted with 1 to 3 F, and from C₁₋₄-alkyl optionally substituted with 1 to 3 F or with 1 substituent selected from —CN, OH, and —O—C₁₋₄-alkyl.

According to another embodiment, R⁴ is selected from the group R⁴-G2c consisting of —C₀₋₂-alkylene-phenyl and —C₀₋₂-alkylene-heteroaryl, wherein said alkylene is optionally substituted with 1 to 2 CH₃, wherein 1 >CH₂ group of said alkylene is optionally replaced by a

moiety or by a

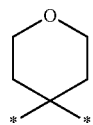

moiety or
wherein 1 —CH$_2$—CH$_2$— group of said alkylene is optionally replaced by

moiety or by a

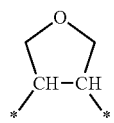

moiety,
wherein said heteroaryl is a 5-membered monocycle containing 1 ring member selected from N, NH, O, and S and optionally further containing 1 ring member N, or a 6-membered monocycle containing 1 to 2 ring members N, and
wherein said phenyl and heteroaryl are optionally substituted with 1 to 2 substituents independently selected from F, C, Br, —CN, —O—C$_{1-3}$-alkyl optionally substituted with 1 to 3 F, and from C$_{1-3}$-alkyl optionally substituted with 1 to 3 F or with 1 substituent selected from —CN and —O—C$_{1-2}$-alkyl.

According to another embodiment, R$^4$ is selected from the group R$^4$-G3c consisting of —C$_{1-2}$-alkylene-phenyl and C$_{0-1}$-alkylene-heteroaryl,
wherein 1 >CH$_2$ group of said alkylene is optionally replaced by a

moiety or by a

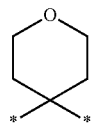

moiety or
wherein 1 —CH$_2$—CH$_2$— group of said alkylene is optionally replaced by a

moiety or by a

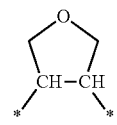

moiety,
wherein said heteroaryl is a 5- to 6-membered monocycle containing 1 ring member =N— and optionally containing 1 ring member independently selected from =N— and O, and
wherein said phenyl and heteroaryl are optionally substituted with 1 to 2 substituents independently selected from F, Cl, OCH$_3$, and CH$_3$.

According to another embodiment, R$^4$ is selected from the group R$^4$-G4c consisting of

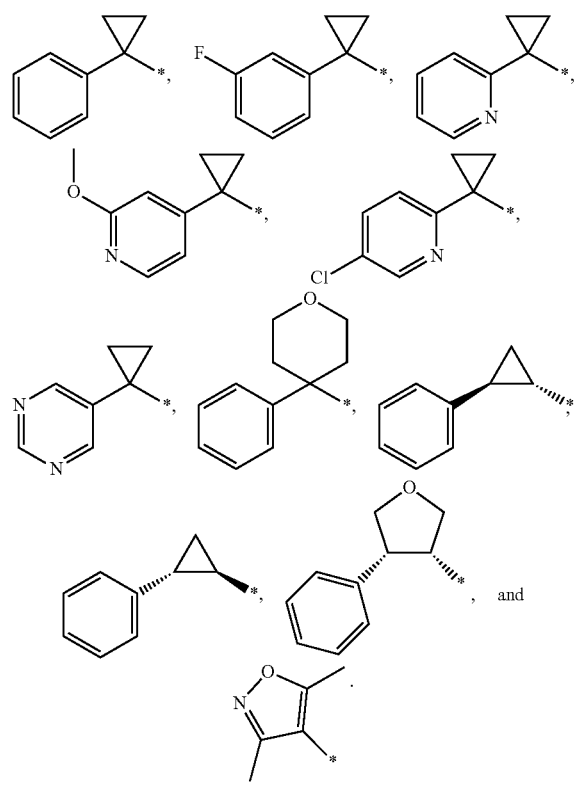

According to another embodiment, R$^4$ is selected from the group R$^4$-G5c consisting of

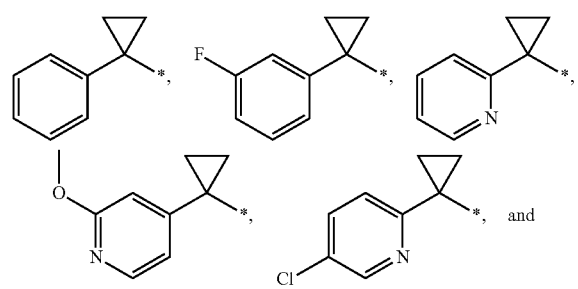

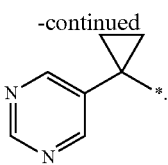

According to another embodiment, R⁴ is selected from the group R⁴-G6c consisting of

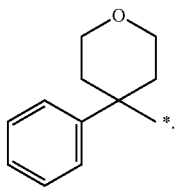

According to another embodiment, R⁴ is selected from the group R⁴-G7c consisting of

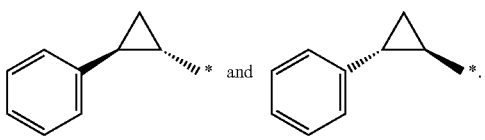

According to another embodiment, R⁴ is selected from the group R⁴-G8c consisting of

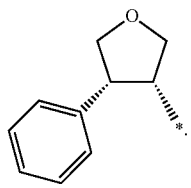

According to another embodiment, R⁴ is selected from the group R⁴-G9c consisting of

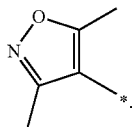

According to one embodiment, R⁴ is selected from the group R⁴-G1d consisting of 7- to 12-membered fused bicyclic aryl, heteroaryl, or heterocyclyl
wherein said bicyclic aryl, heteroaryl, or heterocyclyl consists of
one non-aromatic ring that is attached to the amide N atom in formula (I) and optionally contains 1 to 2 ring members independently selected from >N—, >NH, >N(C₁₋₄-alkyl), >N(CO—C₁₋₃-alkyl), >N(S(=O)₂—C₁₋₃-alkyl), and O, and
optionally contains 1 ring member selected from C=O and S(=O)ᵣ, with r=0, 1, or 2, and of
one aromatic ring selected from phenyl, pyrrole, furan, and thiophene in each of which 1 to 2 CH ring members are optionally replaced with N,
wherein said bicyclic aryl, heteroaryl, or heterocyclyl is optionally substituted with 1 to 4 F,
is optionally substituted with 1 to 4 C₁₋₃-alkyl optionally substituted with 1 to 4 F, and
is optionally substituted with 1 to 2 substituents selected from the group consisting of Cl, —CN, —CONH₂, —CONH(C₁₋₄-alkyl), —CON(C₁₋₄-alkyl)₂, —COOH, —COO—C₁₋₄-alkyl, HO—C₁₋₃-alkylene-, C₁₋₃-alkyl-O—C₁₋₃-alkylene-, NH₂, C₁₋₃-alkyl-CO—NH—, C₁₋₃-alkyl-S(=O)₂—NH—, OH, and C₁₋₃-alkyl-O— optionally substituted with 1 to 3 F.

According to another embodiment, R⁴ is selected from the group R⁴-G2d consisting of 8- to 11-membered fused bicyclic aryl, heteroaryl, or heterocyclyl,
wherein said bicyclic aryl, heteroaryl, or heterocyclyl consists of
one non-aromatic ring that is attached to the amide N atom in formula (I) and optionally contains 1 ring member selected from >N—, >NH, >NCH₃, >NCOCH₃, >NS(=O)₂CH₃, and O, and
optionally contains 1 ring member selected from C=O and S(=O)₂,
and of
one aromatic ring selected from phenyl, pyrrole, furan, and thiophene in each of which 1 CH ring member is optionally replaced with N,
wherein said bicyclic aryl, heteroaryl, or heterocyclyl is optionally substituted with 1 to 2 F,
is optionally substituted with 1 to 2 C₁₋₂-alkyl optionally substituted with 1 to 2 F, and
is optionally substituted with 1 to 2 substituents selected from Cl, —CN, —CONH₂, —CONHCH₃, —CON(CH₃)₂, —COOH, —COO—C₁₋₂-alkyl, HO—C₁₋₃-alkylene-, CH₃—O—C₁₋₃-alkylene-, NH₂, CH₃—CO—NH—, CH₃—S(=O)₂—NH—, OH, and CH₃-alkyl-O— optionally substituted with 1 to 3 F.

According to another embodiment, R⁴ is selected from the group R⁴-G3d consisting of 9- to 10-membered fused bicyclic aryl, heteroaryl, or heterocyclyl
wherein said bicyclic aryl, heteroaryl, or heterocyclyl consists of
one non-aromatic ring that is attached to the amide N atom in formula (I) and optionally contains 1 ring member selected from >N— and O,
and of
one aromatic ring selected from phenyl, pyridine, pyrazole, and thiazole,
wherein said bicyclic aryl, heteroaryl, or heterocyclyl is optionally substituted with 1 substituent selected from F, CH₃, CH₂CH₃, —CN, NH₂, and OH.

According to another embodiment, R⁴ is selected from the group R⁴-G4d consisting of

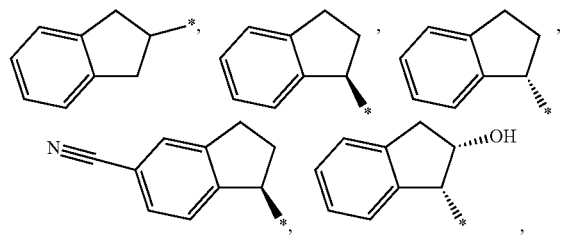

31

-continued

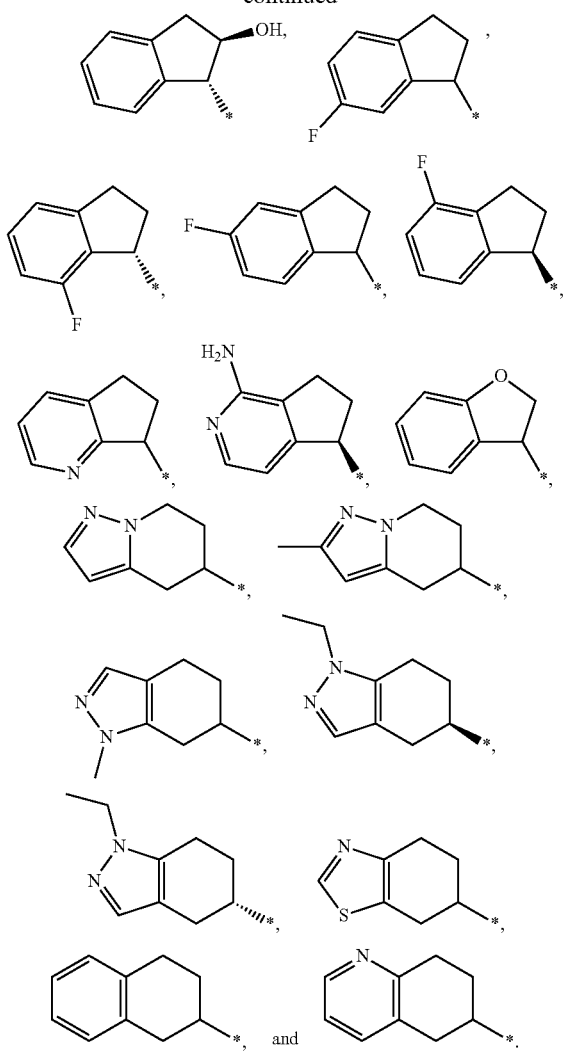

According to another embodiment, $R^4$ is selected from the group $R^4$-G5d consisting of

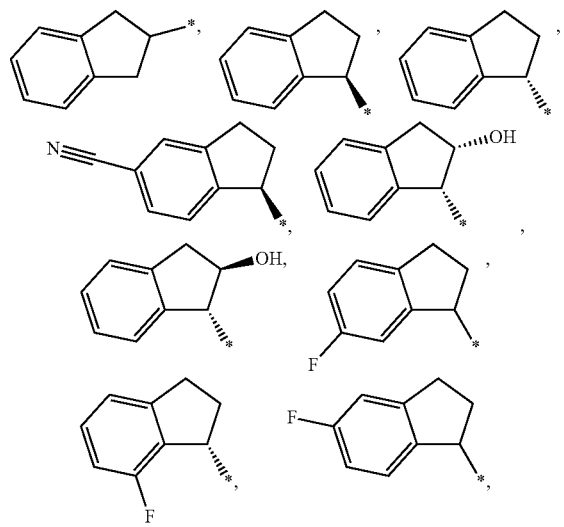

32

-continued

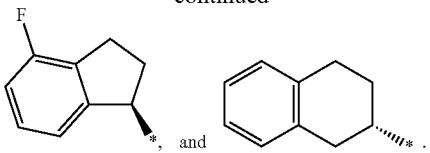

According to another embodiment, $R^4$ is selected from the group $R^4$-G6d consisting of

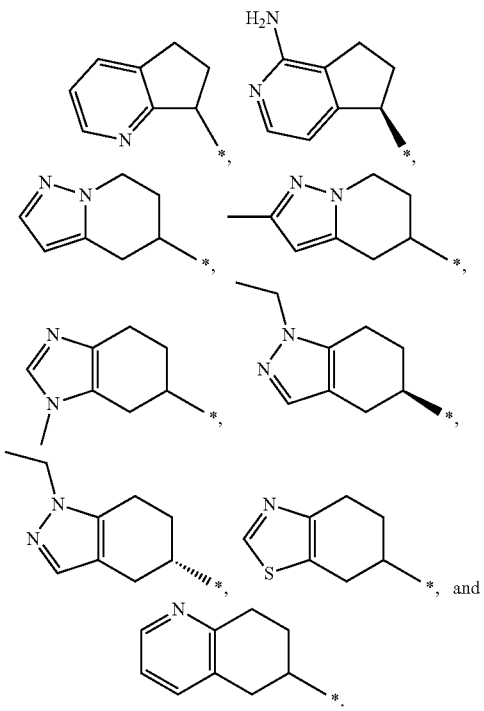

According to another embodiment, $R^4$ is selected from the group $R^4$-G7d consisting of

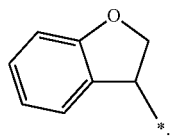

According to one embodiment, $R^3$ and $R^4$ are selected from the group $R^{3/4}$-G1a in which $R^3$ and $R^4$, together with the amide N atom they are attached to, form a saturated 3- to 8-membered monocyclic heterocyclyl
- optionally further containing 1 to 2 ring members independently selected from >NH, >N($C_{1-4}$-alkyl), >N(CO—$C_{1-3}$-alkyl), >N(S(=O)$_2$—$C_{1-3}$-alkyl), and O, and
- optionally containing 1 ring member selected from >C=O and >S(=O)$_r$, with r=0, 1, or 2,
- provided that said heterocyclyl does not contain any heteroatom-heteroatom bonds other than N—N, N—O, and N—S(=O)$_{r=1,2}$ between ring members,
  wherein said heterocyclyl is optionally substituted with 1 to 4 F,
- is optionally substituted with 1 to 4 $C_{1-3}$-alkyl optionally substituted with 1 to 3 F, and is optionally substituted with 1 to 2 substituents selected from Cl, —CN, —CONH$_2$, —CONH(C$_{1-4}$-alkyl), —CON(C$_{1-4}$-alkyl)$_2$, —COOH, —COO—C$_{1-4}$-alkyl, HO—C$_{1-3}$-alkylene-, C$_{1-3}$-alkyl-O—C$_{1-3}$-alkylene-, C$_{1-3}$-alkyl-CO—NH—, C$_{1-3}$-alkyl-S(=O)$_2$—NH—, OH, and C$_{1-3}$-alkyl-O— optionally substituted with 1 to 3 F.

According to one embodiment, R$^3$ and R$^4$ are selected from the group R$^{3/4}$-G2a in which R$^3$ and R$^4$, together with the amide N atom they are attached to, form a saturated 4- to 7-membered monocyclic heterocyclyl
optionally further containing 1 ring member selected from >NH, >N(C$_{1-4}$-alkyl), >N(CO—C$_{1-3}$-alkyl), >N(S(=O)$_2$—C$_{1-3}$-alkyl), and O, and optionally containing 1 ring member selected from >C=O and >S(=O)$_2$,
provided that said heterocyclyl does not contain any heteroatom-heteroatom bonds other than N—S(=O)$_{r=1,2}$ between ring members,
wherein said heterocyclyl is optionally substituted with 1 to 2 F,
is optionally substituted with 1 to 2 C$_{1-3}$-alkyl optionally substituted with 2 to 3 F, and
is optionally substituted with 1 substituent selected from Cl, —CN, —CON(C$_{1-3}$-alkyl)$_2$, —COO—C$_{1-3}$-alkyl, C$_{1-3}$-alkyl-O—C$_{1-3}$-alkylene-, and C$_{1-3}$-alkyl-O—.

According to one embodiment, R$^3$ and R$^4$ are selected from the group R$^{3/4}$-G3a in which R$^3$ and R$^4$, together with the amide N atom they are attached to, form a saturated 4- to 6-membered monocyclic heterocyclyl
optionally further containing 1 ring member O that is non-adjacent to the amide N atom,
wherein said heterocyclyl is optionally substituted with 1 to 2 F or is optionally substituted with 1 to 2 CH$_3$.

According to one embodiment, R$^3$ and R$^4$ are selected from the group R$^{3/4}$-G4a in which R$^3$ and R$^4$, together with the amide N atom they are attached to, form a heterocyclyl selected from the group consisting of

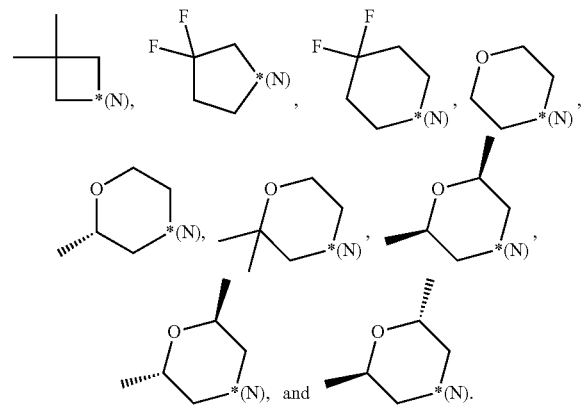

According to one embodiment, R$^3$ and R$^4$ are selected from the group R$^{3/4}$-G5a in which R$^3$ and R$^4$, together with the amide N atom they are attached to, form the heterocyclyl

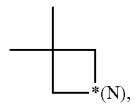

According to one embodiment, R$^3$ and R$^4$ are selected from the group R$^{3/4}$-G6a in which R$^3$ and R$^4$, together with the amide N atom they are attached to, form a heterocyclyl selected from the group consisting of

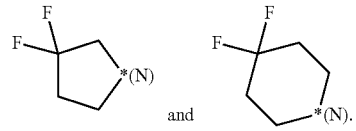

According to one embodiment, R$^3$ and R$^4$ are selected from the group R$^{34}$-G7a in which R$^3$ and R$^4$, together with the amide N atom they are attached to, form a heterocyclyl selected from the group consisting of

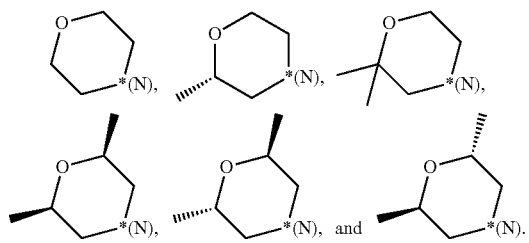

According to one embodiment, R$^3$ and R$^4$ are selected from the group R$^{3/4}$-G1b in which R$^3$ and R$^4$, together with the amide N atom they are attached to, form a saturated 5- to 12-membered bicyclic heterocyclyl
optionally further containing 1 to 3 ring members independently selected from >N—, >NH, >N(C$_{1-4}$-alkyl), >N(CO—C$_{1-3}$-alkyl), >N(S(=O)$_2$—C$_{1-3}$-alkyl), and O, and
optionally containing 1 ring member selected from >C=O and >S(=O)$_r$, with r=0, 1, or 2,
provided that said heterocyclyl does not contain any heteroatom-heteroatom bonds other than N—N, N—O, and N—S(=O)$_{r=1,2}$ between ring members
wherein said heterocyclyl is optionally substituted with 1 to 6 F,
is optionally substituted with 1 to 4 C$_{1-3}$-alkyl optionally substituted with 1 to 3 F, and
is optionally substituted with 1 to 2 substituents selected from Cl, —CN, —CONH$_2$, —CONH(C$_{1-4}$-alkyl), —CON(C$_{1-4}$-alkyl)$_2$, —COOH, —COO—C$_{1-4}$-alkyl, HO—C$_{1-3}$-alkylene-, C$_{1-3}$-alkyl-O—C$_{1-3}$-alkylene-, C$_{1-3}$-alkyl-CO—NH—, C$_{1-3}$-alkyl-S(=O)$_2$—NH—, OH, and C$_{1-3}$-alkyl-O—.

According to one embodiment, R$^3$ and R$^4$ are selected from the group R$^{3/4}$-G2b in which R$^3$ and R$^4$, together with the amide N atom they are attached to, form a saturated 6- to 11-membered bicyclic heterocyclyl
optionally further containing 1 ring member selected from >N—, >NH, >N(C$_{1-4}$-alkyl), >N(CO—C$_{1-3}$-alkyl), >N(S(=O)$_2$—C$_{1-3}$-alkyl), and O, and
optionally containing 1 ring member selected from >C=O and >S(=O)$_r$, with r=0, 1, or 2,
provided that said heterocyclyl does not contain any O—S bonds between ring members
wherein said heterocyclyl is optionally substituted with 1 to 4 F,
is optionally substituted with 1 to 3 C$_{1-3}$-alkyl optionally substituted with 1 to 3 F, and is optionally substituted with 1 to 2 substituents independently selected from Cl, —CN, —CONH$_2$, —CONH(C$_{1-4}$-alkyl), —CON(C$_{1-4}$-alkyl)$_2$, —COOH, —COO—C$_{1-4}$-alkyl, HO—C$_{1-3}$-alkylene-, C$_{1-3}$-alkyl-O—C$_{1-3}$-alkylene-, C$_{1-3}$-alkyl-CO—NH—, C$_{1-3}$-alkyl-S(=O)$_2$—NH—, OH, and C$_{1-3}$-alkyl-O—.

According to one embodiment, R$^3$ and R$^4$ are selected from the group R$^{3/4}$-G3b in which R$^3$ and R$^4$, together with the amide N atom they are attached to, form a saturated 6- to 11-membered bridged or spiro bicyclic heterocyclyl
  optionally further containing 1 ring member selected from >N—, >NH, >N(C$_{1-4}$-alkyl), and O that is non-adjacent to the amide N atom,
    wherein said heterocyclyl is optionally substituted with 1 to 2 F,

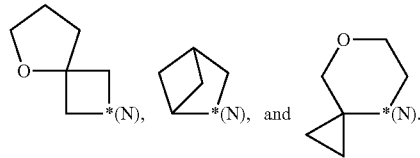

Further preferred subgeneric embodiments of the compounds of formula (I) are set forth as embodiments (I-a) to (I-z) in the following Table 1, wherein the above-mentioned substituent definitions are used. For example, the entry R$^1$-G1 in column R$^1$ and row (I-a) means that in embodiment (I-a) substituent R$^1$ is selected from the definition designated R$^1$-G1. The same applies analogously to the other variables incorporated in the general formulas.

TABLE 1

| Embodiment | R$^1$ | n | R$^2$ | R$^3$ | R$^4$ |
|---|---|---|---|---|---|
| (I-a) | R$^1$-G1 | n-G1 | R$^2$-G1 | R$^3$-G1 | R$^4$-G1a or R$^4$-G1b or R$^4$-G1c or R$^4$-G1d |
| (I-b) | R$^1$-G1 | n-G1 | R$^2$-G1 | | R$^{3/4}$-G1a or R$^{3/4}$-G1b |
| (I-c) | R$^1$-G2 | n-G2 | R$^2$-G2 | R$^3$-G2 | R$^4$-G2a or R$^4$-G2b or R$^4$-G2c or R$^4$-G2d |
| (I-d) | R$^1$-G2 | n-G2 | R$^2$-G2 | | R$^{3/4}$-G2a or R$^{3/4}$-G2b |
| (I-e) | R$^1$-G2 | n-G2 | R$^2$-G2 | R$^3$-G2 | R$^4$-G3a or R$^4$-G3b or R$^4$-G3c or R$^4$-G3d |
| (I-f) | R$^1$-G2 | n-G2 | R$^2$-G2 | | R$^{3/4}$-G3a or R$^{3/4}$-G3b |
| (I-g) | R$^1$-G2 | n-G2 | R$^2$-G2 | R$^3$-G2 | R$^4$-G4a or R$^4$-G4b or R$^4$-G4c or R$^4$-G4d |
| (I-h) | R$^1$-G2 | n-G2 | R$^2$-G2 | | R$^{3/4}$-G4a or R$^{3/4}$-G4b |
| (I-i) | R$^1$-G2 | n-G2 | R$^2$-G2 | R$^3$-G3 | R$^4$-G4a or R$^4$-G4b or R$^4$-G4c or R$^4$-G4d |
| (I-j) | R$^1$-G2 | n-G2 | R$^2$-G2 | | R$^{3/4}$-G4a or R$^{3/4}$-G4b |
| (I-k) | R$^1$-G3 | n-G2 | R$^2$-G3 | R$^3$-G3 | R$^4$-G5a or R$^4$-G4b or R$^4$-G4c or R$^4$-G4d |
| (I-L) | R$^1$-G3 | n-G2 | R$^2$-G3 | | R$^{3/4}$-G4a or R$^{3/4}$-G5b |
| (I-m) | R$^1$-G3 | Ph-G1* | | R$^3$-G3 | R$^4$-G5a or R$^4$-G4b or R$^4$-G4c or R$^4$-G4d |
| (I-n) | R$^1$-G3 | Ph-G1* | | | R$^{3/4}$-G4a or R$^{3/4}$-G5b |
| (I-o) | R$^1$-G4 | n-G4 | R$^2$-G4 | R$^3$-G3 | R$^4$-G5a or R$^4$-G4b or R$^4$-G4c or R$^4$-G4d |
| (I-p) | R$^1$-G4 | n-G4 | R$^2$-G4 | | R$^{3/4}$-G4a or R$^{3/4}$-G5b |
| (I-q) | R$^1$-G4 | Ph-G3* | | R$^3$-G3 | R$^4$-G5a or R$^4$-G4b or R$^4$-G4c or R$^4$-G4d |
| (I-r) | R$^1$-G4 | Ph-G3* | | | R$^{3/4}$-G4a or R$^{3/4}$-G5b |
| (I-s) | R$^1$-G4 | Ph-G5* | | R$^3$-G4 | R$^4$-G5a |
| (I-t) | R$^1$-G4 | Ph-G5* | | R$^3$-G4 | R$^4$-G5b |
| (I-u) | R$^1$-G4 | Ph-G5* | | R$^3$-G4 | R$^4$-G6b |
| (I-v) | R$^1$-G4 | Ph-G5* | | R$^3$-G4 | R$^4$-G7b |
| (I-w) | R$^1$-G4 | Ph-G5* | | R$^3$-G4 | R$^4$-G8b |
| (I-x) | R$^1$-G4 | Ph-G5* | | R$^3$-G4 | R$^4$-G5c or R$^4$-G5d |
| (I-y) | R$^1$-G4 | Ph-G5* | | R$^3$-G5 | R$^4$-G5a |
| (I-z) | R$^1$-G4 | Ph-G5* | | | R$^{3/4}$-G7a |

*including the corresponding substitution pattern as defined in Ph-G1, Ph-G3, and Ph-G5, respectively is optionally substituted with 1 to 2 C$_{1-3}$-alkyl optionally substituted with 1 to 3 F, and
is optionally substituted with 1 substituent selected from Cl, —CN, —CON(C$_{1-3}$-alkyl)$_2$, —COO—C$_{1-3}$-alkyl, C$_{1-3}$-alkyl-O—C$_{1-3}$-alkylene-, and C$_{1-3}$-alkyl-O—.

According to one embodiment, R$^3$ and R$^4$ are selected from the group R$^{3/4}$-G4b in which R$^3$ and R$^4$, together with the amide N atom they are attached to, form a saturated 6- to 8-membered bridged or spiro bicyclic heterocyclyl
  optionally containing 1 ring member O that is non-adjacent to the amide N atom.

According to one embodiment, R$^3$ and R$^4$ are selected from the group R$^{3/4}$-G5b in which R$^3$ and R$^4$, together with the amide N atom they are attached to, form a heterocyclyl selected from the group consisting of Particularly preferred are embodiments (1-s) to (I-z).
Particularly preferred compounds, the salts thereof, or any solvates or hydrates thereof, are those described in the section Examples and Experimental Data.

Preparation

The compounds according to the invention and their intermediates may be obtained using methods of synthesis which are known to the one skilled in the art and described in the literature of organic chemistry for example in standard textbooks, monographs, and reviews covering basic, advanced, and specialized topics of organic chemistry, in particular organic synthesis. Preferably, the compounds are obtained analogously to the methods of preparation explained more fully hereinafter, in particular as described in the experimental section. In some cases the sequence adopted in carrying out the reaction schemes may be varied. Variants of these reactions that are known to the skilled person, but are not described in detail here may also be used. The general processes for preparing the compounds according to the invention will become apparent to the skilled person on studying the schemes that follow. Starting compounds are commercially available or may be prepared by methods that are described in the literature or herein, or may be prepared in an analogous or similar manner. Before the reaction is carried out, any corresponding functional groups in the starting compounds may be protected using conventional protecting groups. These protecting groups may be cleaved again at a suitable stage within the reaction sequence using methods familiar to the skilled person and described in the literature directed to the use of protecting groups in organic synthesis.

Advantageously, the compounds according to the invention comprise an achirally substituted 7-membered ring such that racemization of this moiety during synthesis, as was observed for chirally monosubstituted 7-membered rings in structurally related compounds (Filippakopoulos et al. (Nature 2010, 468, 1067-1073); Syeda at al. (Tetrahedron Lett. 2015, 56, 3454-3457)), cannot occur and additional synthetic efforts resulting therefrom can be avoided.

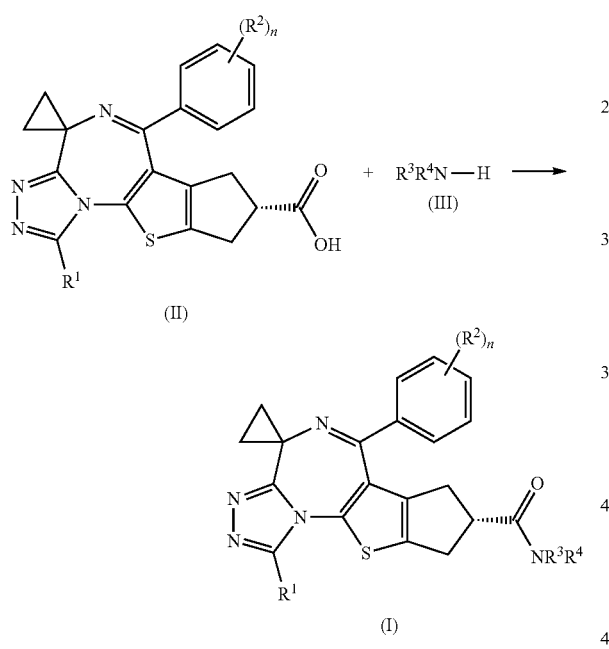

Scheme 1: Compounds of formula (I) can be prepared from the respective acids of formula (II) (either as free acid or carboxylate with a suitable metal cation such as Li$^+$, Na$^+$, K$^+$, etc.) and a suitable amine of formula (III) (either as free amine or salt such as hydrochloride, hydrobromide, etc.) by employing a suitable coupling agent (e.g., O-(7-azabenzotriazol-1-yl)-N,N,N',N'-tetramethyluronium-hexafluorophosphate (HATU), O-(benzotriazol-1-yl)-N,N,N',N'-tetramethyluronium tetrafluoroborate (TBTU), (benzotriazol-1-yloxy)tripyrrolidinophosphonium hexafluorophosphate (PyBOP), carbodiimide reagents, etc.) and a base (e.g., triethylamine, N,N-diisopropyl-ethylamine, pyridine, etc.) in a suitable solvent (e.g., DCM, THF, 1,4-dioxane, DMF, N,N-dimethylacetamide, and 1-methyl-2-pyrrolidinone) at −20° C. to 100° C.; R$^1$, R$^2$, R$^3$, R$^4$, and n in Scheme 1 have the meanings as defined hereinbefore. Alternatively, the respective carboxylic acid is transformed into a carboxylic chloride (using, e.g., oxalyl chloride or thionyl chloride in DCM) and coupled as such with amine (III) in the presence of a suited base (e.g., triethylamine, N,N-diisopropyl-ethylamine, pyridine, etc.).

Compounds of formula (I) can also be obtained from mixtures of compounds (II) with their enantiomers by following the procedure described above and separating the two enantiomeric products by methods known to the one skilled in the art such as chromatography on chiral phase, crystallization, and enzymatic derivatization.

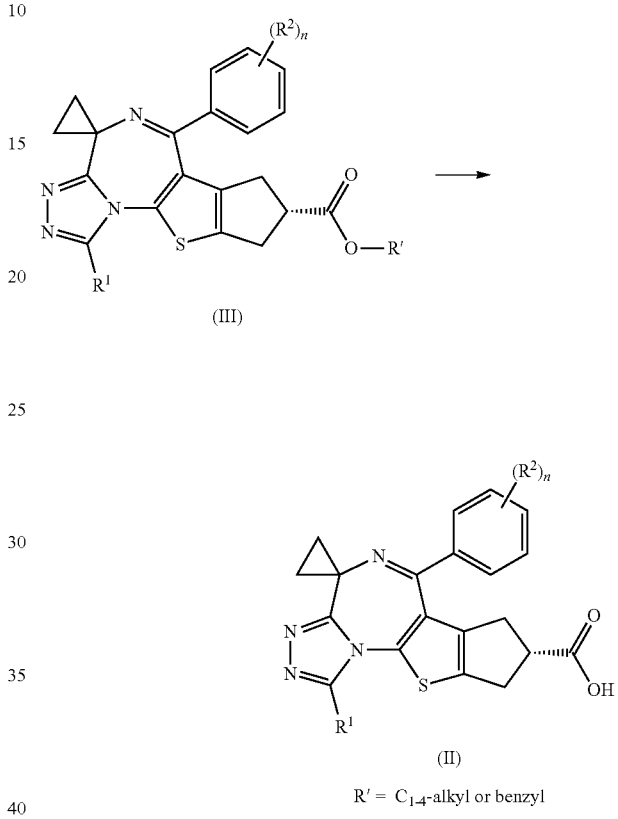

Scheme 2: Acids of formula (II), wherein R$^1$, R$^2$, and n have the meanings as defined hereinbefore, are preferably prepared from the corresponding esters (III) through hydrolysis or hydrogenolysis depending on the nature of R'. Lower alkyl group esters such as ethyl or methyl esters are preferably cleaved by hydrolysis with a hydroxide salt such as NaOH, LiOH, or KOH in a mixture of water and a suitable miscible solvent (e.g., THF, MeOH, EtOH, 1,4-dioxane, or mixtures of these) at ambient or elevated temperature. The acid may be isolated either as a salt with the metal cation or as a carboxylic acid. A tert-butyl ester is preferably cleaved by treatment with an acid (e.g., hydrochloric acid or TFA) in a suitable solvent (e.g., DCM, 1,4-dioxane, MeOH, EtOH, THF, water, or mixtures of these). A benzyl ester is preferably cleaved by hydrogenolysis with a suitable catalyst (e.g., palladium on carbon) in a suitable solvent (e.g., EtOH, MeOH, THF, DCM, or EtOAc) under an atmosphere of hydrogen (preferably 1 to 5 bar).

Compounds of formula (II) can also be obtained from mixtures of compounds (III) with their enantiomers by following the procedure described above and separating the two enantiomeric products by methods known to the one skilled in the art such as chromatography on chiral phases, crystallization, and enzymatic derivatization.

Scheme 3

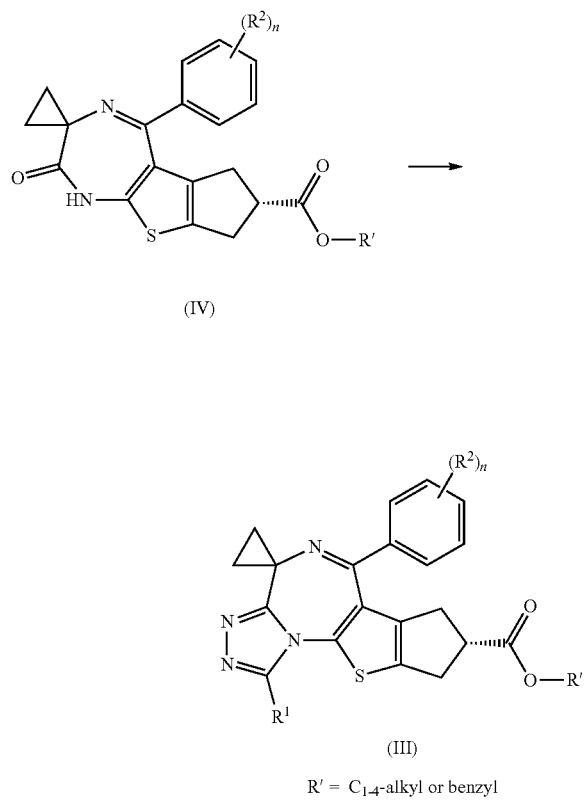

(IV)

(III)

R' = C$_{1-4}$-alkyl or benzyl

Scheme 3: Esters of formula (III), wherein R$^1$, R$^2$, and n have the meanings as defined hereinbefore, may be prepared from amides (IV) employing different synthesis strategies. A more preferred proceeding comprises the transformation of the amide group in (IV) into the corresponding imidoyl chloride or phosphoric ester anhydride employing diethyl chlorophosphate in the presence of a base (e.g., 1,8-diazabicyclo[5.4.0]undecene (DBU)) in a suited solvent (e.g., THF, 1,4-dioxane, etc.) at medium temperature (preferably between 0° C. and 40° C.). Subsequently, the accordingly decorated acyl hydrazine (R$^1$—CO—NHNH$_2$) is added to the such activated amide to provide the N-acylamino amidine derivative that can be transformed into the triazole by heating (contingently up to 140° C.).

Alternatively, the triazole (III) may be obtained by applying a 3-step procedure via the thioamide of amide (IV) that is subsequently treated with hydrazine to give the corresponding N-amino amidine that in turn is transformed into the triazole by treatment with the appropriate orthoester (R$^1$—C(OC$_{1-2}$-alkyl)$_3$). This proceeding, variations thereof, and alternative synthesis routes are reported in the literature of organic chemistry and are known to the one skilled in the art (see, e.g., EP0388789A1 and EP0254245A1).

Compounds of formula (III) can also be obtained from mixtures of compounds (IV) with their enantiomers by following the various procedures described above and separating the two enantiomeric products by methods known to the one skilled in the art such as chromatography on chiral phases, crystallization, and enzymatic derivatization.

Scheme 4

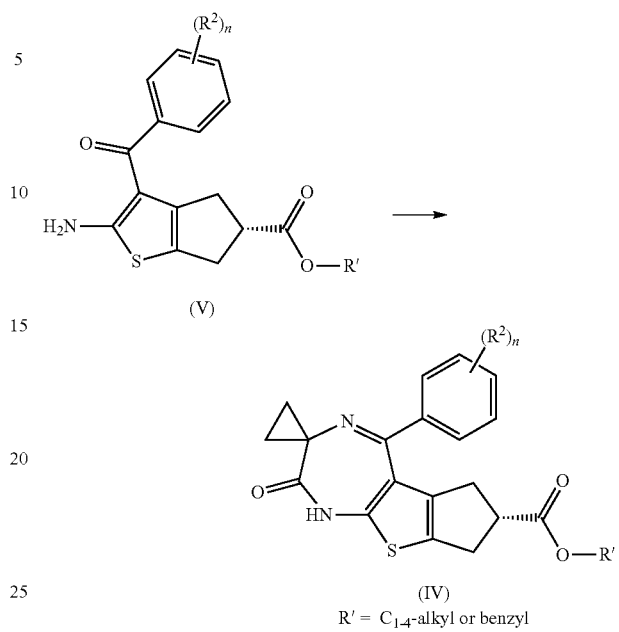

(V)

(IV)

R' = C$_{1-4}$-alkyl or benzyl

Scheme 4: Esters of formula (IV), wherein R$^2$ and n have the meanings as defined hereinbefore, may be prepared from ketones (V) in one, two, or three separate synthesis steps. A well-established synthesis of compound (IV) runs via the N-(1-aminocyclopropyl)carbonyl derivative of compound (V) that may be obtained by treatment of compound (V) with the hydrogen chloride salt of 1-aminocyclopropane-1-carbonyl chloride in a suited solvent (e.g., 1,4-dioxane) at 0° C. to 80° C. The seven-membered ring is then formed by reacting the amino group with the keto group with the help of suited additives in an apt solvent (e.g., silica gel in toluene, pyridine in HOAc, pyridine and methanesulfonic acid or triluoromethanesulfonic acid in 1,4-dioxane) at temperatures between 0° C. and 130° C. to give compound (IV).

Compounds (IV) may also be obtained in only one reaction step from compounds (V) as reported in Org. Lett. 2017, 19, 1454-1457.

Compounds of formula (IV) can also be obtained from mixtures of compounds (V) with their enantiomers by following the various procedures described above and separating the two enantiomeric products by methods known to the one skilled in the art such as chromatography on chiral phases, crystallization, and enzymatic derivatization.

Scheme 5

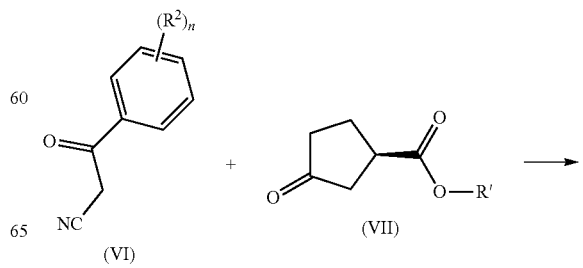

(VI)    (VII)

-continued

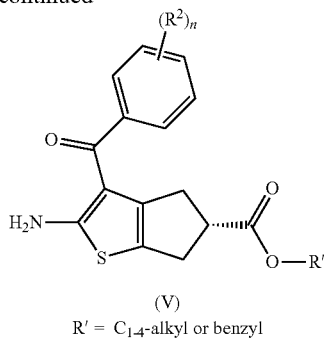

(V)
R' = C$_{1-4}$-alkyl or benzyl

Scheme 5: Compounds of formula (V) can be prepared from cyanoketones (VI) and ketones (VII) following the protocol reported for the so-called Gewald reaction; R$^2$ and n in Scheme 6 have the meanings as defined hereinbefore. Accordingly, compounds (VI) and (VII) are combined and treated with a base (e.g., NEt$_3$, HNEt$_2$, morpholine, piperidine, pyridine, etc.) in the presence of elemental sulfur in a solvent (e.g., MeOH, EtOH, DMF, 1,4-dioxane, etc.) at 0° C. to 120° C.

Alternatively, this transformation may be carried out in two separate steps, forming the condensation product from compounds (VI) and (VII) in the first step (Knoevenagel reaction) and the product (V) in the second upon treatment with elemental sulfur and a base.

Variations of these proceedings have been reported in the literature of organic chemistry.

Compounds (VI) are known compounds or can be prepared in analogy to the former. Principal and specific access to the racemic or enantiomerically enriched or pure compounds (VII) have been reported in the literature of organic chemistry (see, e.g., EP0388789A1, Archiv der Pharmazie 1996, 329, 291-300, and Green Chem. 2017, 19, 5122-5130). The racemic mixtures can be resolved into their pure enantiomers employing procedures known to the one skilled in the art such as crystallization or chromatography on chiral phase.

Scheme 6

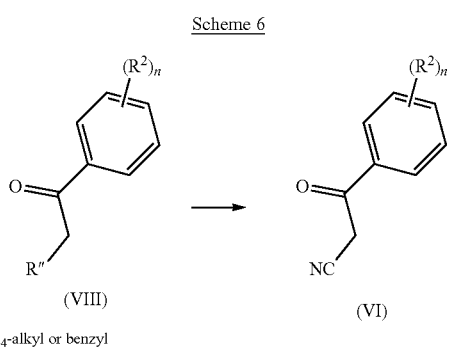

R" = C$_{1-4}$-alkyl or benzyl

Scheme 6: Cyanoketones of formula (VI), wherein R$^2$ and n have the meanings as defined hereinbefore, are preferably prepared from the corresponding ester (VIII) and a deprotonated acetonitrile (NCCH$_2$) species in a suited solvent (e.g., THF, toluene, MeCN, DMF, DMSO, 1,4-dioxane, etc.) at −78° C. to 100° C. The deprotonated acetonitrile species is prepared from acetonitrile by deprotonation with a suited base (e.g., NaH, LiNiPr$_2$, LiN(SiMe$_3$)$_2$, KOtBu, etc.) preferably in one of the solvents used for the subsequent reaction with ester (VIII) at −78° C. to 40° C., depending on the base used. Further synthesis routes and procedures to prepare compounds of formula (VI) are reported in the literature of organic chemistry.

The compounds of formula (I) may be resolved into their stereoisomers as mentioned below. Thus, for example, cis/trans mixtures may be resolved into their cis and trans isomers, diastereomeric mixtures may be separated into their diastereomers, and racemic compounds may be separated into their enantiomers.

The cis/trans mixtures may be resolved, for example, by chromatography into the cis and trans isomers thereof. The compounds of formula (I) which occur as stereoisomers may be separated by methods known per se into their pure stereoisomers of general formula (I) by taking advantage of the different physico-chemical properties of the stereoisomers using methods known per se, e.g., chromatography and/or fractional crystallization.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g., acids, their activated derivatives, or alcohols. Separation of the diastereomeric mixture of salts or derivatives thus obtained may be achieved by taking advantage of their different physico-chemical properties, e.g., differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula (I) may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled person from the literature.

Pharmacological Activity and Suitability for Pharmaceutical Applications

The activity of the compounds of the invention as well as their suitability for pharmaceutical applications may be demonstrated using the following assays:

Biological Methods

The ability of compounds of formula (I) to inhibit the activation of the PAF receptor (PAFR) by the PAF C-16 ligand (PAF) is determined using the following cellular HTRF IP1 assay (IP1 Gq assay kit from Cisbio, Cat. no.: 62IP1APEJ) in assay buffer (1×HBSS, 20 mM Hepes, pH 7.4, 50 mM LiCl and containing 0.1% (w/v) BSA):

Evaluation of the Inhibition of PAFR Activation Using an Endpoint Assay

HEK293 cells overexpressing human PAFR (produced in-house) are seeded into a Poly-D-Lysine coated 384 well white cell culture microtiter assay plate with lid (15.000 cells per well). Subsequently, the plates are incubated over night at 37° C./5% $CO_2$. On the next day, cells are being washed and subsequently, various concentrations of the test compounds (compounds in 100% DMSO; final concentration of DMSO in wells is 1%) are added to the assay plate via Echo 555 acoustic liquid handler. Plates are then incubated with lid for 90 minutes at 37° C./5% $CO_2$. Thereafter, PAF ligand (Cayman Chemical Company, Item no.: 60900) is added at a final concentration of 11 nM. Plates are then incubated with lid for 60 minutes at 37° C./5% $CO_2$. Then, 5 µl per well of Anti-IP1-Antibody-Cryptate solution and 5 µl per well of IP1-d2 solution are added to all wells of the plate and the plate is incubated for another 60 minutes light protected at room temperature. The emissions at 620 nm and 665 nm (Excitation wavelength: 320 nm) are measured using an Envision Reader (PerkinElmer).

$IC_{50}$ values for compounds according to the invention are shown in the following table. The number of the compound corresponds to the number of the Example in the experimental section.

The overall high potencies of the compounds according to the invention are particularly surprising in view of the teachings provided by the prior art.

For instance, EP0368175A1 discloses for hetrazepines in which the >$CH_2$ group of the 7-membered ring is monosubstituted by $R_5$ that is was surprisingly found that the (−)-enantiomers of general formula Ia, in particular where $R_5$=methyl, exhibit a substantially higher pharmacological efficacy than the (+)-enantiomers.

Specifically for example 1, which is the methyl-substituted derivative of WEB 2086 (apafant), it is observed that the (−)-enantiomer (1B) binds 35 times more strongly to the PAFR than the (+)-enantiomer (1A). This is in line with a finding in EP0480455A1 (Compound B therein) that the S-configured enantiomer has several times stronger PAF-antagonistic activity than the racemate. Of note, the PAFR affinity of example 1 as a racemate is reported in EP0368175A1 to be 16 nM, which is in the same range as the affinity of the unsubstituted WEB 2086 (15 nM; see Weber et al. (Med. Res. Rev. 1989, 9, 181-218)). It is to be concluded from these findings that one enantiomer of the methylated apafant has a higher affinity than the unsubstituted apafant while the other enantiomer has a lower affinity than the unsubstituted apafant.

TABLE 2

| Example | $IC_{50}$ (nM) | Example | $IC_{50}$ (nM) | Example | $IC_{50}$ (nM) | Example | $IC_{50}$ (nM) |
|---|---|---|---|---|---|---|---|
| 1 | 1.3 | 2 | 83 | 3 | 17 | 4 | 26 |
|  |  | 6 | 25 | 7 | 1.7 | 8 | 8.4 |
| 9 | 52 | 10 | 5.2 | 11 | 3.6 | 12 | 2.2 |
| 13 | 4.8 | 14 | 1.9 | 15 | 1 | 16 | 4.1 |
| 17 | 1.2 | 18 | 3.4 | 19 | 1.6 | 20 | 11 |
| 21 | 1.1 | 22 | 0.6 | 23 | 9.9 | 24 | 2 |
| 25 | 2.3 | 26 | 1.3 | 27 | 2.1 | 28 | 6.8 |
| 29 | 8.4 | 30 | 7.2 | 31 | 0.9 | 32 | 1.0 |
| 33 | 11 | 34 | 3.8 | 35 | 1.6 | 36 | 3.5 |
| 37 | 6.6 | 38 | 1.6 | 39 | 3.1 | 40 | 1.9 |
| 41 | 3.9 | 42 | 7.0 | 43 | 3.7 | 44 | 1.3 |
| 45 | 12 | 46 | 2.0 | 47 | 1.6 | 48 | 6.7 |
| 49 | 7.7 | 50 | 2.4 | 51 | 12 | 52 | 1.8 |
| 53 | 0.5 | 54 | 6.6 | 55 | 1.4 | 56 | 1.1 |
| 57 | 7.1 | 58 | 0.4 | 59 | 1.6 | 60 | 1.3 |
| 61 | 0.6 | 62 | 6.5 | 63 | 1.7 | 64 | 8.6 |
| 65 | 2.8 | 66 | 2.4 | 67 | 1.7 | 68 | 1.9 |
| 69 | 1.5 | 70 | 2.6 | 71 | 3.9 | 72 | 4.9 |
| 73 | 21 | 74 | 5.5 | 75 | 1.5 | 76 | 1.9 |
| 77 | 10 | 78 | 15 | 79 | 0.9 | 80 | 2.0 |
| 81 | 3.6 | 82 | 1.5 | 83 | 6.9 | 84 | 2.3 |
| 85 | 3.9 | 86 | 4.0 | 87 | 4.9 | 88 | 5.1 |
| 89 | 15 | 90 | 8.8 | 91 | 1.5 | 92 | 0.9 |
| 93 | 5.2 | 94 | 6.4 | 95 | 17 | 96 | 6.0 |
| 97 | 8.9 | 98 | 9.1 | 99 | 8.1 | 100 | 22 |
| 101 | 6.0 | 102 | 6.9 | 103 | 14 | 104 | 0.9 |
| 105 | 3.6 | 106 | 7.5 | 107 | 2.7 | 108 | 4.6 |
| 109 | 1.1 | 110 | 4.3 | 111 | 24 | 112 | 22 |
| 113 | 28 | 114 | 7.2 | 115 | 25 | 116 | 3.9 |
| 117 | 28 | 118 | 2.8 | 119 | 15 | 120 | 14 |
| 121 | 30 | 122 | 37 | 123 | 5.0 | 124 | 2.4 |
| 125 | 5.8 | 126 | 9.4 | 127 | 5.8 | 128 | 5.7 |
| 129 | 2.5 | 130* | 84 |  |  |  |  |

*ca. 3:1 mixture with enantiomer

PAFR affinity (K_i)

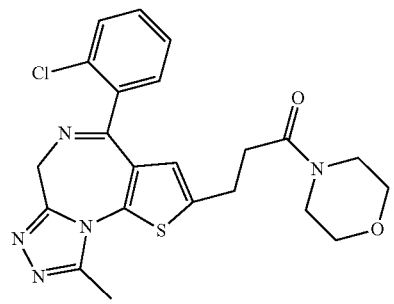 [SMILES: Cc1nnc2n1-c1sc(CCC(=O)N3CCOCC3)cc1C(c1ccccc1Cl)=NC2]

WEB 2086 (apafant)
15 nM
(see Weber et al. (Med. Res. Rev. 1989, 9, 181-218))

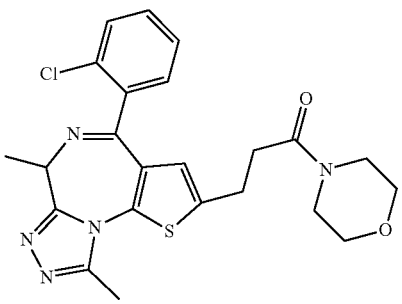 [SMILES: Cc1nnc2n1-c1sc(CCC(=O)N3CCOCC3)cc1C(c1ccccc1Cl)=NC2C]

example 1 of EP0368175A1
Compound B in EP0480455A1
racemate: 16 nM
(−)-enantiomer 35 times stronger binding than (+)-enantiomer (see EP0368175A1)
S-configured isomer with several times stronger PAF-antagonistic activity than racemate (see EP0480455A1)

Similarly, EP0368175A1 discloses as example 9d the methyl-substituted derivative of WEB 2170 (bepafant) as well as the four diastereomers thereof, (−) 9dA, (+) 9dA, (−) 9 dB, and (+) 9 dB, for which PAFR binding affinities of 70 nM, 400 nM, 8 nM, and 3000 nM, respectively, are reported. For the enantiomers of bepafant affinities of 14 nM and 660 nM, respectively, have been described in the literature (Weber et al. (Med. Res. Rev. 1989, 9, 181-218)). Also for this example, it can be derived from the literature data that only one methyl substituted isomer has improved affinity, while the other one has lower affinity in comparison to the unsubstituted parent compound.

PAFR affinity (K_i)

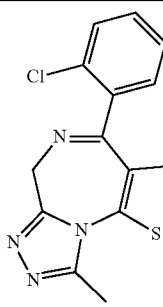

WEB 2170 (bepafant)
racemate: 15 nM
(−)-bepafant: 14 nM
(+)-bepafant: 660 nM
(see Weber et al. (Med. Res. Rev. 1989, 9, 181-218))

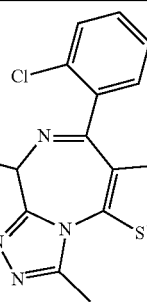

example 9d of EP0368175A1
(−) 9dA: 70 nM
(+) 9dA: 400 nM
(−) 9dB: 8 nM
(+) 9dB: 3000 nM
(see EP0368175A1)

In fact, this conclusion could be verified for the eutomer of S-bepafant and its methylated derivatives with the help of the above-mentioned assay. It was confirmed that one methyl-substituted isomer has improved activity in comparison to S-bepafant whereas the other methyl-substituted isomer has significantly lower activity.

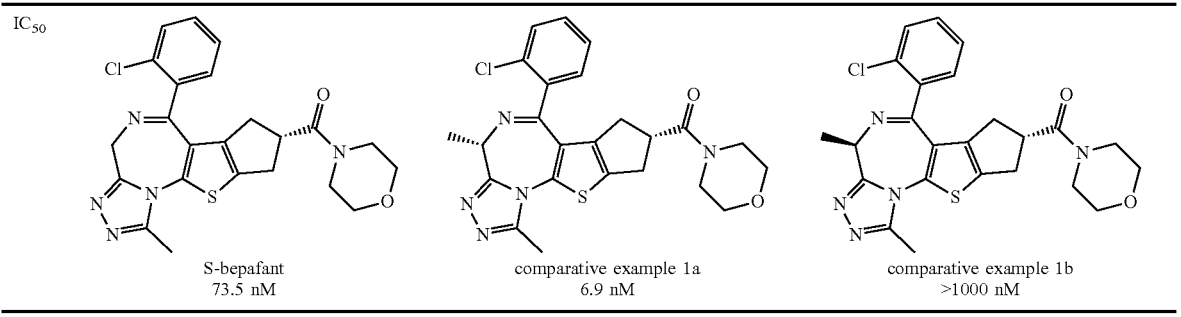

| | | | |
|---|---|---|---|
| $IC_{50}$ | <br>S-bepafant<br>73.5 nM | <br>comparative example 1a<br>6.9 nM | <br>comparative example 1b<br>>1000 nM |

Similar results were reported for a related compound class in Miyazawa et al. (Chem. Pharm. Bull. 1991, 39, 3215-3220), again showing that only one methyl-substituted isomer shows stronger PAFR binding while the other one shows weaker PAFR binding than the unsubstituted parent compound:
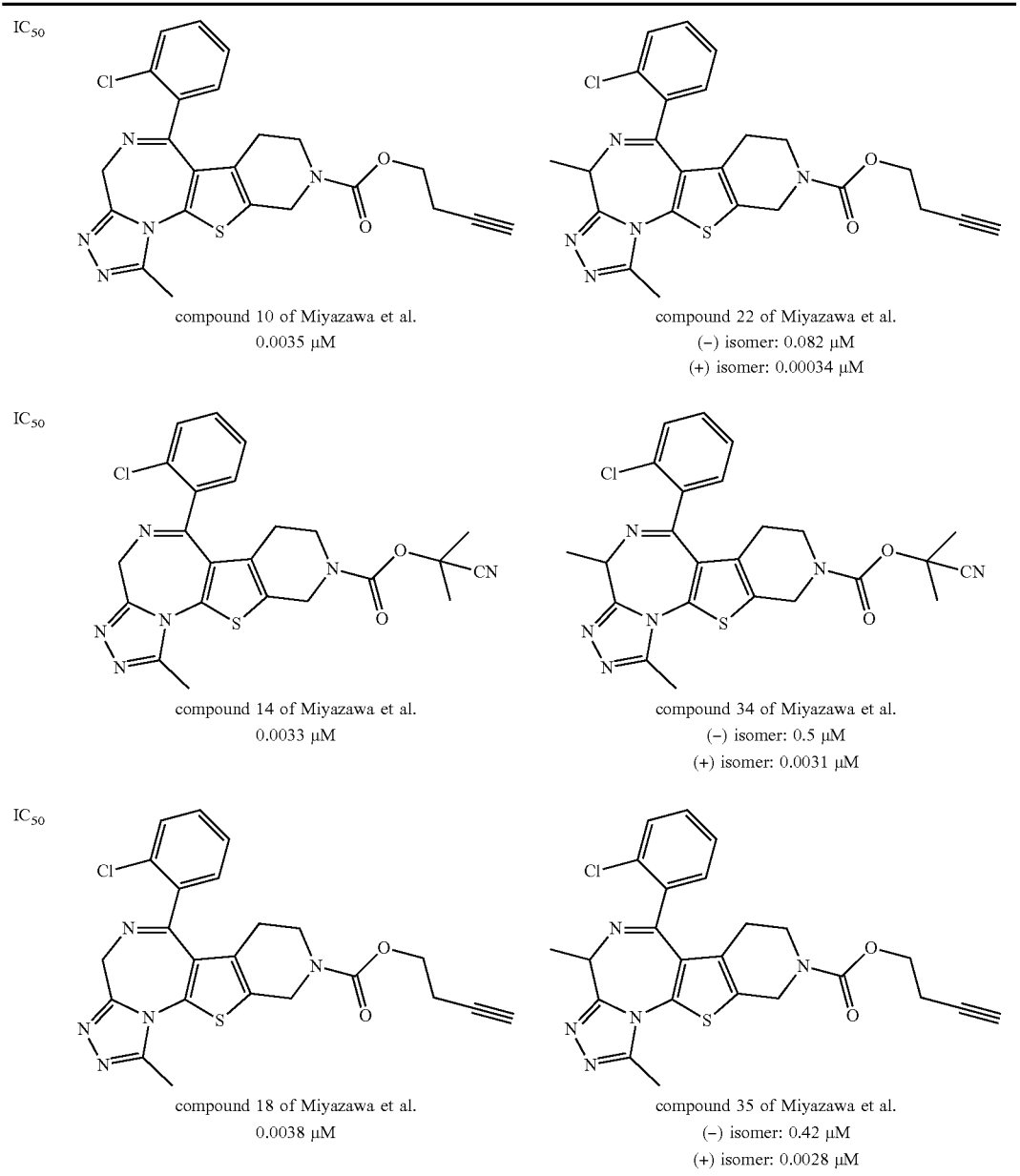

| | | |
|---|---|---|
| $IC_{50}$ | <br>compound 10 of Miyazawa et al.<br>0.0035 μM | <br>compound 22 of Miyazawa et al.<br>(−) isomer: 0.082 μM<br>(+) isomer: 0.00034 μM |
| $IC_{50}$ | <br>compound 14 of Miyazawa et al.<br>0.0033 μM | <br>compound 34 of Miyazawa et al.<br>(−) isomer: 0.5 μM<br>(+) isomer: 0.0031 μM |
| $IC_{50}$ | <br>compound 18 of Miyazawa et al.<br>0.0038 μM | <br>compound 35 of Miyazawa et al.<br>(−) isomer: 0.42 μM<br>(+) isomer: 0.0028 μM |

As a consequence of these findings, also the di-methyl- and di-ethyl-substituted compounds are described to exhibit substantially weaker binding than the unsubstituted parent compound:

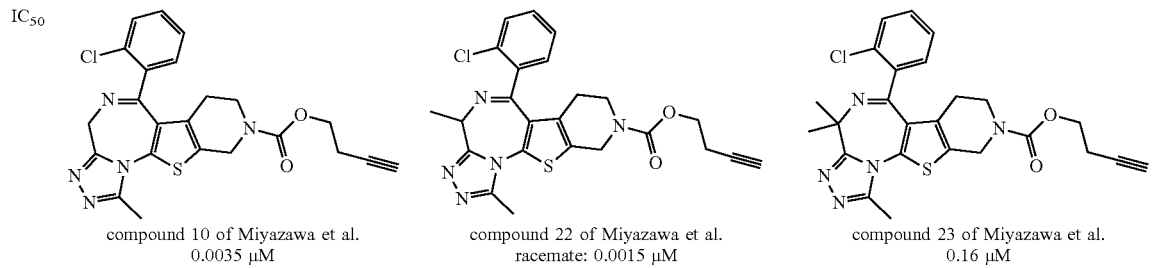

IC$_{50}$ compound 10 of Miyazawa et al.
0.0035 µM compound 22 of Miyazawa et al.
racemate: 0.0015 µM compound 23 of Miyazawa et al.
0.16 µM

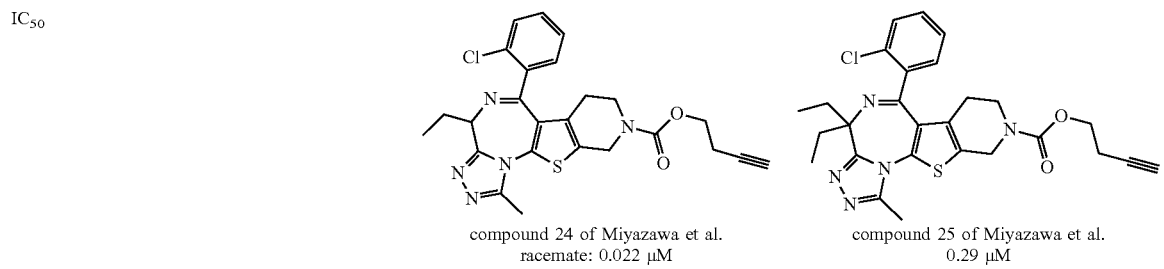

IC$_{50}$ compound 24 of Miyazawa et al.
racemate: 0.022 µM compound 25 of Miyazawa et al.
0.29 µM Altogether, the prior art teaches that mono-methyl-substitution of one of the H atoms of the >CH$_2$ group of the 7-membered ring may confer higher PAFR binding affinity to hetrazepine compounds and that, in contrast, mono-methyl-substitution of the other H atom reduces binding affinity. Accordingly, weaker binding affinities are also expected for di-substitution of said >CH$_2$ group.

Against this backdrop, it is surprising that the cyclopropylene-substituted compounds according to the invention exhibit excellent potencies. The exceptional features of the cyclopropylene substituent in this respect is furthermore underpinned by the observation that the di-methyl and cyclobutylene analogs of S-bepafant show inferior potencies than the cyclopropylene analogue (example 114).

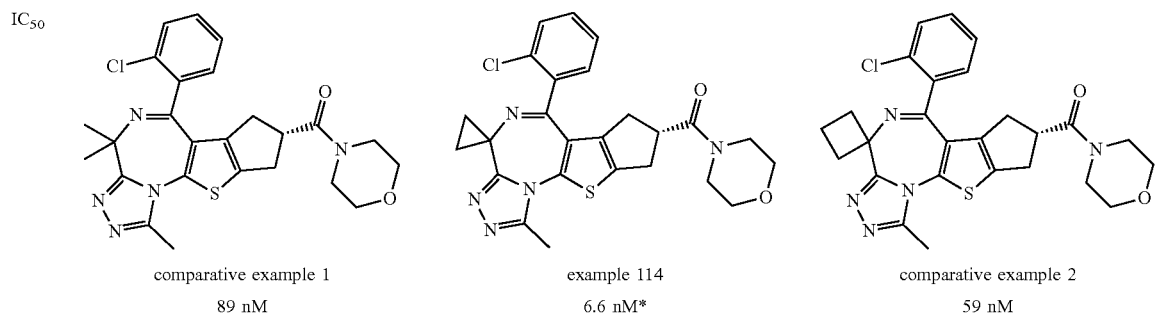

IC$_{50}$ comparative example 1
89 nM example 114
6.6 nM* comparative example 2
59 nM

*result from a dedicated head-to-head comparison assay run (thus slightly different from the data reported in Table 2)

Further comparison pairs of cyclopropylene and dimethylmethylene derivatives:
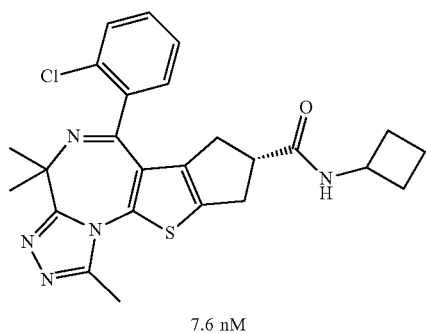
7.6 nM
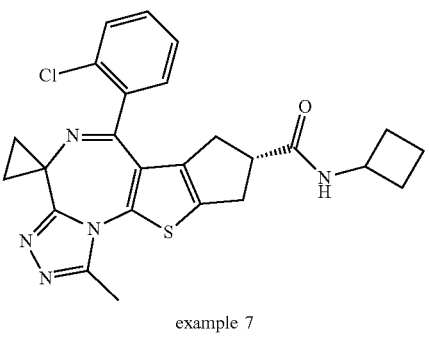
example 7
2.0 nM*
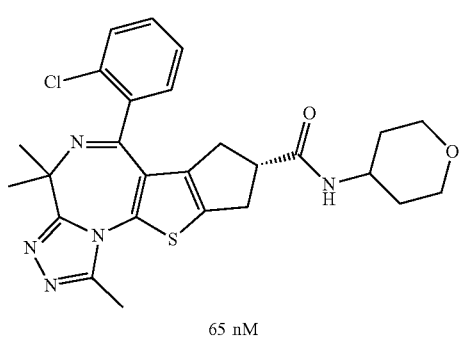
65 nM
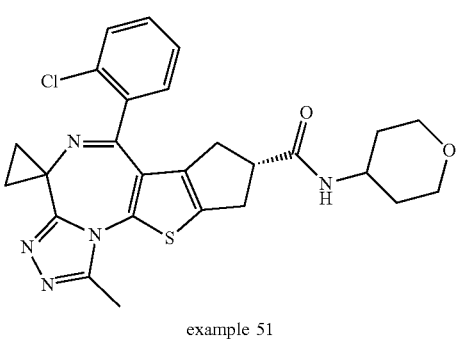
example 51
9.7 nM*
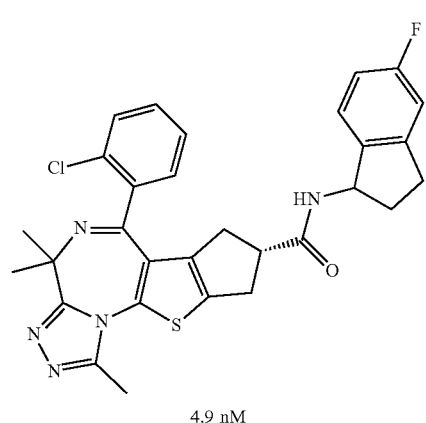
4.9 nM
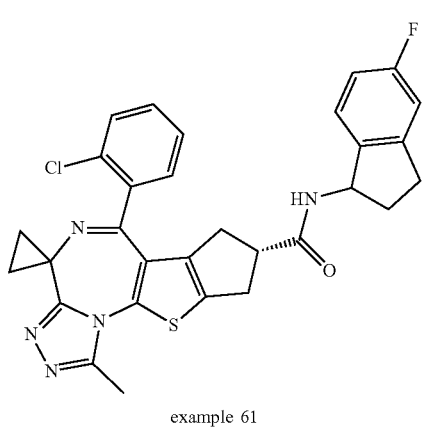
example 61
1.1 nM*
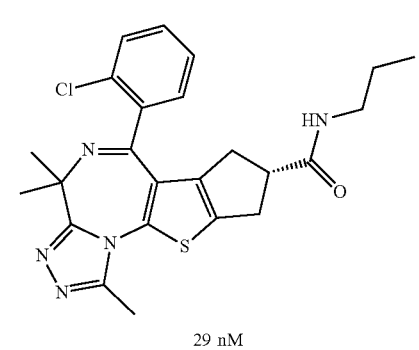
29 nM
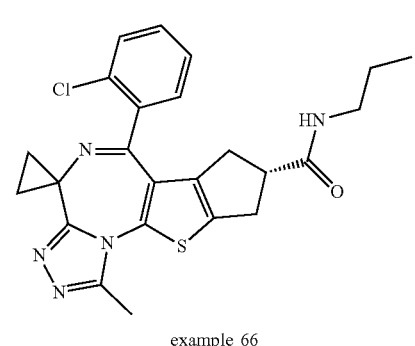
example 66
2.3 nM*

IC$_{50}$
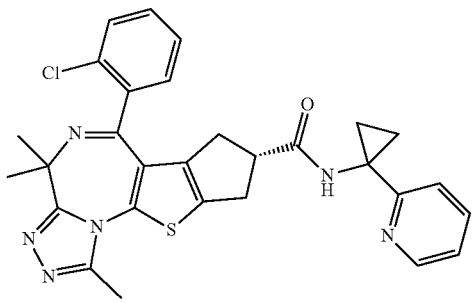 [SMILES: Cc1nnc2n1-c1sc3c(c1C(c1ccccc1Cl)=NC2(C)C)C[C@H](C(=O)NC1(c2ccccn2)CC1)C3]
26 nM
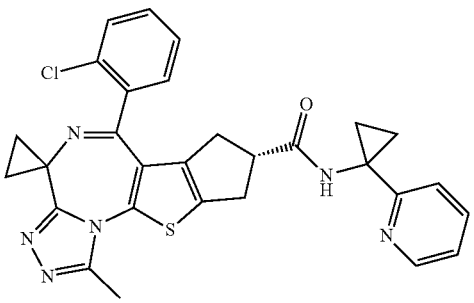 [SMILES: Cc1nnc2n1-c1sc3c(c1C(c1ccccc1Cl)=NC21CC1)C[C@H](C(=O)NC1(c2ccccn2)CC1)C3]
example 87
5.6 nM*
IC$_{50}$
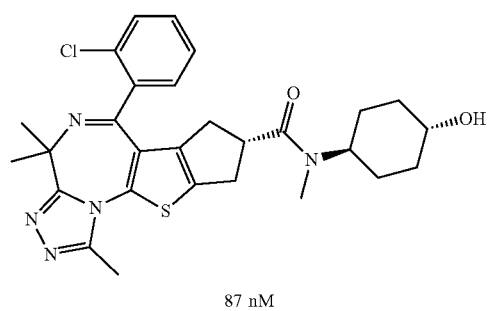
87 nM
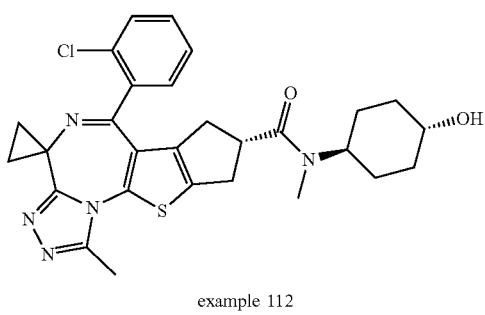
example 112
11.9 nM*
IC$_{50}$
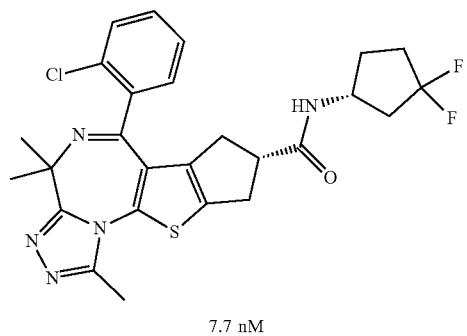
7.7 nM
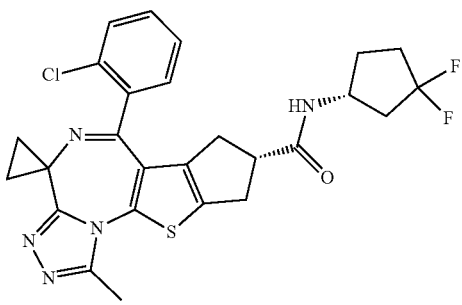 [SMILES: Cc1nnc2n1-c1sc3c(c1C(c1ccccc1Cl)=NC21CC1)C[C@H](C(=O)N[C@@H]1CCC(F)(F)C1)C3]
example 124
2.6 nM*
IC$_{50}$
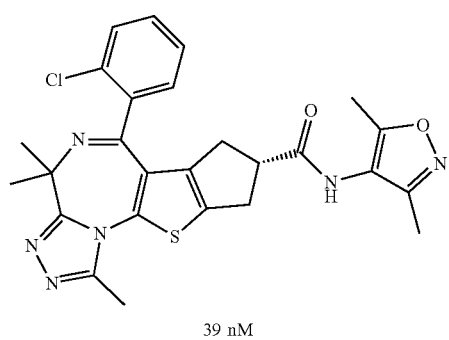
39 nM
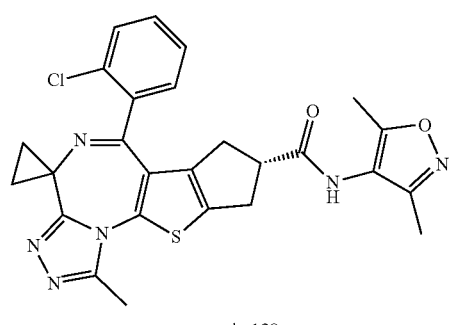
example 128
5.5 nM*

| IC$_{50}$ | |
|---|---|
| 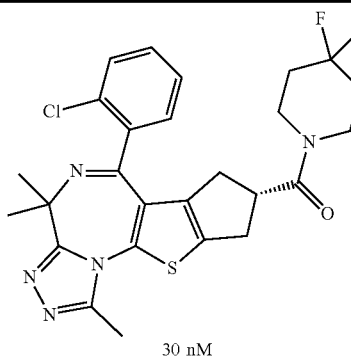 | 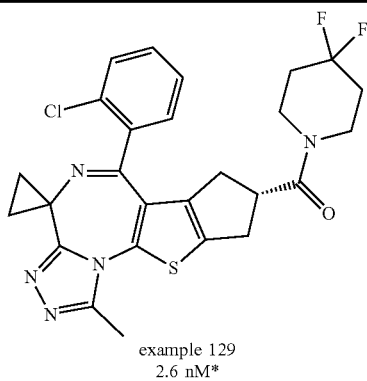 |
| 30 nM | example 129<br>2.6 nM* |

*result from a dedicated head-to-head comparison assay run (thus slightly different from the data reported in Table 2)

Evaluation of the In Vivo Efficacy in an Animal Model of Laser-Induced Choroidal Neovascularization in Brown Norway Rats Male Brown Norway rats (BN/Crl) with a body weight between 160 g and 180 g are obtained from Charles River Labs (Sulzfeld, Germany). Animals are kept in group housing with a 12 h/12 h light/dark cycle (lights on at 6 AM) and accustomed for one week before start of the study. They have free access to a standard chow (Provimi Kliba No. 3438) and tap water. Animals are administered test compounds by once daily oral gavage for 2 weeks.

Under anaesthesia, animals are placed on day 1 in front of a fundus camera to position the optic nerve in the center of the image. Laser treatment is performed with a green Argon laser (Merilas) of 532 nm wavelength using a Micron IV system (Phoenix Research Laboratories, Pleasanton, CA). The diameter of the laser beam is matched with the diameter of the optic nerve and laser pulses with an energy of 400 mW and a duration of 150 msec are used to generate 4 lesions per eye. Lesions are placed between the large blood vessels with a distance from the optic nerve of about twice its diameter. A successful disruption of Bruch's membrane is recognized by the formation of bubbles immediately after the laser beam and confirmed by OCT (optical coherence tomography) scan.

Animals are sacrificed 14 days after laser treatment by cervical dislocation under anaesthesia. Eyes are enucleated and cut along the Ora serrata. Cornea, iris, lens, vitreous and retina are removed and the remaining eye cup (consisting of RPE, choroidea and sclera) is fixed in PFA (4%) for 1 h at 4° C. and then transferred to PBS containing 0.1% Triton X-100 for 1 h at 4° C. The eye cup is stained overnight in the dark at room temperature with FITC-labelled isolectin B4 (10 μg/ml in saline; obtained from Sigma Aldrich, catalogue no. L9381) and washed 3 times with PBS. The eye cup is transferred to a glass slide and cut four times to achieve a flat cloverleaf-like structure. The tissue is covered with mounting medium (Vectashield H-1200 containing DAPI) and a coverslip is put on top to obtain a RPE/choroidea/sclera flatmount (RPE side up). Flatmounts are stored at 4° C. in the dark until analysis.

The samples are analyzed at a wavelength of 488 nm with a LSM 700 confocal laser scanning-microscope (Carl Zeiss, Jena; gain 650, laser strength 2%) and images of the lesions are obtained. Measurement of the lesion size is done with Zen Blue software. The efficacy read-out is the lesion size as stained by isolectin B4 in RPE-choroidea flatmounts.

Evaluation of Binding of Compounds to Melanin

The ability of the compounds to bind to melanin is determined using an in vitro assay with melanin from Sepia officinalis (Sigma-Aldrich, Cat. no.: M2649) in an assay buffer (Phosphate buffer, pH 6.5, 0.9% (w/v) NaCl). To measure the binding, a 1 mg/mL (w/v) melanin suspension and a 0.1% (w/v) BSA solution (control buffer) are prepared in the assay buffer. The compound is incubated on a microtiter plate with the 1 mg/mL melanin suspension (for free compound concentration determination) and without melanin in the control buffer (for total compound concentration determination) at a final compound concentration of 1 μM (compounds are added to the plate in DMSO:assay buffer (40:60); final DMSO concentration is 1%). The plate is incubated for 2 h at 37° C. with 900 rpm orbital shaking. After the incubation, the plate is centrifuged to pellet the melanin and the bound compound. A sample is taken of the supernatants of both melanin and control wells and the concentrations measured with LC-MS. The bound concentration is calculated by subtracting the free compound concentration from the total compound concentration.

Evaluation of Chemical Stability

Within solution state stability studies the influence of temperature, pH and light exposure are analyzed. Stress conditions are applied in order to get a fast signal of possible chemical decomposition via hydrolytical, oxidative or photodegradative pathways.

Typical conditions are:
- 3 d @ 40 or 60° C. in aqueous 0.1 N HCl
- 3 d @ 40 or 60° C. in aqueous buffer pH 2.2
- 3 d @ 40 or 60° C. in aqueous buffer pH 4.0
- 3 d @ 40 or 60° C. in aqueous buffer pH 6.0
- 3 d @ 40 or 60° C. in aqueous buffer pH 7.4
- 3 d @ 40 or 60° C. in aqueous buffer pH 10.0
- 3 d @ 40 or 60° C. in aqueous 0.1 N NaOH
- 3 d @ room temperature in 0.3% $H_2O_2$-solution, intrinsic pH
- 24 h UV-radiation (wavelength: 300-800 nm, power: 200 W/m$^2$) of a solution in water, intrinsic pH using the Suntest CPS+ system from Atlas In case of compounds with poor solubility in aqueous media, addition of an organic cosolvent (typically acetonitrile up to 50 vol-%) is possible.

The stressed/stored samples are analysed by a stability indicative chiral or achiral HPLC-method, as appropriate.

Degradation studies are used to simulate chemical stability of compounds in the acidic part of the gastrointestinal tract. The compounds of the invention show high chemical stability in acidic aqueous media (pH value ca. 1.2) what makes their application as medical drugs to treat human diseases less restricted and troublesome.

The chemical stability of the compounds of the invention at pH value of ca. 1.2 is determined as follows: Compound is dissolved in an HPLC vial in a mixture of acetonitrile/0.1 M aqueous HCl (ratio: 2:3; pH ca. 1.2) to get a concentration of approximately 0.25 mg/ml. The vial is then transferred into an HPLC autosampler system and maintained at the desired temperature of, e.g., 40° C. A first sample is taken and injected immediately into a standard HPLC system with a UV DAD detector. A further sample is injected after 24 hours. Amount of degraded compound is measured by determining the recovery rate of compound [%] for the 24 h injection using an HPLC standard gradient method. Therefore the peak area of the main peak for the first injection ($AU_{t0}$) is determined and set as 100%. Peak area of the main peak is determined also for the 24 h injection ($AU_{24\,h}$) and expressed as fraction of ($AU_{24\,h}$)/($AU_{t0}$)[%]. Analogously, the amount of degraded compound is determined for stability examinations running for more than 1 day, e.g., for 3 days.

Exemplary compounds according to the invention were tested for chemical stability under acidic conditions following a procedure analogous to that described above. For all of them, the amount of degraded compound was found to be not more than 5%.

The following table shows the extent of degradation of representative compounds of the present invention. The number of the respective compound corresponds to the number of the Example in the experimental section.

TABLE 3

| Example | Amount of degradation after 3 d at 40° C. in ACN/0.1M aq. HCl |
|---|---|
| 104 | 1.5% |
| 114 | 4% |
| 124 | 2.5% |

In addition, analogues of the compounds according to the invention that contain a chirally monosubstituted instead of a cyclopropylene substituted 7-membered ring have been observed to partially epimerize at the chiral carbon atom of the 7-membered ring under basic storage conditions (3 d @ 40° C. in aqueous 0.1 N NaOH). Such isomerization, however, is not only undesirable from a general quality perspective, but is associated in particular with a significant drop in binding affinity (see the potency findings above).

In contrast, the compounds according to the invention comprise an achirally substituted 7-membered ring such that epimerization of this moiety cannot occur and detrimental effects of such epimerization are avoided.

Evaluation of Permeability

Caco-2 cells ($1\text{-}2 \times 10^5$ cells/1 cm$^2$ area) are seeded on filter inserts (Costar transwell polycarbonate or PET filters, 0.4 μm pore size) and cultured (DMEM) for 10 to 25 days.

Compounds are dissolved in appropriate solvent (like DMSO, 1-20 mM stock solutions). Stock solutions are diluted with HTP-4 buffer (128.13 mM NaCl, 5.36 mM KCl, 1 mM MgSO$_4$, 1.8 mM CaCl$_2$, 4.17 mM NaHCO$_3$, 1.19 mM Na$_2$HPO$_4$×7H$_2$O, 0.41 mM NaH$_2$PO$_4$xH$_2$O, 15 mM HEPES, 20 mM glucose, pH 7.2) to prepare the transport solutions (0.1-300 μM compound, final DMSO<=0.5%). The transport solution (TL) is applied to the apical or basolateral donor side for measuring A-B or B-A permeability (3 filter replicates), respectively. The receiver side contains HTP-4 buffer supplemented with 2% BSA. Samples are collected at the start and end of experiment from the donor and at various time intervals for up to 2 hours also from the receiver side for concentration measurement by HPLC-MS/MS or scintillation counting. Sampled receiver volumes are replaced with fresh receiver solution.

Evaluation of Metabolic Stability in Human or Rat Liver Microsomes

The metabolic degradation of the test compound is assayed at 37° C. with pooled human or rat liver microsomes. The final incubation volume of 100 μl per time point contains TRIS buffer pH 7.6 at rt (0.1 M), magnesium chloride (5 mM), microsomal protein (1 mg/mL) and the test compound at a final concentration of 1 μM.

Following a short preincubation period at 37° C., the reactions are initiated by addition of beta-nicotinamide adenine dinucleotide phosphate, reduced form (NADPH, 1 mM) and terminated by transferring an aliquot into solvent after different time points. Additionally, the NADPH-independent degradation is monitored in incubations without NADPH, terminated at the last time point. The quenched incubations are pelleted by centrifugation (10000 g, 5 min). An aliquot of the supernatant is assayed by LC-MS/MS for the amount of parent compound. The half-life (t½ INVITRO) is determined by the slope of the semilogarithmic plot of the concentration-time profile.

Evaluation of Metabolic Stability in Human or Rat Hepatocytes

The metabolic degradation of the test compound is assayed in a hepatocyte suspension. Hepatocytes (typically cryopreserved) are incubated in an appropriate buffer system (e.g., Dulbecco's modified eagle medium plus 3.5 μg glucagon/500 mL, 2.5 mg insulin/500 mL and 3.75 mg/500 mL hydrocortison) containing 5% species serum.

Following a (typically) 30 min preincubation in an incubator (37° C., 10% CO$_2$) 5 μL of test compound solution (80 μM; from 2 mM in DMSO stock solution diluted 1:25 with medium) are added into 395 μL hepatocyte suspension (cell density in the range 0.25-5 Mio cells/mL, typically 1 Mio cells/mL; final concentration of test compound 1 μM, final DMSO concentration 0.05%).

The cells are incubated for six hours (incubator, orbital shaker) and samples (25 μL) are taken at 0, 0.5, 1, 2, 4 and 6 h. Samples are transferred into ACN and pelleted by centrifugation (5 min). The supernatant is transferred to a new 96-deepwell plate, evaporated under nitrogen and resuspended.

Decline of parent compound is analyzed by HPLC-MS/MS CLint is calculated as follows CL_INTRINSIC=Dose/AUC=(C0/CD)/(AUD+clast/k)×1000/60. C0: initial concentration in the incubation [μM], CD: cell density of vital cells [10e6 cells/mL], AUD: area under the data [μM×h], clast: concentration of last data point [μM], k: slope of the regression line for parent decline [h−1].

Reaction Phenotyping Assay

A phenotyping assay is performed to identify the metabolic enzymes responsible for metabolic conversion of a test compound.

The metabolic degradation of the test compound and the assessment of formation of metabolites is performed using Supersomes (human CYP expressed in baculovirus infected insect cells). Compounds are tested for their substrate affinities towards CYP isoenzymes 1A1, 1A2, 2B6, 2C8, 2C9, 2C19, 2D6, 2J2, 3A4, 3A5 and FM03.

Incubations in TRIS buffer (0.1 M, pH 7.6, supplemented with 5 mM magnesium chloride) consist of 200 pmol/mL of the respective Supersomal protein and 10 µM test compound.

Following a short preincubation period of 15 min at 37° C., the reaction is initiated by addition of beta-nicotinamide adenine dinucleotide phosphate, reduced form (NADPH, 1 mM).

After 60 min at 37° C., the incubations are terminated by transferring an aliquot of sample into acetonitrile. Samples are analyzed for formation of metabolites by means of HPLC-MS/MS.

In parallel, the metabolic degradation of the test compound and the assessment of formation of metabolites are performed using human hepatocytes. After recovery from cryopreservation, human hepatocytes are diluted in Dulbecco's modified eagle medium (supplemented with 3.5 µg glucagon/500 mL, 2.5 mg insulin/500 mL, 3.75 mg hydrocortison/500 mL, and 5% human serum) to obtain a final cell density of $1.0 \times 10^6$ cells/mL or $4.0 \times 10^6$ cells/mL, depending on the metabolic turnover rate of the test compound. Following a 30 min preincubation in a cell culture incubator (37° C., 10% $CO_2$), test compound solution is spiked into the hepatocyte suspension to give a final test compound concentration of 10 µM and a final DMSO concentration of 0.05%.

The cell suspension is incubated at 37° C. (cell culture incubator, horizontal shaker). At the end of the incubation time (max. 6 h), samples are quenched with acetonitrile (containing internal standard) and pelleted by centrifugation. The supernatant is transferred to a 96-deepwell plate, and prepared for analysis of decline of parent compound by HPLC-MS/MS.

The fraction metabolized (fm) for each CYP isoenzyme is calculated, considering the formation of each metabolite in human hepatocytes in vitro and the relative abundance of the respective enzyme in the liver based on scaling factors according to Yeo et al. (Br. J. Clin. Pharmacol. 2004, 57, 687-688).

Evaluation of Plasma Protein Binding

This equilibrium dialysis (ED) technique is used to determine the approximate in vitro fractional binding of test compounds to plasma proteins. Dianorm Teflon dialysis cells (micro 0.2) are used. Each cell consists of a donor and an acceptor chamber, separated by an ultrathin semipermeable membrane with a 5 kDa molecular weight cutoff. Stock solutions for each test compound are prepared in DMSO at 1 mM and diluted to a final concentration of 1.0 µM. The subsequent dialysis solutions are prepared in pooled human or rat plasma (with NaEDTA) from male and female donors. Aliquots of 200 µl dialysis buffer (100 mM potassium phosphate, pH 7.4) are dispensed into the buffer chamber. Aliquots of 200 µL test compound dialysis solution are dispensed into the plasma chambers. Incubation is carried out for 2 hours under rotation at 37° C.

At the end of the dialysis period, the dialysate is transferred into reaction tubes. The tubes for the buffer fraction contain 0.2 mL ACN/water (80/20). Aliquots of 25 µl of the plasma dialysate are transferred into deep well plates and mixed with 25 µl ACN/water (80/20), 25 µL buffer, 25 µL calibration solution and 25 µl Internal Standard solution. Protein precipitation is done by adding 200 µL ACN.

Aliquots of 50 µL of the buffer dialysate are transferred into deep well plates and mixed with 25 µl blank plasma, 25 µl Internal Standard solution and 200 µL ACN.

Samples are measured on HPLC-MS/MS-Systems and evaluated with Analyst-Software.

Percent bound is calculated with the formula: % bound=(plasma concentration−buffer concentration/plasma concentration)×100

Evaluation of Solubility

The aqueous solubility of the test compound is determined by comparing the amount dissolved in buffer to the amount in an ACN/water (1/1) solution. Starting from a 10 mM DMSO stock solution aliquots are diluted with ACN/water (1/1) or buffer, respectively. After 24 h of shaking, the solutions are filtrated and analyzed by LC-UV. The amount dissolved in buffer is compared to the amount in the ACN solution.

Solubility will usually be measured from 0.001 to 0.125 mg/mL at a DMSO concentration of 2.5%. If more than 90% of the compound is dissolved in buffer, the value is marked with ">".

Evaluation of Pharmacokinetic Characteristics in Rodents

The test compound is administered either intravenously to fed rats or orally to fasted rats. Blood samples are taken at several time points post application of the test compound, anticoagulated and centrifuged.

The concentrations of analytes—the administered compound and/or metabolites—are quantified in the plasma samples by LC-MS/MS. To determine the renal clearance urine samples are collected over 24 hours after intravenous administration and the urine concentration of the administered compound is quantified by LC-MS/MS.

PK parameters are calculated using non-compartmental PK analysis (NCA). The trapezoidal rule is applied (lin up-log down) to determine the individual area under the curve from time zero to the last measured concentration ($AUC_{0-tz}$). The $AUC_{0-inf}$ is calculated by extrapolating the terminal phase and adding the $AUC_{tz-\infty}$, to the $AUC_{0-tz}$. The individual CL value is calculated according to equation 1.

$$CL_{tot}\left[\frac{mL}{min*kg}\right] = \frac{Dose\left[\frac{nmol}{kg}\right]}{AUC_{0-inf}\left[\frac{nmol}{L}*h\right]} * 1000\left[\frac{mL}{L}\right] \quad \text{(Equation 1)}$$

where $CL_{tot}$ is the total clearance (renal+non-renal), Dose is the administered dose, $AUC_{0-Inf}$ is the calculated area under the curve, and 1000 represents the factor to provide the clearance in mL/min/kg, which is the unit commonly reported in literature.

In a second step, the drug-specific renal clearance for each animal is calculated using equation 2.

$$CL_{ren}\left[\frac{mL}{min*kg}\right] = CL_{tot}\left[\frac{mL}{min*kg}\right] * A_{e,urine} \quad \text{(Equation 2)}$$

where $CL_{ren}$ is the renal clearance and $A_{e,urine}$ is the fraction of the dose excreted into urine over 24 hours after i.v. drug administration.

Evaluation of Cytotoxicity

Human Liver Microtissues (hLIMTs—3D) 14 Day Repeat Dose Assay: Cellular ATP content Experimental Procedure.

Co-cultured hLIMTs are obtained by InSphero. They are formed by seeding cryopreserved human hepatocytes and cryopreserved human non-parenchymal cells into 96-well spheroid plates in liver microtissue media. Cells are incubated at 37° C., 5% $CO_2$ until microtissue formation and then compound treated. Test compound is diluted in vehicle (DMSO) and dilutions are made in 0.5% vehicle in liver microtissue media. Test compounds at 8 concentrations in triplicates or quadruplicates are then incubated for 14 days with regular re-dosing of compound. Chlorpromazine and/or other known cytotoxicants are used as positive controls. At the end of the incubation period cellular ATP content is measured using CellTiter-Glo® (Promega).

Data Analysis.

The vehicle control wells are used to determine the normal ATP content that is then set to 100%. The ratio to control is calculated for each compound concentration. A 4-parameter non-linear curve fitting is used to describe a dose response curve. The $EC_{50}$ is calculated from the dose response curve. In addition, vehicle control wells are used to determine the lower significance limit. The intersection of the dose response curve with the lower significance limit determines the lowest effective concentration (LEC)*. The lowest tested concentration that exceeds the lower significance limit (Mean and standard deviation outside lower limit) is determined as the first effective concentration (FEC)**.

*LEC=calculated lowest effective concentration from intersection of lower or higher significance limit and dose response curve
**FEC=first effective concentration below the lower significance limit (including standard deviation)

Methods of Treatment

In another aspect of the present invention, it is described that compounds of formula (I) or pharmaceutically acceptable salts thereof possess suitable properties for use in therapy, i.e., for use as medicaments. In particular, compounds of formula (I) or pharmaceutically acceptable salts thereof, as well as pharmaceutical compositions containing the same, may be useful for the treatment of diseases or conditions, which can be influenced by antagonizing the platelet activating factor receptor (PAFR), e.g., which are mediated by unwanted activity of PAFR or in which antagonism of PAFR is beneficial, in a patient.

Diseases and conditions which can be influenced by antagonizing PAFR, e.g., which are mediated by unwanted PAFR activity or in which antagonism of the activity of PAFR are beneficial, encompass ocular diseases, cardiovascular diseases, cancer, neurological and neurodegenerative disorders, renal disorders, liver diseases, and allergies. These disorders include but are not limited to retinopathy or diabetic retinopathy, proliferative and non-proliferative retinopathy, diabetic macular ischemia (DMI), geographic atrophy, Stargardt disease, retinal degeneration in glaucoma, myopic macular degeneration, chronic pan uveitis, retinitis pigmentosa, retinal vein occlusion (such as central, branch or hemiretinal vein occlusion), diabetic macular edema (DME), clinically significant macular edema (CSME), cystoid macular edema (CME), CME following cataract extraction, CME induced by cryotherapy, CME induced by uveitis, endophthalmitis, CME following vascular occlusion (e.g., central retina vein occlusion, branch retinal vein occlusion, or hemiretinal vein occlusion), retinal edema, complications related to cataract surgery in diabetic retinopathy, hypertensive retinopathy, retinal trauma, dry and wet age-related macular degeneration (AMD), polypoidal choroidal vasculopathy (PCV), choroidal neovascularization (CNV; e.g., non-exudative choroidal neovascularization), subretinal fibrosis (e.g., associated with non-exudative or exudative choroidal neovascularization), posterior vitreous detachment (PVD), ischemic reperfusion injuries, e.g., in all kind of contexts associated with tissue and/or organ transplantation, surgically-induced brain injury, focal cerebral ischemia, global cerebral ischemia, glioma-associated edema, spinal cord injury, pain, ischemia, focal brain ischemia, neurological and cognitive deficits, deep vein thrombosis, stroke, myocardial infarction, atherosclerosis, acquired angioedema, hereditary angioedema (HAE), drug-related (ACE-inhibitors) edema, high altitude cerebral edema, cytotoxic cerebral edema, osmotic cerebral edema, obstructive hydrocephalus, radiation induced edema, lymph edema, traumatic brain injury, hemorrhagic stroke (e.g., cerebral stroke or subarachnoid stroke), intracerebral hemorrhage, hemorrhagic transformation of ischemic stroke, cerebral trauma associated with injury or surgery, encephalomyelitis, amyotrophic lateral sclerosis, neuropathic pain, brain aneurysm, arterio-venous malformation, reduction of blood losses during surgical procedures (e.g., cardiothoracic surgery, such as cardiopulmonary bypass or coronary artery bypass grafting), blood coagulation disorders such as thrombosis, itch, disorders with an inflammation component (such as multiple sclerosis), epilepsy, encephalitis, Alzheimer's disease, excessive daytime sleepiness, essential hypertension, increased blood pressure associated with diabetes or hyperlipidemia, renal insufficiency, renal disorders including chronic kidney disease, interstitial cystitis/bladder pain syndrome, heart failure, microalbuminuria, albuminuria, proteinuria, disorders associated with increased vascular permeability (e.g., increased retinal vascular permeability, increased leg, feet, ankle vascular permeability), cerebral hemorrhage, deep vein thrombosis, coagulation from post fibrinolytic treatments, angina, angioedema, sepsis, arthritis (e.g., rheumatoid arthritis, osteoarthritis, infection arthritis), ulcerative colitis, pancreatitis, lupus, gout, psoriasis, inflammatory bowel, diabetes, diabetic complications, complications arising from metabolic syndrome, non-alcoholic steatohepatitis (NASH), allergies, bacterial and viral infectious diseases including HIV infection, anaphylaxis, sepsis, chronic obstructive pulmonary disease (COPD), asthma, periodontitis, psoriasis, urticaria, UVB-induced dermatitis, astrocyte-activation related diseases (e.g., Alzheimer's disease or multiple sclerosis), Parkinson's disease, amyotrophic lateral sclerosis, Creutzfeld-Jacob disease, stroke, epilepsy and trauma (e.g., brain trauma), allergic edema, e.g., airflow obstruction in chronic allergic sinusitis or perennial rhinitis; airflow obstruction in acute asthma; serositis associated with systemic lupus erythematosus (SLE), acute respiratory distress syndrome (ARDS), cancer (such as breast cancer, colorectal cancer, oesophagal cancer, lung cancer, liver cancer, pancreatic cancer, skin cancer including melanoma, cervical cancer), and other diseases.

Thus, the compounds and pharmaceutical compositions according to the invention are particularly suitable for the treatment of ocular diseases including diabetic retinopathy, proliferative and non-proliferative retinopathy, diabetic macular edema (DME), retinal vein occlusion, dry and wet age-related macular degeneration (AMD), geographic atrophy, polypoidal choroidal vasculopathy (PCV), and choroidal neovascularization (CNV; e.g., non-exudative choroidal neovascularization).

In addition, the compounds and pharmaceutical compositions according to the invention are particularly suitable for the treatment of allergies and inflammation-related conditions and diseases, such as urticaria and NASH.

The compounds and pharmaceutical compositions according to the invention are most particularly suitable for the treatment of diabetic macular edema (DME), dry and wet age-related macular degeneration (AMD), geographic atrophy, non-exudative choroidal neovascularization (CNV), urticaria, and NASH.

The dose range of the compounds of formula (I) applicable per day is usually from 0.01 to 10 mg per kg body weight. The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon the patient's unique condition.

The compounds and compositions, including any combinations with one or more additional therapeutic agents, according to the invention may be administered by oral, intravitreal, transdermal, inhalative, parenteral, or sublingual route. Of the possible methods of administration, oral or intravitreal administration are preferred, in particular oral administration. In the case of intravitreal injection the preferred dose should not exceed 5 mg per eye.

The patient to be treated is preferably a mammal, most preferably a human patient.

Thus, in another aspect, the present invention provides a compound of formula (I), including pharmaceutically acceptable salts thereof, for use as a medicament.

In another aspect, the present invention provides a method for the treatment of a disease or condition, which is mediated by unwanted platelet activating factor receptor activity or in which antagonism of platelet activating factor receptor is beneficial, in a patient in need thereof.

Likewise, the present invention provides a compound of formula (I) or a pharmaceutically acceptable salt thereof for use in a method for the treatment of a disease or condition, which is mediated by unwanted platelet activating factor receptor activity or in which antagonism of platelet activating factor receptor is beneficial, in a patient in need thereof.

Likewise, the present invention provides the use of a compound of formula (I) or a pharmaceutically acceptable salt thereof, in the manufacture of a medicament for use in a method for the treatment of a disease or condition, which is mediated by unwanted platelet activating factor receptor activity or in which antagonism of platelet activating factor receptor is beneficial, in a patient in need thereof.

Likewise, the present invention provides the use of a compound of formula (I) or a pharmaceutically acceptable salt thereof, in a method for the treatment of a disease or condition, which is mediated by unwanted platelet activating factor receptor activity or in which antagonism of platelet activating factor receptor is beneficial, in a patient in need thereof.

According to one embodiment, the method for the treatment comprises administering to the patient one or more compounds of formula (I) or pharmaceutically acceptable salts thereof, preferably administering to the patient a therapeutically effective amount of one or more compounds of formula (I) or pharmaceutically acceptable salts thereof.

According to another embodiment, the method for the treatment comprises administering to the patient a pharmaceutical composition according to the present invention.

According to one embodiment, the disease or condition, which is mediated by unwanted platelet activating factor receptor activity or in which antagonism of platelet activating factor receptor is beneficial, is selected from ophthalmic indications such as diabetic retinopathy, proliferative and non-proliferative retinopathy, diabetic macular edema (DME), retinal vein occlusion, dry and wet age-related macular degeneration (AMD), geographic atrophy, polypoidal choroidal vasculopathy (PCV), and choroidal neovascularization (CNV).

According to another embodiment, the disease or condition, which is mediated by unwanted platelet activating factor receptor activity or in which antagonism of platelet activating factor receptor is beneficial, is selected from allergies and inflammation-related conditions and diseases, such as urticaria and NASH.

According to another embodiment, the disease or condition, which is mediated by unwanted platelet activating factor receptor activity or in which antagonism of platelet activating factor receptor is beneficial, is selected from diabetic complications associated with diabetic retinopathy such as diabetic macular edema, diabetic macular ischemia, and proliferative diabetic retinopathy.

According to one embodiment, the patient is a human patient.

Pharmaceutical Compositions

In another aspect of the present invention, it is described that a compound of the invention or a pharmaceutically acceptable salt thereof may be used as active ingredients in pharmaceutical compositions.

Suitable preparations for administering the compounds of the invention, optionally in combination with one or more further therapeutic agents, will be apparent to those with ordinary skill in the art and include for example tablets, pills, capsules, suppositories, lozenges, troches, solutions, syrups, elixirs, sachets, injectables, inhalables, powders, etc. Oral formulations, particularly solid forms such as, e.g., tablets or capsules are preferred. For intravitreal injection, solutions are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders, and/or lubricants. The tablets may also consist of several layers. The particular excipients, carriers and/or diluents that are suitable for the desired preparations will be familiar to the skilled person on the basis of his specialist knowledge. The preferred ones are those that are suitable for the particular formulation and method of administration that are desired. The preparations or formulations according to the invention may be prepared using methods known per se that are familiar to the skilled person, such as for example by mixing or combining at least one compound of formula (I) according to the invention or a pharmaceutically acceptable salt of such a compound, and one or more excipients, carriers, and/or diluents.

Thus, according to another aspect of the present invention, pharmaceutical compositions comprising one or more compounds of formula (I), or pharmaceutically acceptable salts thereof, optionally together with one or more inert carriers and/or diluents are provided.

Also, a pharmaceutical composition that comprises one or more of the above-mentioned compounds, or pharmaceutically acceptable salts thereof, optionally together with one or more inert carriers and/or diluents is provided for use in a method for the treatment of diseases or conditions which are mediated by unwanted PAFR activity or in which antagonism of PAFR is beneficial, in a patient in need thereof.

In particular, the invention provides a pharmaceutical composition according to this invention for use in a method for the treatment of ophthalmic indications such as diabetic retinopathy, proliferative and non-proliferative retinopathy, diabetic macular edema (DME), retinal vein occlusion, dry and wet age-related macular degeneration (AMD), geographic atrophy, polypoidal choroidal vasculopathy (PCV), and choroidal neovascularization (CNV; e.g., non-exudative choroidal neovascularization), and of allergies and inflammation-related conditions and diseases, such as urticaria and NASH.

Furthermore, the present invention relates to the use of a pharmaceutical composition according to this invention for the treatment of diseases or conditions which are mediated by unwanted PAFR activity in a patient, preferably in a human.

Also, the present invention relates to the use of a pharmaceutical composition according to this invention for the treatment of diseases or conditions in which antagonism of PAFR is beneficial in a patient, preferably in a human.

According to one embodiment, a pharmaceutical composition comprising one or more compounds of formula (I) or pharmaceutically acceptable salts thereof, and one or more additional therapeutic agents, optionally together with one or more inert carriers and/or diluents is provided.

For instance, this composition comprises one compound of formula (I) or a pharmaceutically acceptable salt thereof and one or more additional therapeutic agents.

Combination Therapy

The compounds of the invention may further be combined with one or more, preferably one additional therapeutic agent.

According to one embodiment the additional therapeutic agent is selected from the group of therapeutic agents useful in the treatment of diseases or conditions described hereinbefore, in particular of ocular diseases, allergies, and inflammation-related conditions and diseases, such as diabetic macular edema (DME), dry and wet age-related macular degeneration (AMD), geographic atrophy, non-exudative choroidal neovascularization (CNV), urticaria and NASH, or of metabolic diseases or conditions such as for example diabetes mellitus, obesity, diabetic complications, hypertension, and hyperlipidemia.

Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity, agents for the treatment of high blood pressure, heart failure and/or atherosclerosis, agents for the treatment of ocular diseases and agents for the treatment of allergies and inflammation-related conditions and diseases.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, dual agonists comprising GLP-1 activity together with glucagon or GIP activity, cycloset, 11β-HSD inhibitors. Other suitable combination partners are inhibitors of protein tyrosinephosphatase 1, substances that affect deregulated glucose production in the liver, such as, e.g., inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, β3-agonists, leptin or leptin mimetics, agonists of the 5HT2c receptor, dual agonists of the GLP-1 and glucagon receptor.

Therapeutic agents for the treatment of high blood pressure, chronic heart failure and/or atherosclerosis are for example A-II antagonists or ACE inhibitors, ECE inhibitors, diuretics, p-blockers, Ca-antagonists, centrally acting antihypertensives, antagonists of the alpha-2-adrenergic receptor, inhibitors of neutral endopeptidase, thrombocyte activating inhibitors and others or combinations thereof are suitable. Angiotensin II receptor antagonists are preferably used for the treatment or prevention of high blood pressure and complications of diabetes, often combined with a diuretic such as hydrochlorothiazide.

Therapeutic agents for the treatment of ocular diseases may include for example intravitreally administered corticosteroids, intravitreally administered anti-VEGF therapy, anti-Ang2 inhibitors, dual anti-VEGF/anti-Ang2 inhibitors, anti PDGF, dual anti-VEGF/anti-PDGF, VAP-1 (AOC3) inhibitors, Complement inhibitors (e.g., Complement factors 3, 5, B, and D inhibitors), Bradykinin receptor 1 antagonists, CCR-2 antagonists, PKK inhibitors.

Additional treatments for ocular diseases may include laser coagulation therapy.

Therapeutic agents for the treatment of urticaria may include for example antihistamines, steroids such as cortisone, epinephrine, antibodies against immunoglobulin E, immunosuppressants such as cyclosporin A, and leukotriene receptor antagonists.

Therapeutic agents for the treatment of NASH may include for example FXR agonists, FXR/TGR5 agonists, THR-ß agonists, ACC inhibitors, TGF-b1 antagonists, LTA4 hydrolase inhibitors, SGLT inhibitors, activin type 2 receptor antagonists, NLRP3 inhibitors, avß1 integrin inhibitors, cGAS/STING inhibitors, GLP-1R agonists, FGF21 agonists, GLP-1/glucagon receptor dual agonists, GLP-1/GIP receptor dual agonists, GLP-1/FGF21 receptor dual agonists, GLP-1/GIP/glucagon receptor triple agonists, AOC3 inhibitors, JNK1 inhibitors, CCR2/5 inhibitors, ACC inhibitors, DGAT inhibitors, KHK inhibitors, PPARα/δ agonists, FGF19 agonists, ß-klotho/FGFR1c agonists, PNPLA3 inhibitors, NLRP3 inhibitors, THR-ß agonists, HSD17 β13 inhibitors, galectin-3 inhibitors, SCD1 inhibitors, ASK1 inhibitors, endothelin receptor A antagonists, FASN inhibitors, calpain inhibitors, autotaxin inhibitors, TREM2 agonists, sGC inhibitors, PKK inhibitors, RORc inhibitors, TLR4 inhibitors, and IL11 inhibitors.

The compounds of the present invention and/or pharmaceutical compositions comprising a compound of the present invention optionally in combination with one or more additional therapeutic agents may be administered in conjunction with exercise and/or a diet.

The dosage for the combination partners mentioned above is usually ⅕ of the lowest dose normally recommended up to 1/1 of the normally recommended dose.

The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Thus, according to another aspect, this invention relates to a pharmaceutical composition which comprises one or more compounds according to the invention and one or more additional therapeutic agents described hereinbefore and hereinafter, optionally together with one or more inert carriers and/or diluents.

According to another aspect, the present invention provides a method for the treatment of a disease or condition, which is mediated by unwanted platelet activating factor receptor activity or in which antagonism of PAFR is beneficial, in a patient in need thereof, the method comprising administering to the patient one or more compounds of formula (I) or pharmaceutically acceptable salts thereof, in combination with one or more additional therapeutic agents described in hereinbefore and hereinafter,
preferably administering to the patient a therapeutically effective amount of one or more compounds of formula (I) or pharmaceutically acceptable salts thereof, in combination with a therapeutically effective amount of one or more additional therapeutic agents described in hereinbefore and hereinafter.

Likewise, the present invention provides a compound of formula (I) or a pharmaceutically acceptable salt thereof in combination with one or more additional therapeutic agents described hereinbefore or hereinafter for use in a method for the treatment of a disease or condition, which is mediated by unwanted PAFR activity or in which antagonism of PAFR is beneficial, in a patient in need thereof.

Likewise, the present invention provides the use of a compound of formula (I) or a pharmaceutically acceptable salt thereof, in combination with one or more additional therapeutic agents described hereinbefore or hereinafter, in the manufacture of a medicament for use in a method for the treatment of a disease or condition, which is mediated by unwanted PAFR activity or in which antagonism of PAFR is beneficial, in a patient in need thereof.

Likewise, the present invention provides the use of a compound of formula (I) or a pharmaceutically acceptable salt thereof, in combination with one or more additional therapeutic agents described hereinbefore or hereinafter, in a method for the treatment of a disease or condition, which is mediated by unwanted PAFR activity or in which antagonism of PAFR is beneficial, in a patient in need thereof.

According to one embodiment, the method for the treatment comprises administering to the patient one or more compounds of formula (I) or pharmaceutically acceptable salts thereof, in combination with one or more additional therapeutic agents described hereinbefore and hereinafter, preferably administering to the patient a therapeutically effective amount of one or more compounds of formula (I) or pharmaceutically acceptable salts thereof, in combination with a therapeutically effective amount of one or more additional therapeutic agents described hereinbefore and hereinafter.

According to another embodiment, the method for the treatment comprises administering to the patient a pharmaceutical composition comprising one or more compounds according to the invention and one or more additional therapeutic agents described hereinbefore and hereinafter, optionally together with one or more inert carriers and/or diluents.

According to one embodiment, the one or more additional therapeutic agents are selected from antidiabetic agents, agents for the treatment of overweight and/or obesity, agents for the treatment of high blood pressure, heart failure and/or atherosclerosis, and agents for the treatment of ocular diseases, in particular from those agents specifically mentioned above.

According to one embodiment, the disease or condition, which is mediated by unwanted PAFR activity or in which antagonism of PAFR is beneficial, is selected from ophthalmic indications such as diabetic retinopathy, proliferative and non-proliferative retinopathy, diabetic macular edema (DME), dry and wet age-related macular degeneration (AMD), geographic atrophy, polypoidal choroidal vasculopathy (PCV) and choroidal neovascularization (CNV), from allergies and inflammation-related conditions and diseases such as urticaria or NASH, and from diabetic complications associated with diabetic retinopathy such as diabetic macular edema, diabetic macular ischemia and proliferative diabetic retinopathy.

According to one embodiment, the patient is a human patient.

Other features and advantages of the present invention will become apparent from the following more detailed Examples which illustrate, by way of example, the principles of the invention.

Examples and Experimental Data

The following examples are for the purpose of illustration of the invention only and are not intended in any way to limit the scope of the present invention.

Abbreviations

Ac acetyl
ACN acetonitrile
ATP adenosine triphosphate
BPR backpressure regulator
BSA bovine serum albumin
d day(s)
DAD diode array detector
DAPI 4',6-diamidino-2-phenylindole
dba dibenzylideneacetone
DCM dichloromethane
dioxane 1,4-dioxane
DIPEA N,N-diisopropylethylamine
DMEM Dulbecco's modified eagle medium
DMF N,N-dimethylformamide
DMSO dimethyl sulfoxide
EDTA ethylenediaminetetraacetate
ESI electrospray ionization (MS)
EtOAc ethyl acetate
EtOH ethanol
FITC fluorescein isothiocyanate
h hour(s)
HPLC high performance liquid chromatography
IPA isopropanol
KHMDS potassium bis(trimethylsilyl)amide
LC liquid chromatography
LC-MS coupled liquid chromatography-mass spectrometry
M molar (mol/L)
MeCN acetonitrile MeOH methanol
min minute(s)
MS mass spectrometry
NMR nuclear magnetic resonance
OAc acetate
PBS phosphate buffered saline
PET polyethylene terephthalate
pet. Petroleum
RPE retinal pigment epithelium
rt room temperature
$t_R$ retention time (HPLC/LC)
sc supercritical
SFC supercritical fluid chromatography
TBTU O-(benzotriazol-1-yl)-N,N,N',N'-tetramethyluronium tetrafluoroborate
TFA trifluoroacetic acid
THF tetrahydrofuran
TLC thin-layer chromatography
Tol-BINAP 2,2'-bis(di-p-tolylphosphino)-1,1'-binaphthyl
UV ultraviolet
XPhos dicyclohexyl[2',4',6'-tris(propan-2-yl)[1,1'-biphenyl]-2-yl]phosphane The terms "ambient temperature" and "room temperature" are used interchangeably and designate a temperature of about 20° C., e.g., 15 to 25° C.

As a rule, 1H-NMR and/or mass spectra have been obtained for the compounds prepared.

Unless otherwise specified, compounds containing chiral centers have the stereochemistry depicted. The assignment of stereochemistry has been made either by use of a chiral starting material of known stereochemistry, by stereoselective synthesis of known stereochemistry, or by biological activity.

Analytical Methods:

| Method: | 1 |
|---|---|
| Device: | Agilent 1200 with DA-and MS-Detector |
| Column: | Sunfire C18, 3 × 30 mm, 2.5 μm |
| Column Supplier: | Waters |

| Gradient/Solvent Time [min] | % Solvent [H$_2$O, 0.1% TFA] | % Solvent [ACN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3.0 | 60 |
| 1.40 | 0 | 100 | 3.0 | 60 |

| Method: | 2 |
|---|---|
| Device: | Agilent 1200 with DA-and MS-Detector |
| Column: | Sunfire C18, 3 × 30 mm, 2.5 μm |
| Column Supplier: | Waters |

| Gradient/Solvent Time [min] | % Solvent [H$_2$O, 0.1% TFA] | % Solvent [ACN] | Flow [mL/min] | Temperature [° C.] |
|---|---|---|---|---|
| 0.00 | 50 | 50 | 2.2 | 60 |
| 0.20 | 50 | 50 | 2.2 | 60 |
| 1.20 | 0 | 100 | 2.2 | 60 |
| 1.25 | 0 | 100 | 3.0 | 60 |
| 1.40 | 0 | 100 | 3.0 | 60 |

| Method: | 3 |
|---|---|
| Device: | Waters Acquity, QDa Detector (MS) |
| Column: | XBridge C18, 3 × 30 mm, 2.5 μm |
| Column Supplier: | Waters |

| Gradient/Solvent Time [min] | % Solvent [H$_2$O, 0.1% NH$_3$] | % Solvent [ACN] | Flow [mL/min] | Temperature [° C.] |
|---|---|---|---|---|
| 0.00 | 95 | 5 | .5 | 60 |
| 1.30 | 0 | 100 | .5 | 60 |
| 1.50 | 0 | 100 | .5 | 60 |
| 1.60 | 95 | 5 | .5 | 60 |

| Method: | 4 |
|---|---|
| Device: | Waters Acquity, QDa Detector (MS) |
| Column: | XBridge C18, 3 × 30 mm, 2.5 μm |
| Column Supplier: | Waters |

| Gradient/Solvent Time [min] | % Solvent [H$_2$O, 0.1% NH$_3$] | % Solvent [ACN] | Flow [mL/min] | Temperature [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |
| 1.60 | 95 | 5 | 1.5 | 60 |

| Method: | 5 |
|---|---|
| Device: | Agilent 1200 with DA-and MS-Detector |
| Column: | XBridge C18, 3 × 30 mm, 2.5 μm |
| Column Supplier: | Waters |

| Gradient/Solvent Time [min] | % Solvent [H₂O, 0.1% TFA] | % Solvent [ACN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3.0 | 60 |
| 1.40 | 0 | 100 | 3.0 | 60 |

Method: 6
Device: Agilent 1260 SFC with DAD and MS
Column: Chiralpak ® IG, 4.6 × 250 mm, 5 μm
Column Supplier: Daicel

| Gradient/Solvent Time [min] | % Solvent [scCO₂] | % Solvent [MeOH, 20 mM NH₃] | Flow [mL/min] | Temperature [°C] | Back Pressure [PSI] |
|---|---|---|---|---|---|
| 0.00 | 60 | 40 | 4.0 | 40 | 2175 |
| 10.0 | 60 | 40 | 4.0 | 40 | 2175 |

Method: 7
Device: Agilent 1260 SFC with DAD and MS
Column: Chiral Art ® Cellulose SB 4.6 × 250 mm 5 μm
Column Supplier: YMC

| Gradient/Solvent Time [min] | % Solvent [scCO₂] | % Solvent [IPA, 20 mM NH₃] | Flow [mL/min] | Temperature [° C.] | Back Pressure [PSI] |
|---|---|---|---|---|---|
| 0.00 | 70 | 30 | 4.0 | 40 | 2175 |
| 10.0 | 70 | 30 | 4.0 | 40 | 2175 |

Method: 8
Device: Agilent 1260 SFC with DAD and MS
Column: Chiral Art ® Cellulose SC 4.6 × 250 mm 5 μm
Column Supplier: YMC

| Gradient/Solvent Time [min] | % Solvent [scCO₂] | % Solvent [IPA, 20 mM NH₃] | Flow [mL/min] | Temperature [° C.] | Back Pressure [PSI] |
|---|---|---|---|---|---|
| 0.00 | 65 | 35 | 4.0 | 40 | 2175 |
| 10.0 | 65 | 35 | 4.0 | 40 | 2175 |

SYNTHESIS OF INTERMEDIATES

Intermediate 1

(13'S)-9'-(2-chlorophenyl)-3'-methyl-16'-thia-2',4',5',8'-tetraazaspiro[cyclopropane-1,7'-tetracyclo[8.6.0.0²,⁶.0¹¹,¹⁵]hexadecane]-1'(10'),3',5',8',11'(15')-pentaene-13'-carboxylic acid

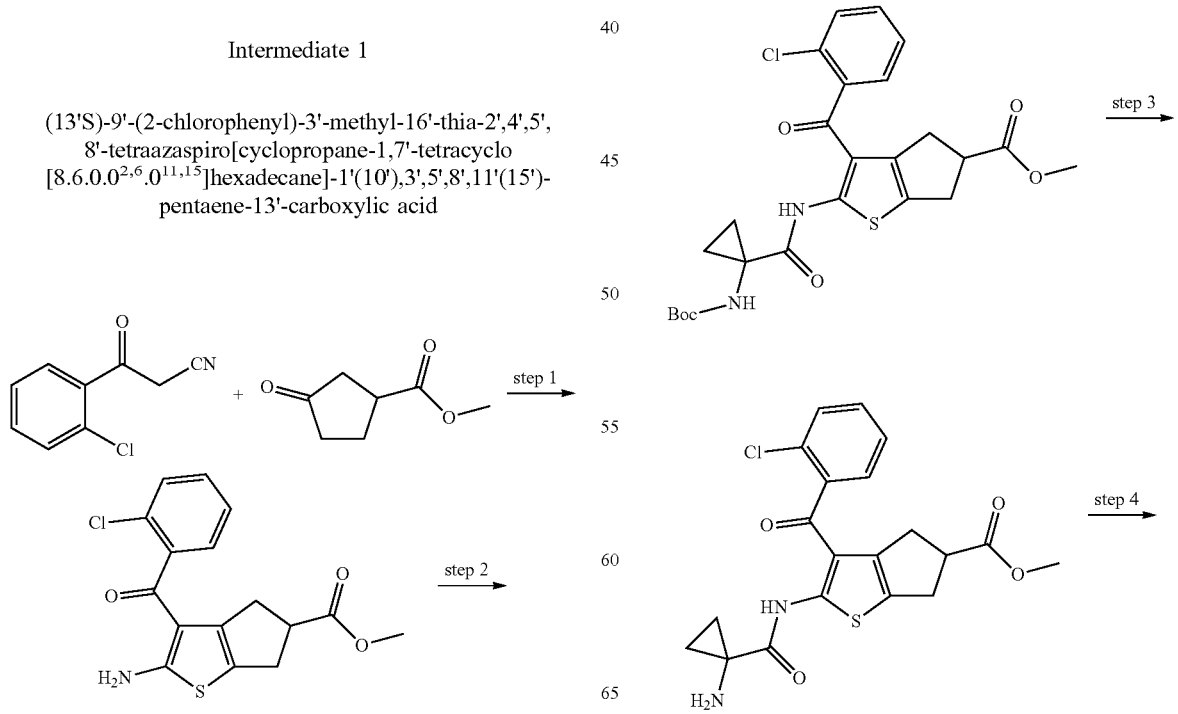

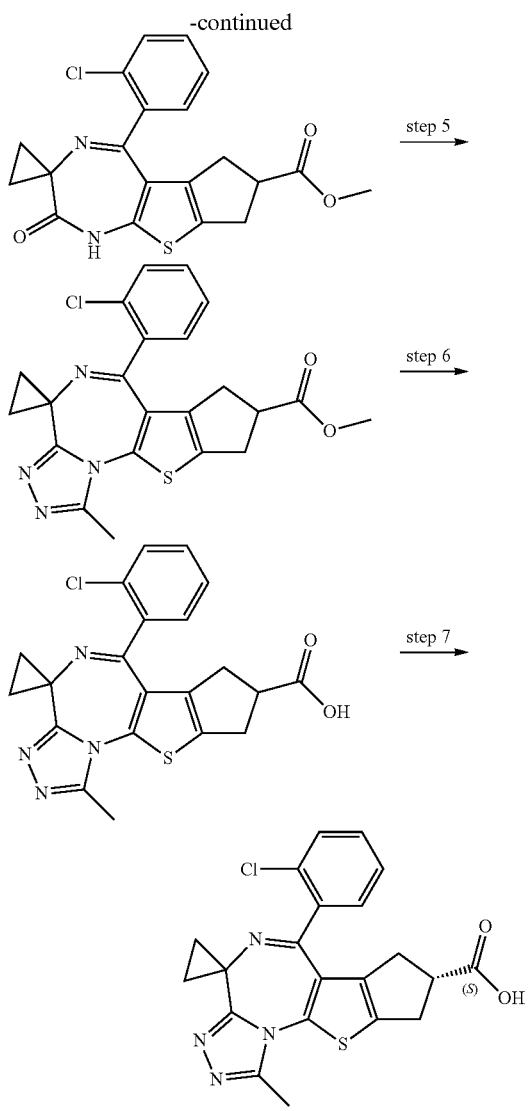

Step 1: methyl 2-amino-3-(2-chlorobenzoyl)-4H,5H,6H-cyclopenta[b]thiophene-5-carboxylate A mixture of 3-(2-chlorophenyl)-3-oxopropanenitrile (126 g), methyl 3-oxocyclopentane-1-carboxylate (100 g), sulfur (22.5 g), morpholine (61.8 mL), and MeOH (800 mL) is stirred at reflux for 4 h. After cooling to room temperature, the reaction mixture is concentrated. The crude product is purified by chromatography on silica gel (pet. ether/DCM 50:50) and then recrystallized from MeOH to give the title compound.

Step 2: methyl 2-(1-{[(tert-butoxy)carbonyl]amino}cyclopropaneamido)-3-(2-chlorobenzoyl)-4H,5H,6H-cyclopenta[b]thiophene-5-carboxylate 2-Chloro-1-methylpyridinium iodide (91 g), triethylamine (116 mL), and 4-dimethylaminopyridine (18 g) are added to a stirred solution of methyl 2-amino-3-(2-chlorobenzoyl)-4H,5H,6H-cyclopenta[b]thiophene-5-carboxylate (100 g) and 1-tert-butoxycarbonylamino-cyclopropanecarboxylic acid (90 g) in DCM (1000 mL). The resulting mixture is stirred at 55 C to 60° C. for 2 d. The mixture is diluted with MeOH and water and the precipitate is separated by filtration to give the title compound.

Step 3: methyl 2-(1-aminocyclopropaneamido)-3-(2-chlorobenzoyl)-4H,5H,6H-cyclopenta[b]thiophene-5-carboxylate 4M HCl in dioxane (400 mL) is added to methyl 2-(1-{[(tert-butoxy)carbonyl]amino)cyclopropaneamido)-3-(2-chlorobenzoyl)-4H,5H,6H-cyclopenta[b]thiophene-5-carboxylate (70 g) in DCM (400 mL) at 0° C. The cooling bath is removed and the mixture is stirred at room temperature for 12 h. The mixture is concentrated to give the crude title compound that is used as is in the next reaction step.

Step 4: methyl 13'-(2-chlorophenyl)-10'-oxo-7'-thia-9',12'-diazaspiro[cyclopropane-1,11'-tricyclo[6.5.0.0$^{2,6}$]tridecane]-1'(8'),2'(6'),12'-triene-4'-carboxylate Pyridine (180 mL) and glacial acetic acid (60 mL) are added to a stirred solution of methyl 2-(1-aminocyclopropaneamido)-3-(2-chlorobenzoyl)-4H,5H,6H-cyclopenta[b]thiophene-5-carboxylate (60 g) in toluene (600 mL). The mixture is stirred at 120° C. for 24 h and then concentrated. The crude compound is purified by chromatography on silica gel (30% EtOAc/70% pet. ether) to obtain the title compound.

Step 5: methyl 9'-(2-chlorophenyl)-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxylate A stirred solution of methyl 13'-(2-chlorophenyl)-10'-oxo-7'-thia-9',12'-diazaspiro[cyclopropane-1,11'-tricyclo[6.5.0.0$^{2,6}$]tridecane]-1'(8'),2'(6'),12'-triene-4'-carboxylate (20 g) in THF (300 mL) is cooled to −78° C. Potassium tert-butoxide (6.1 g) is added and the reaction mixture is warmed to −10° C. and then to rt. After 30 min, the resulting mixture is cooled to −78° C. and diethyl chlorophosphate (10.3 g) is added. The resulting mixture is stirred at −10° C. for 45 min. Acetylhydrazide (7.4 g) is added and the mixture is stirred at room temperature for 45 min. IPA (300 mL) is added and the reaction mixture is stirred at 90° C. for 1 h. The mixture is concentrated and the residue is purified by chromatography on silica gel (DCM/MeOH 96:4) to give the title compound.

Step 6: 9'-(2-chlorophenyl)-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxylic acid LiOH*H$_2$O (4.8 g) is added to methyl 9'-(2-chlorophenyl)-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxylate (10 g) in THF (100 mL) and water (40 mL). The mixture is stirred at room temperature for 4 h. THF is evaporated and the aqueous layer is acidified with concentrated HCl at 0° C. The precipitate is separated by filtration and dried in vacuo to give the title compound.

Step 7: (13'S)-9'-(2-chlorophenyl)-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxylic acid 9'-(2-chlorophenyl)-3'-methyl-16'-thia-2',4',5',8'-tetraazaspiro[cyclopropane-1,7'-tetracyclo[8.6.0.0$^{2,6}$.0$^{11,15}$]

hexa-decane]-1'(10'),3',5',8',11'(15')-pentaene-13'-carboxylic acid (racemic mixture, 2.6 g) is resolved into its enantiomers by SFC on chiral phase [column: Chiralpak IC (30×250 mm, 5 μm); isocratic conditions: 55:45 CO$_2$: MeOH; total flow: 100 g/min; BPR: 100 bar; load/injection: 40 mg; number of injections: 90] to provide the title compound.

SYNTHESIS OF EXAMPLES

Example 1

(13'S)—N-{bicyclo[1.1.1]pentan-1-yl}-9'-(2-chlorophenyl)-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide

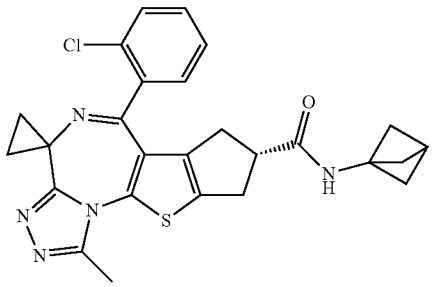 [SMILES: Cc1nnc2n1-c1sc3c(c1C(c1ccccc1Cl)=NC21CC1)C[C@H](C(=O)NC12CC(C1)C2)C3]

(13'S)-9'-(2-chlorophenyl)-3'-methyl-16'-thia-2',4',5',8'-tetraazaspiro[cyclopropane-1,7'-tetracyclo[8.6.0.0$^{2,6}$.0$^{11,15}$]hexa-decane]-1'(10'),3',5',8',11'(15')-pentaene-13'-carboxylic acid (Intermediate 1; 50 mg) and bicyclo[1.1.1]pentan-1-amine (15 mg) are dissolved in DMF (1 mL). DIPEA (41 μL) and TBTU (38 mg) are added and the mixture is stirred at rt for 1 h. The reaction mixture is diluted with DMF and purified by chromatography on reversed phase (HPLC; ACN/water/aqueous ammonia) to give the title compound.

LC-MS (Method 1): $t_R$=0.93 min; Mass spectrum (ESI$^+$): m/z=491 [M+H]$^+$.

Chiral SFC (Method 6): $t_R$=2.33 min; Mass spectrum (ESI$^+$): m/z=490.1 [M]$^+$.

Example 2

4-chloro-3-[(13'S)-3'-methyl-13'-(morpholine-4-carbonyl)-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaen-9'-yl]benzonitrile

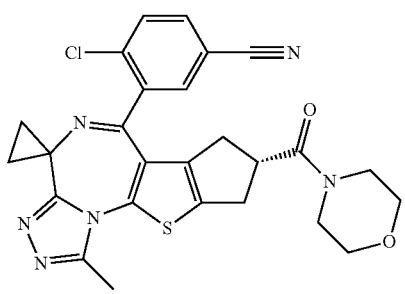 [SMILES: Cc1nnc2n1-c1sc3c(c1C(c1cc(C#N)ccc1Cl)=NC21CC1)C[C@H](C(=O)N1CCOCC1)C3]

H$_2$O (1 mL) and sulfuric acid (20 NL) are added to 4-chloro-3-[(13'S)-3'-methyl-13'-(morpholine-4-carbonyl)-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaen-9'-yl]aniline (Example 6; 65 mg) in THF (1 mL) at 0° C. Sodium nitrite (11 mg) dissolved in H$_2$O (50 NL) is added dropwise. Another flask is charged with a stir bar, potassium cyanide (42 mg), and H$_2$O (500 μL) and cooled to 0° C. To the latter CuCN (15 mg), NaHCO$_3$ (85 mg), and EtOAc (1 mL) are added. The former solution (diazonium salt) is added dropwise to the latter and the resulting mixture is stirred at rt overnight. H$_2$O is added and the mixture is extracted with EtOAc (3×). The combined organic extract is dried (Na$_2$SO$_4$) and concentrated. The residue is chromatographed on silica gel (DCM/MeOH 95:5) to give the title compound.

LC-MS (Method 2): $t_R$=0.83 min; Mass spectrum (ESI$^+$): m/z=519 [M+H]$^+$.

Example 3

(13'S)-9'-(2,5-dichlorophenyl)-3'-methyl-13'-(morpholine-4-carbonyl)-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene

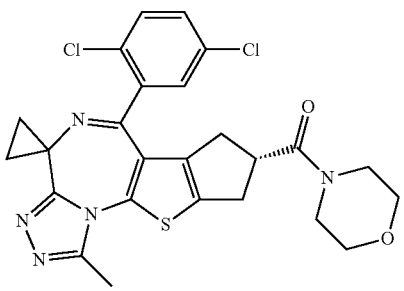 [SMILES: Cc1nnc2n1-c1sc3c(c1C(c1cc(Cl)ccc1Cl)=NC21CC1)C[C@H](C(=O)N1CCOCC1)C3]

4-Chloro-3-[(13'S)-3'-methyl-13'-(morpholine-4-carbonyl)-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaen-9'-yl]aniline (Example 6; 50.0 mg) in MeCN (1 mL) is added to CuCl$_2$ (16 mg) and tert-butyl nitrite (17 μL) in MeCN (2 mL) at 0° C. The mixture is warmed tort and stirred overnight. The mixture is poured into 1M aqueous HCl and stirred for 5 min. After neutralization with 1M aqueous NaOH, the mixture is extracted with EtOAc. The combined organic extract is dried (Na$_2$SO$_4$) and concentrated. The residue is chromatographed on reversed phase (HPLC; ACN/water/aqueous ammonia) to give the title compound.

LC-MS (Method 1): $t_R$=0.90 min; Mass spectrum (ESI$^+$): m/z=528/530 [M+H]$^+$.

Example 4

(13'S)-9'-(5-bromo-2-chlorophenyl)-3'-methyl-13'-(morpholine-4-carbonyl)-16'-thia-2',4',5',8'-tetraazaspiro[cyclopropane-1,7'-tetracyclo[8.6.0.0$^{2,6}$.0$^{11,15}$]hexadecane]-1'(10')3',5',8',11'(15')-pentaene

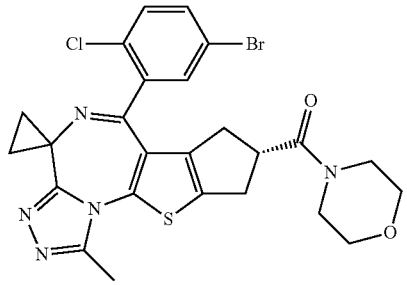 [SMILES: Cc1nnc2n1-c1sc3c(c1C(c1cc(Br)ccc1Cl)=NC21CC1)C[C@H](C(=O)N1CCOCC1)C3]

4-Chloro-3-[(13'S)-3'-methyl-13'-(morpholine-4-carbonyl)-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11' (15')-pentaen-9'-yl]aniline (Example 6; 50 mg) in MeCN (1 mL) is added to CuBr$_2$ (26 mg) and tert-butyl nitrite (16 μL) in MeCN (2 mL) at 0° C. The mixture is warmed to 70° C. and stirred for 2 h. The mixture is poured into 1M aqueous HCl and stirred for 5 min. After neutralization with 1M aqueous NaOH, the mixture is extracted with EtOAc. The combined organic extract is dried (Na$_2$SO$_4$) and concentrated. The residue is chromatographed on reversed phase (HPLC; ACN/water/aqueous ammonia) to give the title compound.

LC-MS (Method 1): $t_R$=0.91 min; Mass spectrum (ESI$^+$): m/z=572/574 [M+H]$^+$.

Reference Example 5

(13'S)-9'-(2-chloro-5-nitrophenyl)-3'-methyl-13'-(morpholine-4-carbonyl)-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene

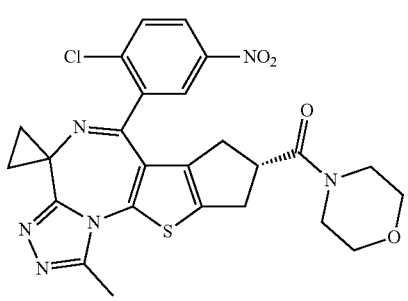 [SMILES: Cc1nnc2n1-c1sc3c(c1C(c1cc([N+](=O)[O-])ccc1Cl)=NC21CC1)C[C@H](C(=O)N1CCOCC1)C3]

(13'S)-9'-(2-chlorophenyl)-3'-methyl-13'-(morpholine-4-carbonyl)-16'-thia-2',4',5',8'-tetraazaspiro[cyclopropane-1, 7'-tetracyclo[8.6.0.0$^{2,6}$.0$^{11,15}$]hexadecane]-1'(10'),3',5',8',11' (15')-pentaene (Example 114; 300 mg) is dissolved in sulfuric acid (2 mL) and cooled to 0° C. A mixture of nitric acid (47 μL) and sulfuric acid (162 μL) is added and the mixture is stirred at rt overnight. If the reaction is not complete (by TLC or HPLC), more of a mixture of nitric acid (30 μL) and sulfuric acid (100 μL) is added and stirring at rt is continued for 5 h. The mixture is poured into ice water, the resulting mixture is neutralized with K$_2$CO$_3$ (pH ~ 8) and extracted with EtOAc. The combined organic extract is dried (Na$_2$SO$_4$) and concentrated. The residue is purified by silica gel column chromatography (DCM/MeOH 95:5) to give the title compound. LC-MS (Method 1): $t_R$=0.86 min; Mass spectrum (ESI$^+$): m/z=539 [M+H]$^+$.

Example 6

4-chloro-3-[(13'S)-3'-methyl-13'-(morpholine-4-carbonyl)-16'-thia-2',4',5',8'-tetraazaspiro[cyclopropane-1,7'-tetracyclo[8.6.0.0$^{2,6}$.0$^{11,15}$]hexadecane]-1' (10'),3',5',8',11'(15')-pentaen-9'-yl]aniline

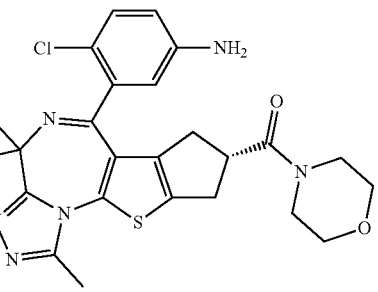

A mixture of (13'S)-9'-(2-chloro-5-nitrophenyl)-3'-methyl-13'-(morpholine-4-carbonyl)-16'-thia-2',4',5',8'-tetraaza-spiro[cyclopropane-1,7'-tetracyclo[8.6.0.0$^{2,6}$.0$^{11,15}$] hexadecane]-1'(10'),3',5',8',11'(15')-pentaene (Reference Example 5, 135 mg), iron (140 mg), THF (5 mL), and H$_2$O (1 mL) is stirred at 80° C. for 4 h. After cooling to rt, the mixture is filtered and the filtrate is concentrated. The residue is chromatographed on silica gel (dichloromethane/methanol 95:5) to give the title compound. LC-MS (Method 1): $t_R$=0.75 min; Mass spectrum (ESI$^+$): m/z=509 [M+H]$^+$.

Example 7

Example 7 is obtained from (13'S)-9'-(2-chlorophenyl)-3'-methyl-16'-thia-2',4',5',8'-tetraazaspiro[cyclopropane-1, 7'-tetracyclo[8.6.0.0$^{2,6}$.0$^{11,15}$]hexadecane]-1'(10'),3',5',8',11' (15')-pentaene-13'-carboxylic acid (Intermediate 1) by following a procedure analogous to that described for Example 1.

| Ex. | Structure/Name | Amine Employed | LC-MS Method | MS (ESI+): m/z [M + H]+ | $t_R$ [min] |
|---|---|---|---|---|---|
| 7 | 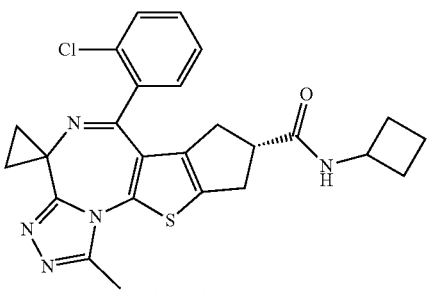 [SMILES: Cc1nnc2n1-c1sc3c(c1C(c1ccccc1Cl)=NC21CC1)C[C@H](C(=O)NC1CCC1)C3](13'S)-9'-(2-chlorophenyl)-N-cyclobutyl-3'-methyl-16'-thia-2',4',5',8'-tetraazaspiro-[cyclopropane-1,7'-tetracyclo[8.6.0.0$^{2,6}$.0$^{11,15}$]-hexadecane]-1'(10'),3',5',8',11'(15')-pentaene-13'-carboxamide | cyclobutylamine | 3<br>Chiral SFC: 6 | 478<br>478.1 | 0.67<br>2.69 |

Example 8

(13'S)-3'-methyl-9'-(2-methylphenyl)-13'-(morpholine-4-carbonyl)-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene

Example 9

2-[(13'S)-3'-methyl-13'-(morpholine-4-carbonyl)-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaen-9'-yl]phenol

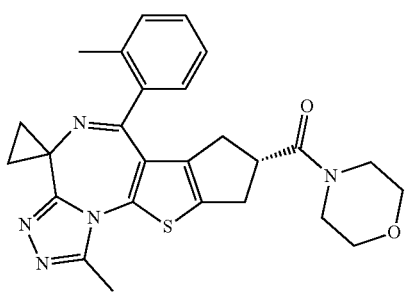 [SMILES: Cc1ccccc1C1=NC2(CC2)c2nnc(C)n2-c2sc3c(c21)C[C@H](C(=O)N1CCOCC1)C3]

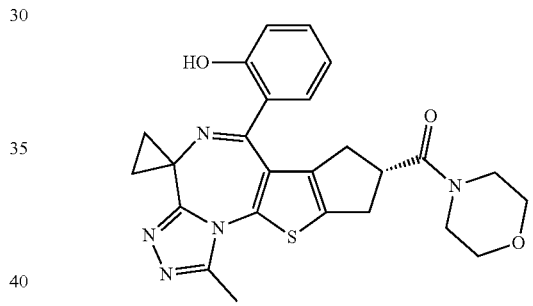

(13'S)-9'-(2-chlorophenyl)-3'-methyl-13'-(morpholine-4-carbonyl)-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene (Example 114; 50 mg), methylboronic acid (12 mg), and potassium phosphate (65 mg) are dissolved in H$_2$O (200 µL) and toluene (1.0 mL). The mixture is purged with Ar for 5 min before Pd(OAc)$_2$ (1.1 mg) and dicyclohexyl(2',6'-dimethoxybiphenyl-2-yl)phosphine (SPhos) (4.1 mg) are added. The mixture is stirred in a microwave oven at 140° C. for 30 min. After cooling to rt, the mixture is diluted with ACN and chromatographed on reversed phase (HPLC; ACN/water/aqueous ammonia) to give the title compound.

LC-MS (Method 1): $t_R$=0.78 min; Mass spectrum (ESI+): m/z=474 [M+H]+.

Chiral SFC [column: Chiral Art® Cellulose_SB (4.6 mm×250 mm, 5 µm); column temperature: 40° C.; flow rate: 4.0 mL/min; BPR: 2175 bar; isocratic conditions: 65:35 CO$_2$:IPA (20 mM NH$_3$)]: $t_R$=3.65 min; Mass spectrum (ESI+): m/z=474.0 [M+H]+.

Step 1: (13'S)-9'-(2-chlorophenyl)-3'-methyl-13'-(morpholine-4-carbonyl)-16'-thia-2',4',5',8'-tetraazaspiro[cyclopropane-1,7'-tetracyclo[8.6.0.02,6.011,15]hexadecane]-1'(10'),3',5',8',11'(15')-pentaene (Example 114; 50 mg), bis(pinacolato)diboron (39 mg) and potassium acetate (30 mg) are dissolved in dioxane (1 mL). The mixture is purged with Ar for 5 min before Pd$_2$dba$_3$ (3.0 mg) and XPhos (2.5 mg) are added. The mixture is stirred in a microwave oven at 120° C. for 30 min. After cooling to rt, the mixture is diluted with dioxane and filtered through celite. The separated solid is washed with dioxane, dried in vacuo, and used for the next reaction step without further purification.

Step 2: The crude product from Step 1 (51 mg) is dissolved in THF (1 mL). The mixture is cooled to 0° C. and hydrogen peroxide (35% in H$_2$O; 53 µL) and aqueous 4 M NaOH (51 µL) are added. The mixture is stirred overnight while warming to rt. The mixture is diluted with EtOAc and washed with aqueous Na$_2$S2O3 solution. The organic layer is dried (Na$_2$SO$_4$) and concentrated. The residue is chromatographed on reversed phase (HPLC; ACN/water/aqueous ammonia) to give the title compound. LC-MS (Method 1): $t_R$=0.81 min; Mass spectrum (ESI+): m/z=476 [M+H]+. Chiral SFC (Method 7): $t_R$=4.78 min; Mass spectrum (ESI+): m/z=476.0 [M+H]+.

Examples 10-103

Examples 10-103 compiled in the following table are obtained from (13'S)-9'-(2-chlorophenyl)-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxylic acid (Intermediate 1) by following a procedure analogous to that described for Example 1.

| Ex. | Structure/Name | Amine Employed | LC-MS Method | MS (ESI+): m/z [M + H]$^+$ | $t_R$ [min] |
|---|---|---|---|---|---|
| 10 | (13'S)-9'-(2-chlorophenyl)-13'-(2,2-dimethylmorpholine-4-carbonyl)-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene | 2,2-dimethylmorpholine | 3 | 520 | 0.66 |
| 11 | (13'S)-13'-{2-azabicyclo[2.1.1]hexane-2-carbonyl}-9'-(2-chlorophenyl)-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene | 2-azabicyclo[2.1.1]-hexane | 3 | 490 | 0.67 |
| 12 | (13'S)-9'-(2-chlorophenyl)-3'-methyl-N-[(1S,2S)-2-methylcyclopropyl]-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | (1S,2S)-2-methylcyclopropan-1-amine | 1 Chiral SFC: 7 | 478 477.9 | 0.89 3.60 |

| Ex. | Structure/Name | Amine Employed | LC-MS Method | MS (ESI+): m/z [M + H]+ | $t_R$ [min] |
|---|---|---|---|---|---|
| 13 | (13'S)-9'-(2-chlorophenyl)-13'-[(2R,6S)-2,6-dimethylmorpholine-4-carbonyl]-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene | (2R,6S)-2,6-dimethylmorpholine | 3 | 522 | 0.70 |
| 14 | (13'S)-9'-(2-chlorophenyl)-N-cyclopentyl-3'-methyl-16'-thia-2',4',5',8'-tetraazaspiro-[cyclopropane-1,7'-tetracyclo[8.6.0.0$^{2,6}$.0$^{11,15}$]-hexadecane]-1'(10'),3',5',8',11'(15')-pentaene-13'-carboxamide | cyclopentanamine | 4 | 492 | 0.70 |
| 15 | (13'S)-9'-(2-chlorophenyl)-3'-methyl-N-[(1r,4r)-4-(trifluoromethyl)cyclohexyl]-16'-thia-2',4',5',8'-tetraazaspiro[cyclopropane-1,7'-tetracyclo-[8.6.0.0$^{2,6}$.0$^{11,15}$]hexadecane]-1'(10'),3',5',8',11'(15')-pentaene-13'-carboxamide | (1r,4r)-4-(trifluoromethyl)cyclohexan-1-amine | 4 | 574 | 0.81 |

-continued

| Ex. | Structure/Name | Amine Employed | LC-MS Method | MS (ESI+): m/z [M + H]⁺ | $t_R$ [min] |
|---|---|---|---|---|---|
| 16 | (13'S)-9'-(2-chlorophenyl)-3'-methyl-N-[1-(trifluoromethyl)cyclopropyl]-16'-thia-2',4',5',8'-tetraazaspiro[cyclopropane-1,7'-tetracyclo-[8.6.0.0²,⁶.0¹¹,¹⁵]hexadecane]-1'(10'),3',5',8',11'(15')-pentaene-13'-carboxamide | 1-(trifluoromethyl)-cyclopropan-1-amine | 4 | 532 | 0.70 |
| 17 | (13'S)-9'-(2-chlorophenyl)-3'-methyl-N-[(1S,2R)-2-phenylcyclopropyl]-16'-thia-2',4',5',8'-tetraaza-spiro[cyclopropane-1,7'-tetracyclo-[8.6.0.0²,⁶.0¹¹,¹⁵]hexadecane]-1'(10'),3',5',8',11'(15')-pentaene-13'-carboxamide | (1S,2R)-2-phenylcyclopropan-1-amine | 4 | 540 | 0.76 |
| 18 | (13'S)-9'-(2-chlorophenyl)-3'-methyl-N-(1-methylcyclopropyl)-16'-thia-2',4',5',8'-tetraazaspiro[cyclopropane-1,7'-tetracyclo-[8.6.0.0²,⁶.0¹¹,¹⁵]hexadecane]-1'(10'),3',5',8',11'(15')-pentaene-13'-carboxamide | 1-methyl-cyclopropan-1-amine | 4 | 478 | 0.64 |

| Ex. | Structure/Name | Amine Employed | LC-MS Method | MS (ESI+): m/z [M + H]+ | $t_R$ [min] |
|---|---|---|---|---|---|
| 19 | (13'S)-N-[(1R,5S)-bicyclo[3.1.0]hexan-6-yl]-9'-(2-chlorophenyl)-3'-methyl-16'-thia-2',4',5',8'-tetraazaspiro[cyclopropane-1,7'-tetracyclo-[8.6.0.0²,⁶.0¹¹,¹⁵]hexadecane]-1'(10'),3',5',8',11'(15')-pentaene-13'-carboxamide | (1R,5S)-bicyclo[3.1.0]-hexan-6-amine | 4 | 504 | 0.72 |
| 20 | (13'S)-9'-(2-chlorophenyl)-N-ethyl-3'-methyl-N-[(1r,4r)-4-hydroxycyclohexyl]-16'-thia-2',4',5',8'-tetraazaspiro[cyclopropane-1,7'-tetracyclo-[8.6.0.0²,⁶.0¹¹,¹⁵]hexadecane]-1'(10'),3',5',8',11'(15')-pentaene-13'-carboxamide | (1r,4r)-4-(ethylamino)-cyclohexan-1-ol | 4 | 550 | 0.61 |
| 21 | (13'S)-9'-(2-chlorophenyl)-N-cyclobutyl-N,3'-dimethyl-16'-thia-2',4',5',8'-tetraazaspiro-[cyclopropane-1,7'-tetracyclo[8.6.0.0²,⁶.0¹¹,¹⁵]-hexadecane]-1'(10'),3',5',8',11'(15')-pentaene-13'-carboxamide | N-methyl-cyclobutanamine | 4 | 492 | 0.75 |

-continued

| Ex. | Structure/Name | Amine Employed | LC-MS Method | MS (ESI+): m/z [M + H]+ | $t_R$ [min] |
|---|---|---|---|---|---|
| 22 | (13'S)-9'-(2-chlorophenyl)-N-(6-fluoro-2,3-dihydro-1H-inden-1-yl)-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | 6-fluoro-2,3-dihydro-1H-inden-1-amine | 4 | 558 | 0.82 |
| 23 | (13'S)-9'-(2-chlorophenyl)-3'-methyl-N-{2-methyl-4H,5H,6H,7H-pyrazolo[1,5-a]pyridin-6-yl}-16'-thia-2',4',5',8'-tetraazaspiro-[cyclopropane-1,7'-tetracyclo[8.6.0.0$^{2,6}$.0$^{11,15}$]-hexadecane]-1'(10'),3',5',8',11'(15')-pentaene-13'-carboxamide | 2-methyl-4H,5H,6H,7H-pyrazolo[1,5-a]-pyridin-6-amine | 4 | 558 | 0.60 |
| 24 | (13'S)-9'-(2-chlorophenyl)-N-[(1S)-3,3-difluorocyclopentyl]-3'-methyl-16'-thia-2',4',5',8'-tetraazaspiro[cyclopropane-1,7'-tetracyclo-[8.6.0.0$^{2,6}$.0$^{11,15}$]hexadecane]-1'(10'),3',5',8',11'(15')-pentaene-13'-carboxamide | (1S)-3,3-difluorocyclopentan-1-amine | 4 | 528 | 0.67 |

-continued

| Ex. | Structure/Name | Amine Employed | LC-MS Method | MS (ESI+): m/z [M + H]+ | $t_R$ [min] |
|---|---|---|---|---|---|
| 25 | (13'S)-9'-(2-chlorophenyl)-N-(3,3-difluorocyclohexyl)-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | 3,3-difluorocyclohexan-1-amine | 4 | 542 | 0.71 |
| 26 | (13'S)-9'-(2-chlorophenyl)-3'-methyl-N-(1-methylcyclopentyl)-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | 1-methyl-cyclopentan-1-amine | 4 | 506 | 0.78 |
| 27 | (13'S)-9'-(2-chloropheny)-N-(3,3-difluorocyclobutyl)-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | 3,3-difluoro-cyclobutan-1-amine | 4 | 514 | 0.66 |

| Ex. | Structure/Name | Amine Employed | LC-MS Method | MS (ESI+): m/z [M + H]⁺ | $t_R$ [min] |
|---|---|---|---|---|---|
| 28 | 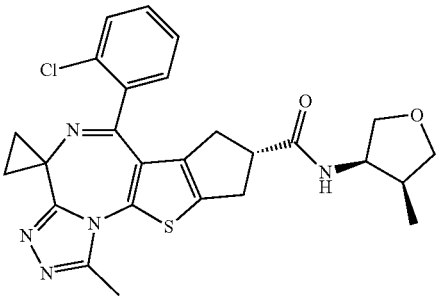 [SMILES: Cc1nnc2n1-c1sc3c(c1C(c1ccccc1Cl)=NC21CC1)C[C@H](C(=O)N[C@H]1COC[C@H]1C)C3]<br>(13'S)-9'-(2-chlorophenyl)-3'-methyl-N-[(3R,4S)-4-methyloxolan-3-yl]-16'-thia-2',4',5',8'-tetraazaspiro[cyclopropane-1,7'-tetracyclo-[8.6.0.0²,⁶.0¹¹,¹⁵]hexadecane]-1'(10'),3',5',8',11'(15')-pentaene-13'-carboxamide | (3R,4S)-4-methyl-oxolan-3-amine | 4 | 508 | 0.57 |
| 29 | 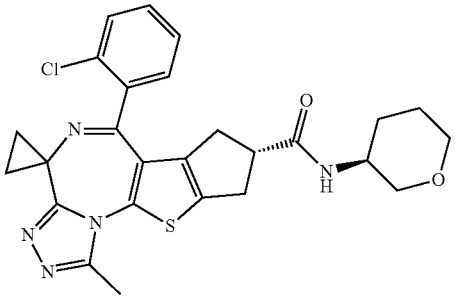 [SMILES: Cc1nnc2n1-c1sc3c(c1C(c1ccccc1Cl)=NC21CC1)C[C@H](C(=O)N[C@H]1CCCOC1)C3]<br>(13'S)-9'-(2-chlorophenyl)-3'-methyl-N-[(3S)-oxan-3-yl]-16'-thia-2',4',5',8'-tetraazaspiro-[cyclopropane-1,7'-tetracyclo-[8.6.0.0²,⁶.0¹¹,¹⁵]hexadecane]-1'(10'),3',5',8',11'(15')-pentaene-13'-carboxamide | (3S)-oxan-3-amine | 4 | 508 | 0.58 |
| 30 | 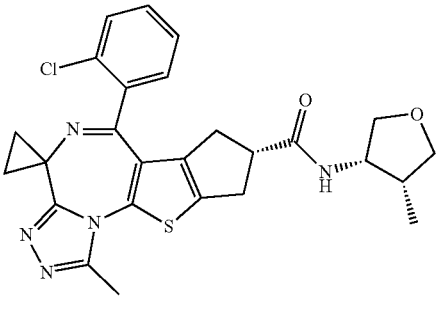 [SMILES: Cc1nnc2n1-c1sc3c(c1C(c1ccccc1Cl)=NC21CC1)C[C@H](C(=O)N[C@@H]1COC[C@@H]1C)C3]<br>(13'S)-9'-(2-chlorophenyl)-3'-methyl-N-[(3S,4R)-4-methyloxolan-3-yl]-16'-thia-2',4',5',8'-tetraaza-spiro[cyclopropane-1,7'-tetracyclo-[8.6.0.0²,⁶.0¹¹,¹⁵]hexadecane]-1'(10'),3',5',8',11'(15')-pentaene-13'-carboxamide | (3S,4R)-4-methyl-oxolan-3-amine | 4 | 508 | 0.60 |

-continued

| Ex. | Structure/Name | Amine Employed | LC-MS Method | MS (ESI+): m/z [M + H]+ | $t_R$ [min] |
|---|---|---|---|---|---|
| 31 | (13'S)-9'-(2-chlorophenyl)-N-(2,3-dihydro-1H-inden-2-yl)-3'-methyl-16'-thia-2',4',5',8'-tetraazaspiro[cyclopropane-1,7'-tetracyclo-[8.6.0.0$^{2,6}$.0$^{11,15}$]hexadecane]-1'(10'),3',5',8',11'(15')-pentaene-13'-carboxamide | 2,3-dihydro-1H-inden-2-amine | 4 | 540 | 0.77 |
| 32 | (13'S)-9'-(2-chlorophenyl)-N-[(1R)-2,3-dihydro-1H-inden-1-yl]-3'-methyl-16'-thia-2',4',5',8'-tetraazaspiro[cyclopropane-1,7'-tetracyclo-[8.6.0.0$^{2,6}$.0$^{11,15}$]hexadecane]-1'(10'),3',5',8',11'(15')-pentaene-13'-carboxamide | (1R)-2,3-dihydro-1H-inden-1-amine | 4 | 540 | 0.79 |
| 33 | (13'S)-9'-(2-chlorophenyl)-N-(2,2-dimethyloxan-4-yl)-3'-methyl-16'-thia-2',4',5',8'-tetraazaspiro-[cyclopropane-1,7'-tetracyclo-[8.6.0.0$^{2,6}$.0$^{11,15}$]hexadecane]-1'(10'),3',5',8',11'(15')-pentaene-13'-carboxamide | 2,2-dimethyl-oxan-4-amine | 4 | 536 | 0.63 |

-continued

| Ex. | Structure/Name | Amine Employed | LC-MS Method | MS (ESI+): m/z [M + H]+ | $t_R$ [min] |
|---|---|---|---|---|---|
| 34 | (13'S)-9'-(2-chlorophenyl)-3'-methyl-N-(4,5,6,7-tetrahydro-1,3-benzothiazol-6-yl)-16'-thia-2',4',5',8'-tetraazaspiro[cyclopropane-1,7'-tetracyclo[8.6.0.0²,⁶.0¹¹,¹⁵]hexadecane]-1'(10'),3',5',8',11'(15')-pentaene-13'-carboxamide | 4,5,6,7-tetrahydro-1,3-benzothiazol-6-amine | 4 | 561 | 0.61 |
| 35 | (13'S)-9'-(2-chlorophenyl)-N-[1-(5-chloropyridin-2-yl)cyclopropyl]-3'-methyl-16'-thia-2',4',5',8'-tetraazaspiro[cyclopropane-1,7'-tetracyclo-[8.6.0.0²,⁶.0¹¹,¹⁵]hexadecane]-1'(10'),3',5',8',11'(15')-pentaene-13'-carboxamide | 1-(5-chloropyridin-2-yl)cyclopropan-1-amine | 4 | 575 | 0.75 |
| 36 | (13'S)-9'-(2-chlorophenyl)-3'-methyl-N-[(1s,4s)-4-fluorocyclohexyl]-16'-thia-2',4',5',8'-tetraazaspiro[cyclopropane-1,7'-tetracyclo-[8.6.0.0²,⁶.0¹¹,¹⁵]hexadecane]-1'(10'),3',5',8',11'(15')-pentaene-13'-carboxamide | (1s,4s)-4-fluoro-cyclohexan-1-amine | 4 | 575 | 0.75 |

-continued

| Ex. | Structure/Name | Amine Employed | LC-MS Method | MS (ESI+): m/z [M + H]+ | $t_R$ [min] |
|---|---|---|---|---|---|
| 37 | (13'S)-9'-(2-chlorophenyl)-N,3'-dimethyl-N-(oxan-4-yl)-16'-thia-2',4',5',8'-tetraazaspiro-[cyclopropane-1,7'-tetracyclo-[8.6.0.0²,⁶.0¹¹,¹⁵]hexadecane]-1'(10'),3',5',8',11'(15')-pentaene-13'-carboxamide | N-methyl-oxan-4-amine | 4 | 522 | 0.62 |
| 38 | (13'S)-9'-(2-chlorophenyl)-3'-methyl-N-(1-methylcyclobutyl)-16'-thia-2',4',5',8'-tetraazaspiro[cyclopropane-1,7'-tetracyclo-[8.6.0.0²,⁶.0¹¹,¹⁵]hexadecane]-1'(10'),3',5',8',11'(15')-pentaene-13'-carboxamide | 1-methylcyclobutan-1-amine | 4 | 492 | 0.73 |
| 39 | (13'S)-9'-(2-chlorophenyl)-3'-methyl-N-[(3R,4S)-4-phenyloxolan-3-yl]-16'-thia-2',4',5',8'-tetraazaspiro[cyclopropane-1,7'-tetracyclo-[8.6.0.0²,⁶.0¹¹,¹⁵]hexadecane]-1'(10'),3',5',8',11'(15')-pentaene-13'-carboxamide | (3R,4S)-4-phenyl-oxolan-3-amine | 4 | 570 | 0.68 |

-continued

| Ex. | Structure/Name | Amine Employed | LC-MS Method | MS (ESI+): m/z [M + H]+ | $t_R$ [min] |
|---|---|---|---|---|---|
| 40 | 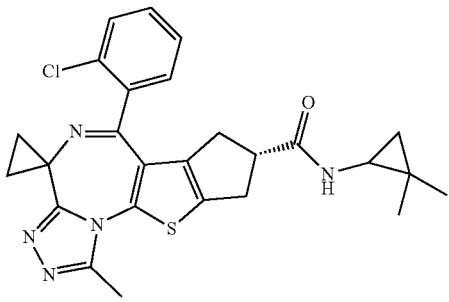 [SMILES: Cc1nnc2n1-c1sc3c(c1C(c1ccccc1Cl)=NC21CC1)C[C@H](C(=O)NC1CC1(C)C)C3]<br>(13'S)-9'-(2-chlorophenyl)-N-(2,2-dimethyl-cyclopropyl)-3'-methyl-16'-thia-2',4',5',8'-tetraazaspiro[cyclopropane-1,7'-tetracyclo-[8.6.0.0$^{2,6}$.0$^{11,15}$]hexadecane]-1'(10'),3',5',8',11'(15')-pentaene-13'-carboxamide | 2,2-dimethyl-cyclopropan-1-amine | 4 | 492 | 0.69 |
| 41 | 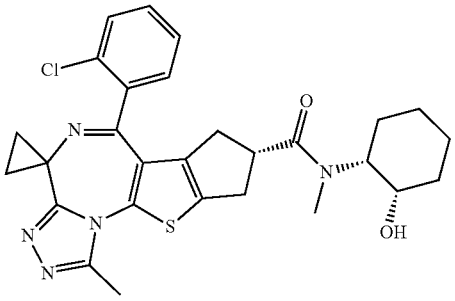 [SMILES: Cc1nnc2n1-c1sc3c(c1C(c1ccccc1Cl)=NC21CC1)C[C@H](C(=O)N(C)[C@@H]1CCCC[C@@H]1O)C3]<br>(13'S)-9'-(2-chlorophenyl)-N-[(1R,2S)-2-hydroxycyclohexyl]-N,3'-dimethyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | (1S,2R)-2-(methylamino)-cyclohexan-1-ol | 4 | 536 | 0.70 |
| 42 | 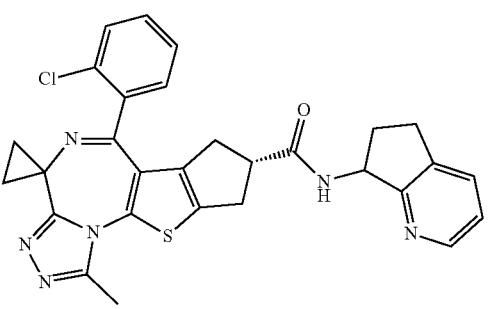 [SMILES: Cc1nnc2n1-c1sc3c(c1C(c1ccccc1Cl)=NC21CC1)C[C@H](C(=O)NC1CCc2cccnc21)C3]<br>(13'S)-9'-(2-chlorophenyl)-N-{5H,6H,7H-cyclopenta[b]pyridin-7-yl}-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | 5H,6H,7H-cyclopenta[b]-pyridin-7-amine | 4 | 541 | 0.62 |

| Ex. | Structure/Name | Amine Employed | LC-MS Method | MS (ESI+): m/z [M + H]+ | $t_R$ [min] |
|---|---|---|---|---|---|
| 43 | (13'S)-9'-(2-chlorophenyl)-N-(5,5-difluorooxan-3-yl)-3'-methyl-16'-thia-2',4',5',8'-tetraazaspiro-[cyclopropane-1,7'-tetracyclo-[8.6.0.0$^{2,6}$.0$^{11,15}$]-hexadecane]-1'(10'),3',5',8',11'(15')-pentaene-13'-carboxamide | 5,5-difluoro-oxan-3-amine | 4 | 544 | 0.62 |
| 44 | (13'S)-9'-(2-chlorophenyl)-N-cyclohexyl-N,3'-dimethyl-16'-thia-2',4',5',8'-tetraazaspiro-[cyclopropane-1,7'-tetracyclo[8.6.0.0$^{2,6}$.0$^{11,15}$]-hexadecane]-1'(10'),3',5',8',11'(15')-pentaene-13'-carboxamide | N-methyl-cyclohexanamine | 4 | 520 | 0.85 |
| 45 | (13'S)-9'-(2-chlorophenyl)-3'-methyl-N-(4-methyloxan-4-yl)-16'-thia-2',4',5',8'-tetraaza-spiro[cyclopropane-1,7'-tetracyclo-[8.6.0.0$^{2,6}$.0$^{11,15}$]hexadecane]-1'(10'),3',5',8',11'(15')-pentaene-13'-carboxamide | 4-methyl-oxan-4-amine | 4 | 522 | 0.62 |

| Ex. | Structure/Name | Amine Employed | LC-MS Method | MS (ESI+): m/z [M + H]+ | $t_R$ [min] |
|---|---|---|---|---|---|
| 46 | (13'S)-9'-(2-chlorophenyl)-3'-methyl-N-(1-phenylcyclopropyl)-16'-thia-2',4',5',8'-tetraazaspiro[cyclopropane-1,7'-tetracyclo-[8.6.0.0²,⁶.0¹¹,¹⁵]hexadecane]-1'(10'),3',5',8',11'(15')-pentaene-13'-carboxamide | 1-phenyl-cyclopropan-1-amine | 4 | 540 | 0.74 |
| 47 | (13'S)-9'-(2-chlorophenyl)-N-(2,2-dimethyl-cyclobutyl)-3'-methyl-16'-thia-2',4',5',8'-tetraazaspiro[cyclopropane-1,7'-tetracyclo-[8.6.0.0²,⁶.0¹¹,¹⁵]hexadecane]-1'(10'),3',5',8',11'(15')-pentaene-13'-carboxamide | 2,2-dimethyl-cyclobutan-1-amine | 4 | 506 | 0.77 |
| 48 | (13'S)-9'-(2-chlorophenyl)-N,3'-dimethyl-N-[(3R)-oxolan-3-yl]-16'-thia-2',4',5',8'-tetraaza-spiro[cyclopropane-1,7'-tetracyclo-[8.6.0.0²,⁶.0¹¹,¹⁵]hexadecane]-1'(10'),3',5',8',11'(15')-pentaene-13'-carboxamide | (3R)-N-methyl-oxolan-3-amine | 4 | 508 | 0.59 |

-continued

| Ex. | Structure/Name | Amine Employed | LC-MS Method | MS (ESI+): m/z [M + H]+ | $t_R$ [min] |
|---|---|---|---|---|---|
| 49 | 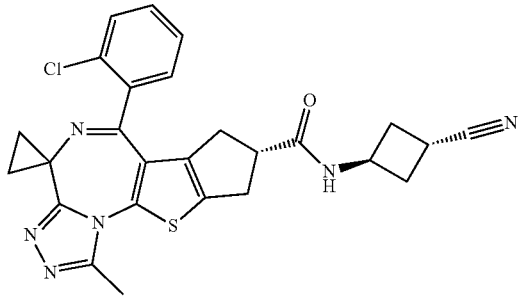 [SMILES: Cc1nnc2n1-c1sc3c(c1C(c1ccccc1Cl)=NC21CC1)C[C@H](C(=O)N[C@H]1C[C@H](C#N)C1)C3]<br>(13'S)-9'-(2-chlorophenyl)-3'-methyl-N-[(1r,3r)-3-cyanocyclobutyl]-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | (1r,3r)-3-amino-cyclobutane-1-carbonitrile | 4 | 503 | 0.55 |
| 50 | 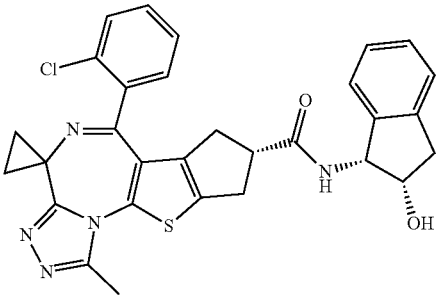 [SMILES: Cc1nnc2n1-c1sc3c(c1C(c1ccccc1Cl)=NC21CC1)C[C@H](C(=O)N[C@@H]1c2ccccc2C[C@@H]1O)C3]<br>(13'S)-9'-(2-chlorophenyl)-N-[(1R,2S)-2-hydroxy-2,3-dihydro-1H-inden-1-yl]-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | (1R,2S)-1-amino-2,3-dihydro-1H-inden-2-ol | 4 | 556 | 0.67 |
| 51 | 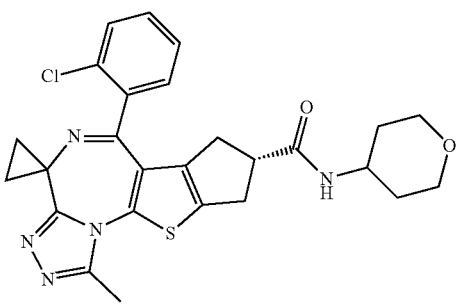 [SMILES: Cc1nnc2n1-c1sc3c(c1C(c1ccccc1Cl)=NC21CC1)C[C@H](C(=O)NC1CCOCC1)C3]<br>(13'S)-9'-(2-chlorophenyl)-3'-methyl-N-(oxan-4-yl)-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | oxan-4-amine | 4 | 508 | 0.56 |

-continued

| Ex. | Structure/Name | Amine Employed | LC-MS Method | MS (ESI+): m/z [M + H]+ | $t_R$ [min] |
|---|---|---|---|---|---|
| 52 | (13'S)-9'-(2-chlorophenyl)-3'-methyl-N-[(1s,4s)-4-(trifluoromethyl)cyclohexyl]-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | (1s,4s)-4-(trifluoromethyl)-cyclohexan-1-amine | 4 | 574 | 0.81 |
| 53 | (13'S)-9'-(2-chlorophenyl)-N-[(1S)-7-fluoro-2,3-dihydro-1H-inden-1-yl]-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | (1S)-7-fluoro-2,3-dihydro-1H-inden-1-amine | 4 | 558 | 0.78 |
| 54 | (13'S)-9'-(2-chlorophenyl)-3'-methyl-N-(1-methyl-4,5,6,7-tetrahydro-1H-indazol-6-yl)-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | 1-methyl-4,5,6,7-tetrahydro-1H-indazol-6-amine | 4 | 558 | 0.59 |

| Ex. | Structure/Name | Amine Employed | LC-MS Method | MS (ESI+): m/z [M + H]+ | $t_R$ [min] |
|---|---|---|---|---|---|
| 55 | (13'S)-9'-(2-chlorophenyl)-N-(2,3-dihydro-1-benzofuran-3-yl)-3'-methyl-16'-thia-2',4',5',8'-tetraazaspiro[cyclopropane-1,7'-tetracyclo[8.6.0.0²,⁶.0¹¹,¹⁵]hexadecane]-1'(10'),3',5',8',11'(15')-pentaene-13'-carboxamide | 2,3-dihydro-1-benzofuran-3-amine | 4 | 542 | 0.73 |
| 56 | (13'S)-9'-(2-chlorophenyl)-N-[1-(3-fluorophenyl)cyclopropyl]-3'-methyl-16'-thia-2',4',5',8'-tetraazaspiro[cyclopropane-1,7'-tetracyclo[8.6.0.0²,⁶.0¹¹,¹⁵]hexadecane]-1'(10'),3',5',8',11'(15')-pentaene-13'-carboxamide | 1-(3-fluorophenyl)-cyclopropan-1-amine | 4 | 558 | 0.76 |
| 57 | (13'S)-9'-(2-chlorophenyl)-N-[(1R,2R)-2-methoxycyclobutyl]-3'-methyl-16'-thia-2',4',5',8'-tetraazaspiro[cyclopropane-1,7'-tetracyclo[8.6.0.0²,⁶.0¹¹,¹⁵]hexadecane]-1'(10'),3',5',8',11'(15')-pentaene-13'-carboxamide | (1R,2R)-2-methoxy-cyclobutan-1-amine | 4 | 508 | 0.60 |

-continued

| Ex. | Structure/Name | Amine Employed | LC-MS Method | MS (ESI+): m/z [M + H]+ | $t_R$ [min] |
|---|---|---|---|---|---|
| 58 | 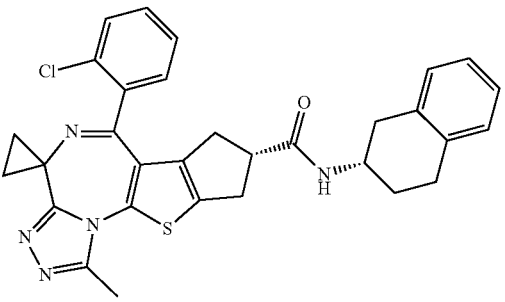 [SMILES: Cc1nnc2n1-c1sc3c(c1C(c1ccccc1Cl)=NC21CC1)C[C@H](C(=O)N[C@H]1CCc2ccccc2C1)C3]<br>(13'S)-9'-(2-chlorophenyl)-3'-methyl-N-[(2S)-1,2,3,4-tetrahydronaphthalen-2-yl]-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | (2S)-1,2,3,4-tetrahydro-naphthalen-2-amine | 4 | 554 | 0.81 |
| 59 | 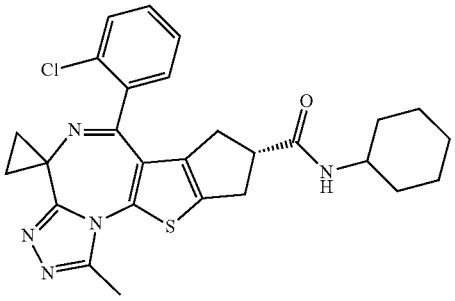 [SMILES: Cc1nnc2n1-c1sc3c(c1C(c1ccccc1Cl)=NC21CC1)C[C@H](C(=O)NC1CCCCC1)C3]<br>(13'S)-9'-(2-chlorophenyl)-N-cyclohexyl-3'-methyl-16'-thia-2',4',5',8'-tetraaza-spiro[cyclopropane-1,7'-tetracyclo-[8.6.0.0$^{2,6}$.0$^{11,15}$]hexadecane]-1'(10'),3',5',8',11'(15')-pentaene-13'-carboxamide | cyclohexanamine | 4 | 506 | 0.75 |
| 60 | 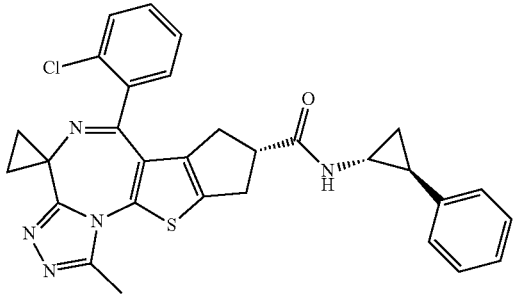 [SMILES: Cc1nnc2n1-c1sc3c(c1C(c1ccccc1Cl)=NC21CC1)C[C@H](C(=O)N[C@@H]1C[C@H]1c1ccccc1)C3]<br>(13'S)-9'-(2-chlorophenyl)-3'-methyl-N-[(1R,2S)-2-phenylcyclopropyl]-16'-thia-2',4',5',8'-tetraazaspiro[cyclopropane-1,7'-tetracyclo-[8.6.0.0$^{2,6}$.0$^{11,15}$]hexadecane]-1'(10'),3',5',8',11'(15')-pentaene-13'-carboxamide | (1R,2S)-2-phenyl-cyclopropan-1-amine | 4 | 540 | 0.80 |

-continued

| Ex. | Structure/Name | Amine Employed | LC-MS Method | MS (ESI+): m/z [M + H]+ | $t_R$ [min] |
|---|---|---|---|---|---|
| 61 | 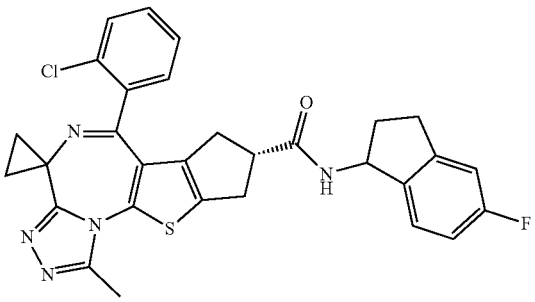 [SMILES: Cc1nnc2n1-c1sc3c(c1C(c1ccccc1Cl)=NC21CC1)C[C@H](C(=O)NC1CCc2cc(F)ccc21)C3]<br>(13'S)-9'-(2-chlorophenyl)-N-(5-fluoro-2,3-dihydro-1H-inden-1-yl)-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | 5-fluoro-2,3-dihydro-1H-inden-1-amine | 4 | 558 | 0.82 |
| 62 | 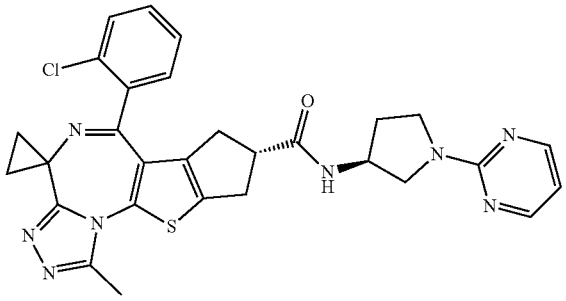 [SMILES: Cc1nnc2n1-c1sc3c(c1C(c1ccccc1Cl)=NC21CC1)C[C@H](C(=O)N[C@H]1CCN(c2ncccn2)C1)C3]<br>(13'S)-9'-(2-chlorophenyl)-3'-methyl-N-[(3S)-1-(pyrimidin-2-yl)pyrrolidin-3-yl]-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | (3S)-1-(pyrimidin-2-yl)pyrrolidin-3-amine | 4 | 571 | 0.49 |
| 63 | 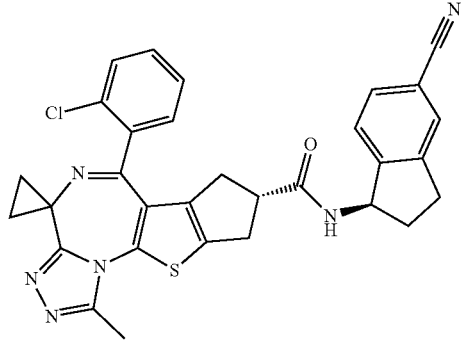 [SMILES: Cc1nnc2n1-c1sc3c(c1C(c1ccccc1Cl)=NC21CC1)C[C@H](C(=O)N[C@@H]1CCc2cc(C#N)ccc21)C3]<br>(13'S)-9'-(2-chlorophenyl)-N-[(1R)-5-cyano-2,3-dihydro-1H-inden-1-yl]-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | (1R)-1-amino-2,3-dihydro-1H-indene-5-carbonitrile | 4 | 565 | 0.71 |

-continued

| Ex. | Structure/Name | Amine Employed | LC-MS Method | MS (ESI+): m/z [M + H]+ | $t_R$ [min] |
|---|---|---|---|---|---|
| 64 | (13'S)-9'-(2-chlorophenyl)-3'-methyl-N-{7-oxaspiro[3.5]nonan-1-yl}-16'-thia-2',4',5',8'-tetraazaspiro[cyclopropane-1,7'-tetracyclo-[8.6.0.0$^{2,6}$.0$^{11,15}$]hexadecane]-1'(10'),3',5',8',11'(15')-pentaene-1 3'-carboxamide | 7-oxaspiro[3.5]-nonan-1-amine | 4 | 548 | 0.66 |
| 65 | (13'S)-9'-(2-chlorophenyl)-13'-(3,3-dimethyl-azetidine-1-carbonyl)-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene | 3,3-dimethyl-azetidine | 4 | 492 | 0.73 |
| 66 | (13'S)-9'-(2-chlorophenyl)-3'-methyl-N-propyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | propan-1-amine | 4 | 466 | 0.64 |

-continued

| Ex. | Structure/Name | Amine Employed | LC-MS Method | MS (ESI+): m/z [M + H]⁺ | $t_R$ [min] |
|---|---|---|---|---|---|
| 67 | (13'S)-9'-(2-chlorophenyl)-3'-methyl-N-[2-(trifluoromethoxy)ethyl]-16'-thia-2',4',5',8'-tetraazaspiro[cyclopropane-1,7'-tetracyclo-[8.6.0.0²,⁶.0¹¹,¹⁵]hexadecane]-1'(10'),3',5',8',11'(15')-pentaene-13'-carboxamide | 2-(trifluoromethoxy)-ethan-1-amine | 4 | 536 | 0.71 |
| 68 | (13'S)-9'-(2-chlorophenyl)-N-(cyclopropylmethyl)-3'-methyl-16'-thia-2',4',5',8'-tetraazaspiro[cyclopropane-1,7'-tetracyclo-[8.6.0.0²,⁶.0¹¹,¹⁵]hexadecane]-1'(10'),3',5',8',11'(15')-pentaene-13'-carboxamide | 1-cyclopropyl-methanamine | 4 | 478 | 0.66 |
| 69 | (13'S)-9'-(2-chlorophenyl)-3'-methyl-N-{spiro[2.5]octan-6-yl}-16'-thia-2',4',5',8'-tetraazaspiro[cyclopropane-1,7'-tetracyclo-[8.6.0.0²,⁶.0¹¹,¹⁵]hexadecane]-1'(10'),3',5',8',11'(15')-pentaene-13'-carboxamide | spiro[2.5]octan-6-amine | 4 | 532 | 0.83 |

| Ex. | Structure/Name | Amine Employed | LC-MS Method | MS (ESI+): m/z [M + H]+ | $t_R$ [min] |
|---|---|---|---|---|---|
| 70 | (13'S)-9'-(2-chlorophenyl)-N-[(1S,3R)-3-fluorocyclopentyl]-3'-methyl-16'-thia-2',4',5',8'-tetraazaspiro[cyclopropane-1,7'-tetracyclo-[8.6.0.0$^{2,6}$.0$^{11,15}$]hexadecane]-1'(10'),3',5',8',11'(15')-pentaene-13'-carboxamide | (1S,3R)-3-fluoro-cyclopentan-1-amine | 4 | 510 | 0.64 |
| 71 | (13'S)-9'-(2-chlorophenyl)-N-[1-(hydroxymethyl)-cyclohexyl]-3'-methyl-16'-thia-2',4',5',8'-tetraaza-spiro[cyclopropane-1,7'-tetracyclo-[8.6.0.0$^{2,6}$.0$^{11,15}$]hexadecane]-1'(10'),3',5',8',11'(15')-pentaene-13'-carboxamide | (1-aminocyclohexyl)-methanol | 4 | 536 | 0.67 |
| 72 | ethyl 4-{N-methyl[(13'S)-9'-(2-chlorophenyl)-3'-methyl-16'-thia-2',4',5',8'-tetraazaspiro-[cyclopropane-1,7'-tetracyclo[8.6.0.0$^{2,6}$.0$^{11,15}$]-hexadecane]-1'(10'),3',5',8',11'(15')-pentaen-13'-yl]amido}piperidine-1-carboxylate | ethyl 4-(methylamino)-piperidine-1-carboxylate | 4 | 593 | 0.71 |

-continued

| Ex. | Structure/Name | Amine Employed | LC-MS Method | MS (ESI+): m/z [M + H]+ | $t_R$ [min] |
|---|---|---|---|---|---|
| 73 | 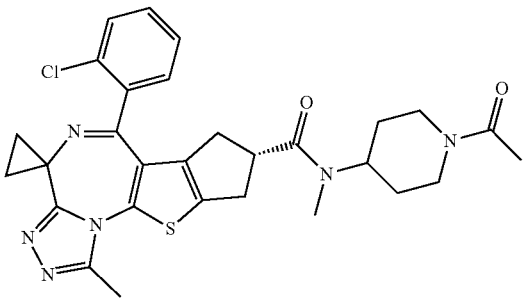 [SMILES: CC(=O)N1CCC(N(C)C(=O)[C@@H]2Cc3sc4c(c3C2)C(c2ccccc2Cl)=NC2(CC2)c2nnc(C)n2-4)CC1]<br>(13'S)-N-(1-acetylpiperidin-4-yl)-9'-(2-chlorophenyl)-N,3'-dimethyl-16'-thia-2',4',5',8'-tetraazaspiro[cyclopropane-1,7'-tetracyclo-[8.6.0.0$^{2,6}$.0$^{11,15}$]hexadecane]-1'(10'),3',5',8',11'(15')-pentaene-13'-carboxamide | 1-[4-(methylamino)-piperidin-1-yl]-ethan-1-one | 4 | 563 | 0.56 |
| 74 | 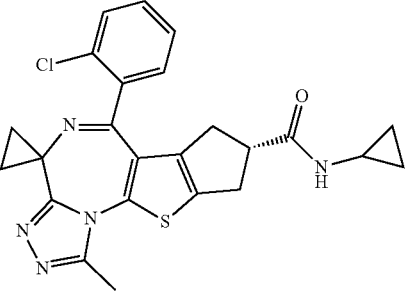 [SMILES: Cc1nnc2n1-c1sc3c(c1C(c1ccccc1Cl)=NC21CC1)C[C@H](C(=O)NC1CC1)C3]<br>(13'S)-9'-(2-chlorophenyl)-N-cyclopropyl-3'-methyl-16'-thia-2',4',5',8'-tetraazaspiro-[cyclopropane-1,7'-tetracyclo[8.6.0.0$^{2,6}$.0$^{11,15}$]-hexadecane]-1'(10'),3',5',8',11'(15')-pentaene-13'-carboxamide | cyclopropanamine | 4 | 464 | 0.57 |
| 75 | 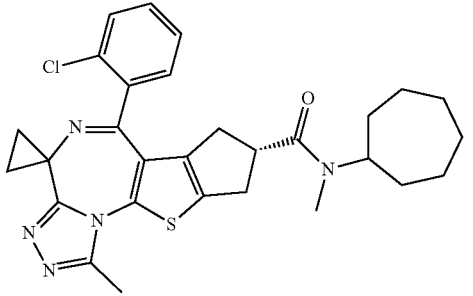 [SMILES: Cc1nnc2n1-c1sc3c(c1C(c1ccccc1Cl)=NC21CC1)C[C@H](C(=O)N(C)C1CCCCCC1)C3]<br>(13'S)-9'-(2-chlorophenyl)-N-cycloheptyl-N,3'-dimethyl-16'-thia-2',4',5',8'-tetraazaspiro-[cyclopropane-1,7'-tetracyclo[8.6.0.0$^{2,6}$.0$^{11,15}$]-hexadecane]-1'(10'),3',5',8',11'(15')-pentaene-13'-carboxamide | N-methyl-cycloheptanamine | 4 | 534 | 0.90 |

| Ex. | Structure/Name | Amine Employed | LC-MS Method | MS (ESI+): m/z [M + H]+ | $t_R$ [min] |
|---|---|---|---|---|---|
| 76 | 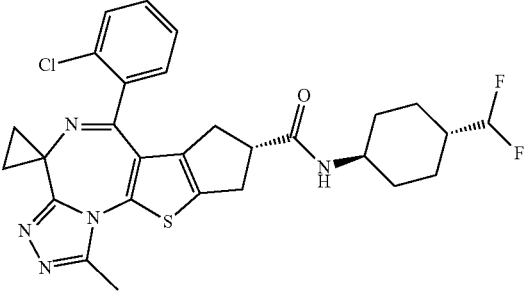 [SMILES: Cc1nnc2n1-c1sc3c(c1C(c1ccccc1Cl)=NC21CC1)C[C@H](C(=O)N[C@H]1CC[C@H](C(F)F)CC1)C3]<br>(13'S)-9'-(2-chlorophenyl)-3'-methyl-N-[(1r,4r)-4-(difluoromethyl)cyclohexyl]-16'-thia-2',4',5',8'-tetraazaspiro[cyclopropane-1,7'-tetracyclo-[8.6.0.0²,⁶.0¹¹,¹⁵]hexadecane]-1'(10'),3',5',8',11'(15')-pentaene-13'-carboxamide | (1r,4r)-4-(difluoromethyl)cyclohexan-1-amine | 4 | 556 | 0.75 |
| 77 | 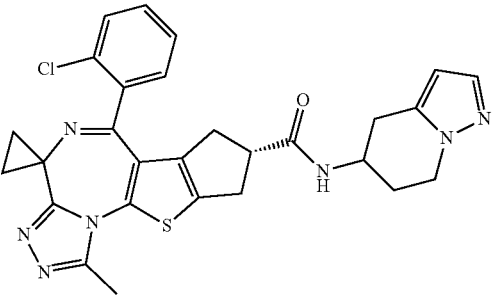 [SMILES: Cc1nnc2n1-c1sc3c(c1C(c1ccccc1Cl)=NC21CC1)C[C@H](C(=O)NC1CCn2nccc2C1)C3]<br>(13'S)-9'-(2-chlorophenyl)-3'-methyl-N-{4H,5H,6H,7H-pyrazolo[1,5-a]pyridin-5-yl}-16'-thia-2',4',5',8'-tetraazaspiro[cyclopropane-1,7'-tetracyclo[8.6.0.0²,⁶.0¹¹,¹⁵]hexadecane]-1'(10'),3',5',8',11'(15')-pentaene-13'-carboxamide | 4H,5H,6H,7H-pyrazolo[1,5-a]-pyridin-5-amine | 4 | 544 | 0.57 |
| 78 | 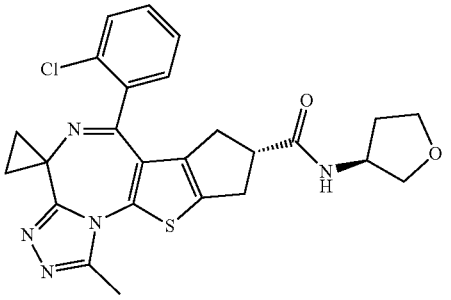 [SMILES: Cc1nnc2n1-c1sc3c(c1C(c1ccccc1Cl)=NC21CC1)C[C@H](C(=O)N[C@H]1CCOC1)C3]<br>(13'S)-9'-(2-chlorophenyl)-3'-methyl-N-[(3S)-oxolan-3-yl]-16'-thia-2',4',5',8'-tetraazaspiro-[cyclopropane-1,7'-tetracyclo[8.6.0.0²,⁶.0¹¹,¹⁵]-hexadecane]-1'(10'),3',5',8',11'(15')-pentaene-13'-carboxamide | (3S)-oxolan-3-amine | 4 | 494 | 0.53 |

-continued

| Ex. | Structure/Name | Amine Employed | LC-MS Method | MS (ESI+): m/z [M + H]+ | $t_R$ [min] |
|---|---|---|---|---|---|
| 79 | (13'S)-9'-(2-chlorophenyl)-N-(4,4-dimethyl-cyclohexyl)-N,3'-dimethyl-16'-thia-2',4',5',8'-tetraazaspiro[cyclopropane-1,7'-tetracyclo-[8.6.0.0$^{2,6}$.0$^{11,15}$]hexadecane]-1'(10'),3',5',8',11'(15')-pentaene-13'-carboxamide | N,4,4-trimethyl-cyclohexan-1-amine | 4 | 548 | 0.96 |
| 80 | (13'S)-9'-(2-chlorophenyl)-3'-methyl-N-{spiro[3.3]heptan-2-yl}-16'-thia-2',4',5',8'-tetraazaspiro[cyclopropane-1,7'-tetracyclo-[8.6.0.0$^{2,6}$.0$^{11,15}$]hexadecane]-1'(10'),3',5',8',11'(15')-pentaene-13'-carboxamide | spiro[3.3]heptan-2-amine | 4 | 518 | 0.81 |
| 81 | (13'S)-9'-(2-chlorophenyl)-N-ethyl-N-[(1R,2R)-2-hydroxy-2,3-dihydro-1H-inden-1-yl]-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | (1R,2R)-1-(ethylamino)-2,3-dihydro-1H-inden-2-ol | 4 | 584 | 0.73 |

| Ex. | Structure/Name | Amine Employed | LC-MS Method | MS (ESI+): m/z [M + H]+ | $t_R$ [min] |
|---|---|---|---|---|---|
| 82 | 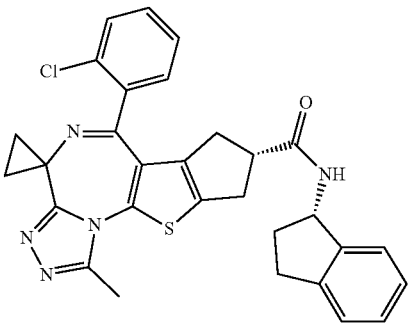 [SMILES: Cc1nnc2n1-c1sc3c(c1C(c1ccccc1Cl)=NC21CC1)C[C@H](C(=O)N[C@H]1CCc2ccccc21)C3]<br>(13'S)-9'-(2-chlorophenyl)-N-[(1S)-2,3-dihydro-1H-inden-1-yl]-3'-methyl-16'-thia-2',4',5',8'-tetraazaspiro[cyclopropane-1,7'-tetracyclo-[8.6.0.0$^{2,6}$.0$^{11,15}$]hexadecane]-1'(10'),3',5',8',11'(15')-pentaene-13'-carboxamide | (1S)-2,3-dihydro-1H-inden-1-amine | 4 | 540 | 0.67 |
| 83 | 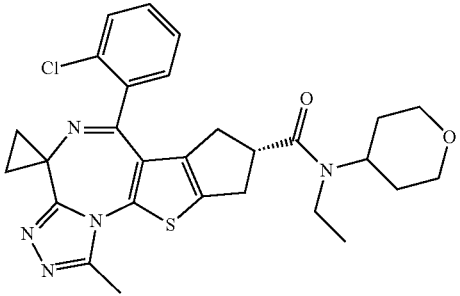 [SMILES: CCN(C(=O)[C@@H]1Cc2sc3c(c2C1)C(c1ccccc1Cl)=NC1(CC1)c1nnc(C)n1-3)C1CCOCC1]<br>(13'S)-9'-(2-chlorophenyl)-N-ethyl-3'-methyl-N-(oxan-4-yl)-16'-thia-2',4',5',8'-tetraazaspiro-[cyclopropane-1,7'-tetracyclo[8.6.0.0$^{2,6}$.0$^{11,15}$]-hexadecane]-1'(10'),3',5',8',11'(15')-pentaene-13'-carboxamide | N-ethyloxan-4-amine | 4 | 536 | 0.67 |
| 84 | 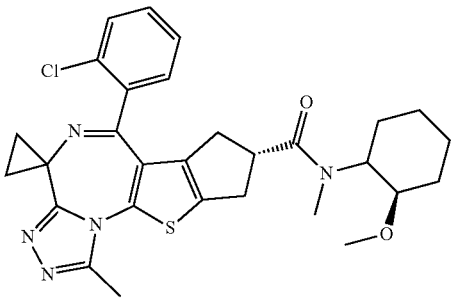 [SMILES: CO[C@@H]1CCCCC1N(C)C(=O)[C@@H]1Cc2sc3c(c2C1)C(c1ccccc1Cl)=NC1(CC1)c1nnc(C)n1-3]<br>(13'S)-9'-(2-chlorophenyl)-N-[(1R,2R)-2-methoxycyclohexyl]-N,3'-dimethyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | (1R,2R)-2-methoxy-N-methyl-cyclohexan-1-amine | 4 | 550 | 0.78 |

-continued

| Ex. | Structure/Name | Amine Employed | LC-MS Method | MS (ESI+): m/z [M + H]+ | $t_R$ [min] |
|---|---|---|---|---|---|
| 85 | (13'S)-9'-(2-chlorophenyl)-N-[1-(2-methoxy-pyridin-4-yl)cyclopropyl]-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | 1-(2-methoxypyridin-4-yl)cyclopropan-1-amine | 4 | 571 | 0.65 |
| 86 | (13'S)-9'-(2-chlorophenyl)-N-[(1S,2S)-2-hydroxy-1,2,3,4-tetrahydronaphthalen-1-yl]-N,3'-dimethyl-16'-thia-2',4',5',8'-tetraazaspiro-[cyclopropane-1,7'-tetracyclo[8.6.0.0$^{2,6}$.0$^{11,15}$]-hexadecane]-1'(10'),3',5',8',11'(15')-pentaene-13'-carboxamide | (1S,2S)-1-(methylamino)-1,2,3,4-tetrahydro-naphthalen-2-ol | 4 | 584 | 0.73 |
| 87 | (13'S)-9'-(2-chlorophenyl)-3'-methyl-N-[1-(pyridin-2-yl)cyclopropyl]-16'-thia-2',4',5',8'-tetraazaspiro[cyclopropane-1,7'-tetracyclo-[8.6.0.0$^{2,6}$.0$^{11,15}$]hexadecane]-1'(10'),3',5',8',11'(15')-pentaene-13'-carboxamide | 1-(pyridin-2-yl)-cyclopropan-1-amine | 4 | 541 | 0.63 |

-continued

| Ex. | Structure/Name | Amine Employed | LC-MS Method | MS (ESI+): m/z [M + H]+ | $t_R$ [min] |
|---|---|---|---|---|---|
| 88 | (13'S)-9'-(2-chlorophenyl)-3'-methyl-N-[(3R,4S)-4-(propan-2-yl)oxolan-3-yl]-16'-thia-2',4',5',8'-tetraazaspiro[cyclopropane-1,7'-tetracyclo-[8.6.0.0²,⁶.0¹¹,¹⁵]hexadecane]-1'(10'),3',5',8',11'(15')-pentaene-13'-carboxamide | (3R,4S)-4-(propan-2-yl)oxolan-3-amine | 4 | 536 | 0.69 |
| 89 | (13'S)-9'-(2-chlorophenyl)-N-(1,1-dioxo-1lambda6-thiolan-3-yl)-N,3'-dimethyl-16'-thia-2',4',5',8'-tetraazaspiro[cyclopropane-1,7'-tetracyclo[8.6.0.0²,⁶.0¹¹,¹⁵]hexadecane]-1'(10'),3',5',8',11'(15')-pentaene-13'-carboxamide | 3-(methylamino)-1lambda6-thiolane-1,1-dione | 4 | 556 | 0.55 |
| 90 | (13'S)-9'-(2-chlorophenyl)-3'-methyl-N-{8-oxabicyclo[3.2.1]octan-3-yl}-16'-thia-2',4',5',8'-tetraazaspiro[cyclopropane-1,7'-tetracyclo-[8.6.0.0²,⁶.0¹¹,¹⁵]hexadecane]-1'(10'),3',5',8',11'(15')-pentaene-13'-carboxamide | 8-oxabicyclo[3.2.1]-octan-3-amine | 4 | 534 | 0.58 |

-continued

| Ex. | Structure/Name | Amine Employed | LC-MS Method | MS (ESI+): m/z [M + H]+ | $t_R$ [min] |
| --- | --- | --- | --- | --- | --- |
| 91 | 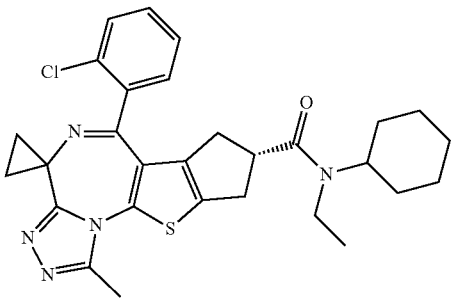 [SMILES: CCN(C(=O)[C@@H]1Cc2sc3c(c2C1)C(c1ccccc1Cl)=NC1(CC1)c1nnc(C)n1-3)C1CCCCC1]<br>(13'S)-9'-(2-chlorophenyl)-N-cyclohexyl-N-ethyl-3'-methyl-16'-thia-2',4',5',8'-tetraazaspiro-[cyclopropane-1,7'-tetracyclo[8.6.0.0$^{2,6}$.0$^{11,15}$]-hexadecane]-1'(10'),3',5',8',11'(15')-pentaene-13'-carboxamide | N-ethyl-cyclohexanamine | 4 | 534 | 0.92 |
| 92 | 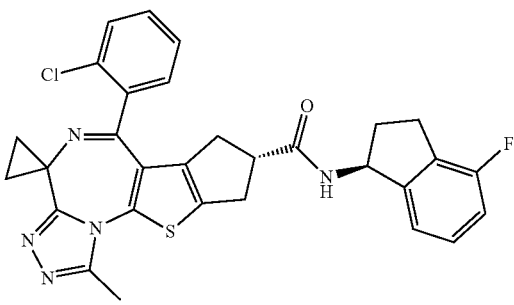 [SMILES: Cc1nnc2n1-c1sc3c(c1C(c1ccccc1Cl)=NC21CC1)C[C@H](C(=O)N[C@H]1CCc2c(F)cccc21)C3]<br>(13'S)-9'-(2-chlorophenyl)-N-[(1S)-4-fluoro-2,3-dihydro-1H-inden-1-yl]-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | (1S)-4-fluoro-2,3-dihydro-1H-inden-1-amine | 4 | 558 | 0.80 |
| 93 | 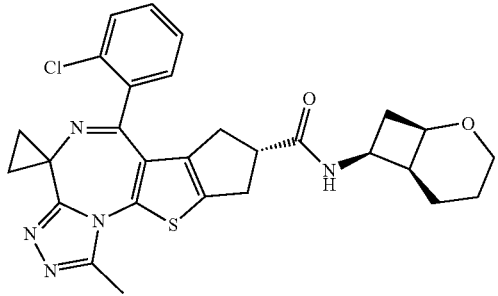 [SMILES: Cc1nnc2n1-c1sc3c(c1C(c1ccccc1Cl)=NC21CC1)C[C@H](C(=O)N[C@H]1C[C@H]2OCCC[C@@H]12)C3]<br>(13'S)-9'-(2-chlorophenyl)-3'-methyl-N-[(1R,6S,7S)-2-oxabicyclo[4.2.0]octan-7-yl]-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | (1R,6S,7S)-2-oxabicyclo[4.2.0]-octan-7-amine | 4 | 534 | 0.61 |

-continued

| Ex. | Structure/Name | Amine Employed | LC-MS Method | MS (ESI+): m/z [M + H]+ | $t_R$ [min] |
|---|---|---|---|---|---|
| 94 | (13'S)-9'-(2-chlorophenyl)-N-(6,6-dimethyloxan-3-yl)-3'-methyl-16'-thia-2',4',5',8'-tetraazaspiro-[cyclopropane-1,7'-tetracyclo[8.6.0.0²,⁶.0¹¹,¹⁵]-hexadecane]-1'(10'),3',5',8',11'(15')-pentaene-13'-carboxamide | 6,6-dimethyl-oxan-3-amine | 4 | 536 | 0.68 |
| 95 | (13'S)-9'-(2-chlorophenyl)-3'-methyl-N-[(3R)-oxolan-3-yl]-16'-thia-2',4',5',8'-tetraazaspiro-[cyclopropane-1,7'-tetracyclo[8.6.0.0²,⁶.0¹¹,¹⁵]-hexadecane]-1'(10'),3',5',8',11'(15')-pentaene-13'-carboxamide | (3R)-oxolan-3-amine | 4 | 494 | 0.53 |
| 96 | (13'S)-9'-(2-chlorophenyl)-3'-methyl-N-(4-phenyloxan-4-yl)-16'-thia-2',4',5',8'-tetraaza-spiro[cyclopropane-1,7'-tetracyclo-[8.6.0.0²,⁶.0¹¹,¹⁵]hexadecane]-1'(10'),3',5',8',11'(15')-pentaene-13'-carboxamide | 4-phenyl-oxan-4-amine | 4 | 584 | 0.72 |

-continued

| Ex. | Structure/Name | Amine Employed | LC-MS Method | MS (ESI+): m/z [M + H]+ | $t_R$ [min] |
|---|---|---|---|---|---|
| 97 | (13'S)-9'-(2-chlorophenyl)-3'-methyl-N-(5,6,7,8-tetrahydroquinolin-6-yl)-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | 5,6,7,8-tetrahydro-quinolin-6-amine | 4 | 553 | 0.60 |
| 98 | (13'S)-9'-(2-chlorophenyl)-3'-methyl-N-[(1r,4r)-4-(2-hydroxypropan-2-yl)cyclohexyl]-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | 2-[(1r,4r)-4-aminocyclohexyl]-propan-2-ol | 4 | 564 | 0.64 |
| 99 | (13'S)-9'-(2-chlorophenyl)-N-[(5R)-1-ethyl-4,5,6,7-tetrahydro-1H-indazol-5-yl]-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | (5R)-1-ethyl-4,5,6,7-tetrahydro-1H-indazol-5-amine | 4 | 572 | 0.62 |

-continued

| Ex. | Structure/Name | Amine Employed | LC-MS Method | MS (ESI+): m/z [M + H]+ | $t_R$ [min] |
|---|---|---|---|---|---|
| 100 | (13'S)-9'-(2-chlorophenyl)-N-[(5S)-1-ethyl-4,5,6,7-tetrahydro-1H-indazol-5-yl]-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | (5S)-1-ethyl-4,5,6,7-tetrahydro-1H-indazol-5-amine | 4 | 572 | 0.62 |
| 101 | (13'S)-9'-(2-chlorophenyl)-N-[(1R,2R,4R,5R)-5-ethyl-7-oxabicyclo[2.2.1]heptan-2-yl]-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | (1R,2R,4R,5R)-5-ethyl-7-oxabicyclo[2.2.1-]heptan-2-amine | 4 | 548 | 0.69 |
| 102 | (13'S)-9'-(2-chlorophenyl)-N-[(1S,2R)-2-hydroxycyclohexyl]-N,3'-dimethyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | (1R,2S)-2-(methylamino)-cyclohexan-1-ol | 4 | 536 | 0.68 |

| Ex. | Structure/Name | Amine Employed | LC-MS Method | MS (ESI+): m/z [M + H]+ | $t_R$ [min] |
|---|---|---|---|---|---|
| 103 | 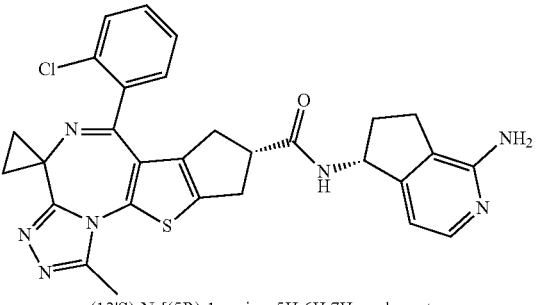<br>(13'S)-N-[(5R)-1-amino-5H,6H,7H-cyclopenta-[c]pyridin-5-yl]-9'-(2-chlorophenyl)-3'-methyl-16'-thia-2',4',5',8'-tetraazaspiro-[cyclopropane-1,7'-tetracyclo[8.6.0.0$^{2,6}$.0$^{11,15}$]-hexadecane]-1'(10'),3',5',8',11'(15')-pentaene-13'-carboxamide | (5R)-5H,6H,7H-cyclopenta[c]-pyridine-1,5-diamine | 4 | 556 | 0.54 |

Example 104

(13'S)-9'-(2-chlorophenyl)-3'-methyl-N, N-dipropyl-16'-thia-2',4',5',8'-tetraazaspiro[cyclopropane-1,7'-tetracyclo[8.6.0.0$^{2,6}$.0$^{11,15}$]hexadecane]-1'(10'),3',5', 8',11'(15')-pentaene-13'-carboxamide

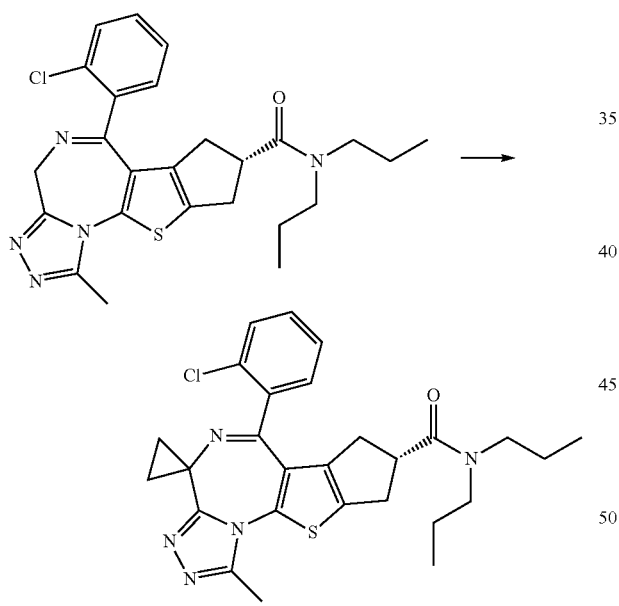

(2-Bromoethyl)diphenylsulfanium trifluoromethanesulfonate (184 mg) and KHMDS (1.0 M in THF; 830 NL) are added to (13S)-9-(2-chlorophenyl)-3-methyl-N,N-dipropyl-16-thia-2,4,5,8-tetraazatetracyclo[8.6.0.0$^{2,6}$.0$^{11,15}$]hexadeca-1(10),3,5,8,11(15)-pentaene-13-carboxamide (for synthesis see EP0388789A1; 100 mg) in DMSO (2 mL) at rt. The mixture is stirred at rt overnight. More (2-bromoethyl) diphenylsulfanium trifluoromethanesulfonate (184 mg) and KHMDS (1.0 M in THF; 830 NL) are added and stirring is continued for 2 h. The mixture is diluted with DMF, filtered, and chromatographed on reversed phase (HPLC; ACN/water/aqueous ammonia) to give the title compound.

LC-MS (Method 1): $t_R$=1.03 min; Mass spectrum (ESI+): m/z=508 [M+H]+.

Examples 105-118

Examples 105-118 compiled in the following table are obtained from (13'S)-9'-(2-chlorophenyl)-3'-methyl-16'-thia-2',4',5',8'-tetraazaspiro[cyclopropane-1,7'-tetracyclo[8.6.0.0²,⁶.0¹¹,¹⁵]hexadecane]-1'(10'),3',5',8',11'(15')-pentaene-13'-carboxylic acid (Intermediate 1) by following a procedure analogous to that described for Example 1.

| Ex. | Structure/Name | Amine Employed | LC-MS Method | MS (ESI+): m/z [M + H]⁺ | $t_R$ [min] |
|---|---|---|---|---|---|
| 105 | 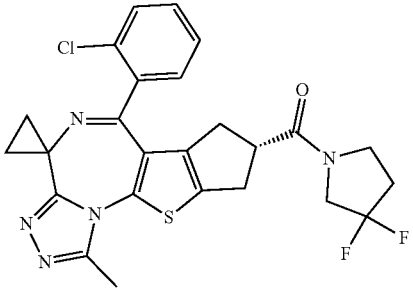 [SMILES: Cc1nnc2n1-c1sc3c(c1C(c1ccccc1Cl)=NC21CC1)C[C@H](C(=O)N1CCC(F)(F)C1)C3]<br>(13'S)-9'-(2-chlorophenyl)-13'-(3,3-difluoropyrrolidine-1-carbonyl)-3'-methyl-16'-thia-2',4',5',8'-tetraazaspiro[cyclopropane-1,7'-tetracyclo[8.6.0.0²,⁶.0¹¹,¹⁵]hexadecane]-1'(10'),3',5',8',11'(15')-pentaene | 3,3-difluoro-pyrrolidine | 3 | 514 | 0.69 |
| 106 | 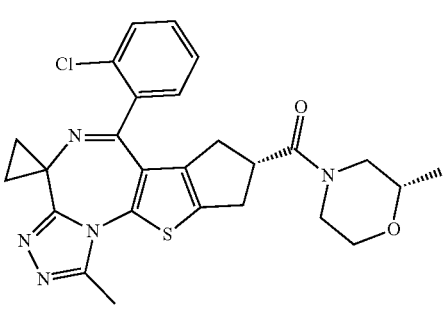 [SMILES: Cc1nnc2n1-c1sc3c(c1C(c1ccccc1Cl)=NC21CC1)C[C@H](C(=O)N1CCO[C@@H](C)C1)C3]<br>(13'S)-9'-(2-chlorophenyl)-3'-methyl-13'-[(2S)-2-methylmorpholine-4-carbonyl]-16'-thia-2',4',5',8'-tetraazaspiro[cyclopropane-1,7'-tetracyclo-[8.6.0.0²,⁶.0¹¹,¹⁵]hexadecane}-1'(10'),3',5',8',11'(15')-pentaene | (2S)-2-methyl-morpholine | 3 | 508 | 0.64 |
| 107 | 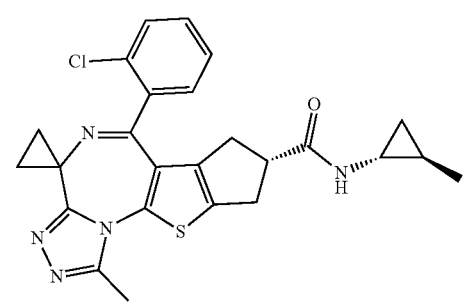 [SMILES: Cc1nnc2n1-c1sc3c(c1C(c1ccccc1Cl)=NC21CC1)C[C@H](C(=O)N[C@@H]1C[C@H]1C)C3]<br>(13'S)-9'-(2-chlorophenyl)-3'-methyl-N-[(1R,2R)-2-methylcyclopropyl]-16'-thia-2',4',5',8'-tetraazaspiro[cyclopropane-1,7'-tetracyclo-[8.6.0.0²,⁶.0¹¹,¹⁵]hexadecane]-1'(10'),3',5')8',11'(15')-pentaene-13'-carboxamide | (1R,2R)-2-methyl-cyclopropan-1-amine | 1<br>Chiral SFC: 7 | 478<br>478.0 | 0.88<br>3.97 |

| Ex. | Structure/Name | Amine Employed | LC-MS Method | MS (ESI+): m/z [M + H]+ | $t_R$ [min] |
|---|---|---|---|---|---|
| 108 | 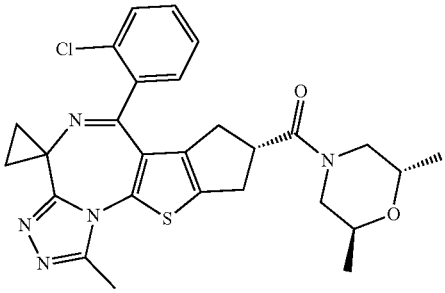 [SMILES: Cc1nnc2n1-c1sc3c(c1C(c1ccccc1Cl)=NC21CC1)C[C@H](C(=O)N1C[C@H](C)O[C@@H](C)C1)C3]<br>(13'S)-9'-(2-chlorophenyl)-13'-[(2S,6S)-2,6-dimethylmorpholine-4-carbonyl]-3'-methyl-16'-thia-2',4',5',8'-tetraazaspiro[cyclopropane-1,7'-tetracyclo[8.6.0.0²,⁶.0¹¹,¹⁵]hexadecane]-1'(10'),3',5',8',11'(15')-pentaene | (2S,6S)-2,6-dimethylmorpholine | 5 | 522 | 0.89 |
| 109 | 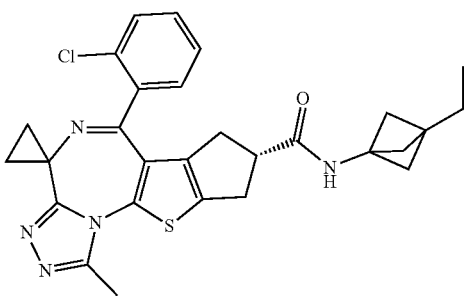 [SMILES: CCC12CC(NC(=O)[C@@H]3Cc4sc5c(c4C3)C(c3ccccc3Cl)=NC3(CC3)c3nnc(C)n3-5)(C1)C2]<br>(13'S)-9'-(2-chlorophenyl)-N-{3-ethylbicyclo-[1.1.1]pentan-1-yl}-3'-methyl-16'-thia-2',4',5',8'-tetraazaspiro[cyclopropane-1,7'-tetracyclo-[8.6.0.0²,⁶.0¹¹,¹⁵]hexadecane]-1'(10'),3',5'), 8',11'(15')-pentaene-13'-carboxamide | 3-ethylbicyclo[1.1.1]-pentan-1-amine | 3 | 518 | 0.83 |
| 110 | 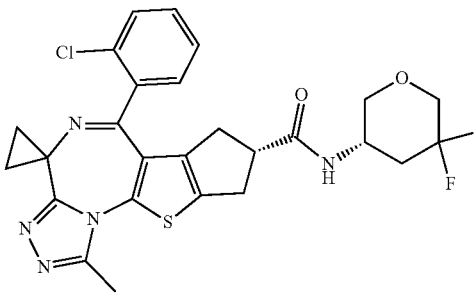<br>(13'S)-9'-(2-chlorophenyl)-N-[(3S)-5,5-difluorooxan-3-yl]-3'-methyl-16'-thia-2',4',5',8'-tetraazaspiro[cyclopropane-1,7'-tetracyclo-[8.6.0.0²,⁶.0¹¹,¹⁵]hexadecane]-1'(10'),3',5') 8',11'(15')-pentaene-13'-carboxamide | (3S)-5,5-difluoro-oxan-3-amine | 1<br>Chiral SFC: 8 | 544<br>544.2 | 0.88<br>5.61 |

| Ex. | Structure/Name | Amine Employed | LC-MS Method | MS (ESI+): m/z [M + H]+ | $t_R$ [min] |
|---|---|---|---|---|---|
| 111 | (13'S)-9'-(2-chlorophenyl)-N-[(3S)-1-methanesulfonylpyrrolidin-3-yl]-N,3'-dimethyl-16'-thia-2',4',5',8'-tetraazaspiro[cyclopropane-1,7'-tetracyclo[8.6.0.0²,⁶.0¹¹,¹⁵]hexadecane]-1'(10'),3',5',8',11'(15')-pentaene-13'-carboxamide | (3S)-1-methanesulfonyl-N-methylpyrrolidin-3-amine | 4 | 585 | 0.58 |
| 112 | (13'S)-9'-(2-chlorophenyl)-N,3'-dimethyl-N-[(1r,4r)-4-hydroxycyclohexyl]-16'-thia-2',4',5',8'-tetraazaspiro[cyclopropane-1,7'-tetracyclo-[8.6.0.0²,⁶.0¹¹,¹⁵]hexadecane]-1'(10'),3',5') 8',11'(15')-pentaene-13'-carboxamide | (1r,4r)-4-(methylamino)-cyclohexan-1-ol | 4 | 536 | 0.57 |
| 113 | (13'S)-9'-(2-chlorophenyl)-3'-methyl-N-[(1r,3r)-3-methanesulfonylcyclobutyl]-16'-thia-2',4',5',8'-tetraazaspiro[cyclopropane-1,7'-tetracyclo-[8.6.0.0²,⁶.0¹¹,¹⁵]hexadecane]-1'(10'),3',5') 8',11'(15')-pentaene-13'-carboxamide | (1r,3r)-3-methanesulfonyl-cyclobutan-1-amine | 4 | 556 | 0.56 |

-continued

| Ex. | Structure/Name | Amine Employed | LC-MS Method | MS (ESI+): m/z [M + H]+ | $t_R$ [min] |
|---|---|---|---|---|---|
| 114 | (13'S)-9'-(2-chlorophenyl)-3'-methyl-13'-(morpholine-4-carbonyl)-16'-thia-2',4',5',8'-tetraazaspiro[cyclopropane-1,7'-tetracyclo-[8.6.0.0$^{2,6}$.0$^{11,15}$]hexadecane]-1'(10'),3',5')8',11'(15')-pentaene | morpholine | 5 | 494 | 0.83 |
| 115 | (13'S)-9'-(2-chlorophenyl)-3'-methyl-N-(oxan-4-yl)-N-propyl-16'-thia-2',4',5',8'-tetraazaspiro-[cyclopropane-1,7'-tetracyclo[8.6.0.0$^{2,6}$.0$^{11,15}$]hexadecane]-1'(10'),3',5',8',11'(15')-pentaene-13'-carboxamide | N-propyl-oxan-4-amine | 4 | 550 | 0.74 |
| 116 | (13'S)-9'-(2-chlorophenyl)-N-[(3R)-5,5-difluorooxan-3-yl]-3'-methyl-16'-thia-2',4',5',8'-tetraazaspiro[cyclopropane-1,7'-tetracyclo-[8.6.0.0$^{2,6}$.0$^{11,15}$]hexadecane]-1'(10'),3',5')8',11'(15')-pentaene-13'-carboxamide | (3R)-5,5-difluoro-oxan-3-amine | 1 Chiral SFC: 8 | 544 544.1 | 0.88 6.56 |

-continued

| Ex. | Structure/Name | Amine Employed | LC-MS Method | MS (ESI+): m/z [M + H]+ | $t_R$ [min] |
|---|---|---|---|---|---|
| 117 | 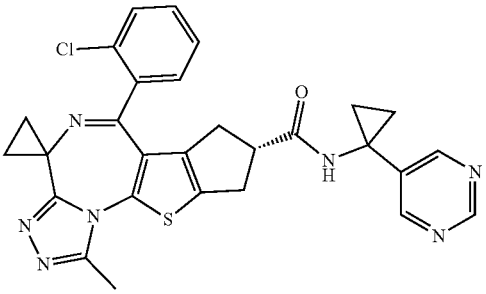 [SMILES: Cc1nnc2n1-c1sc3c(c1C(c1ccccc1Cl)=NC21CC1)C[C@H](C(=O)NC1(c2cncnc2)CC1)C3]<br>(13'S)-9'-(2-chlorophenyl)-3'-methyl-N-[1-(pyrimidin-5-yl)cyclopropyl]-16'-thia-2',4',5',8'-tetraazaspiro[cyclopropane-1,7'-tetracyclo-[8.6.0.0$^{2,6}$.0$^{11,15}$]hexadecane]-1'(10'),'3,5')8',11'(15')-pentaene-13'-carboxamide | 1-(pyrimidin-5-yl)-cyclopropan-1-amine | 4 | 542 | 0.52 |
| 118 | 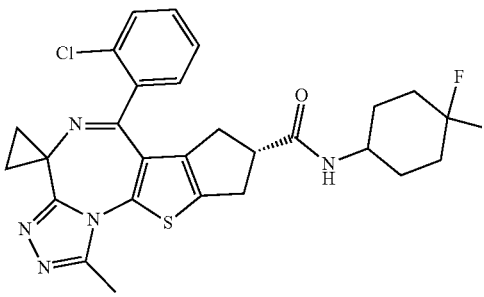<br>(13'S)-9'-(2-chlorophenyl)-N-(4,4-difluoro-cyclohexyl)-3'-methyl-16'-thia-2',4',5',8'-tetraazaspiro[cyclopropane-1,7'-tetracyclo-[8.6.0.0$^{2,6}$.0$^{11,15}$]hexadecane]-1'(10'),3',5')8',11'(15')-pentaene-13'-carboxamide | 4,4-difluoro-cyclohexan-1-amine | 1 | 542 | 0.97 |

Example 119

(13'S)-9'-(2-chlorophenyl)-3'-ethyl-13'-(morpholine-4-carbonyl)-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene

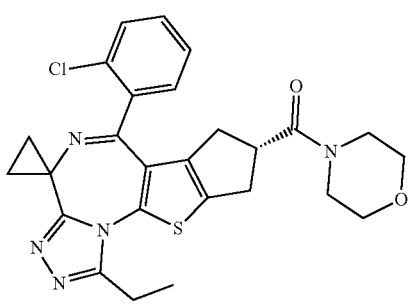 [SMILES: CCc1nnc2n1-c1sc3c(c1C(c1ccccc1Cl)=NC21CC1)C[C@H](C(=O)N1CCOCC1)C3]

n-Butyllithium (1.6 M in hexane; 76 μL) is added to diisopropylamine (19 μL) in THF (1 mL) at −78° C. After stirring for min, (13'S)-9'-(2-chlorophenyl)-3'-methyl-13'-(morpholine-4-carbonyl)-16'-thia-2',4',5',8'-tetraazaspiro[cyclo-propane-1,7'-tetracyclo[8.6.0.0$^{2,6}$.0$^{11,15}$]hexade-cane]-1'(10'),3',5',8',11'(15')-pentaene (Example 114; 50 mg) in THF (1 mL) is added and the mixture is stirred at −78° C. for 30 min. Iodomethane (7 μL) is added and the mixture is stirred at −78° C. for 1 h. The reaction is quenched with aq. NH$_4$Cl solution and the resulting mixture is extracted with EtOAc. The combined organic extract is dried (Na$_2$SO$_4$) and concentrated. The residue is chromatographed on reversed phase (HPLC; ACN/water/aqueous ammonia) to give the title compound.

LC-MS (Method 1): $t_R$=0.87 min; Mass spectrum (ESI+): m/z=508 [M+H]+.

Chiral SFC (Method 6): $t_R$=5.41 min; Mass spectrum (ESI+): m/z=508.2 [M+H]+.

Example 120

(13'S)-3'-methyl-13'-(morpholine-4-carbonyl)-9'-phenyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene

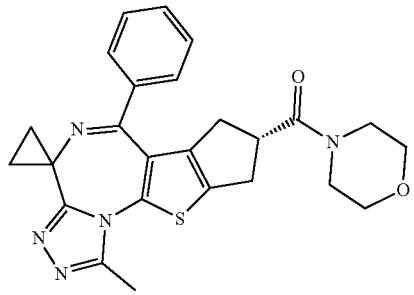 [SMILES: Cc1nnc2n1-c1sc3c(c1C(c1ccccc1)=NC21CC1)C[C@H](C(=O)N1CCOCC1)C3]

Raney nickel (75.0 mg) is added to (13'S)-9'-(2-chlorophenyl)-3'-methyl-13'-(morpholine-4-carbonyl)-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene (Example 114; 75 mg) in MeOH (8 mL) at rt. The mixture is shaken under an atmosphere of hydrogen (50 psi) at 50° C. for 6 d.

The mixture is filtered and the filtrate is concentrated. The residue is chromatographed on reversed phase (HPLC; ACN/water/aqueous TFA) to give the title compound.

LC-MS (Method 1): $t_R$=0.72 min; Mass spectrum (ESI$^+$): m/z=460 [M+H]$^+$.

Examples 121-129

Examples 121-129 compiled in the following table are obtained from (13'S)-9'-(2-chlorophenyl)-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxylic acid (Intermediate 1) by following a procedure analagous to that described for Example 1

| Ex. | Structure/Name | Amine Employed | LC-MS Method | MS (ESI+): m/z [M + H]$^+$ | $t_R$ [min] |
|---|---|---|---|---|---|
| 121 | (13'S)-9'-(2-chlorophenyl)-N-(1,1-dioxo-1lambda6-thian-3-yl)-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | 3-amino-1lambda6-thiane-1,1-dione | 4 | 556 | 0.52 |
| 122 | (13'S)-9'-(2-chlorophenyl)-N-[1-(2-hydroxypropan-2-yl)cyclopropyl]-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene-13'-carboxamide | 2-(1-aminocyclopropyl)-propan-2-ol | 4 | 522 | 0.58 |

| Ex. | Structure/Name | Amine Employed | LC-MS Method | MS (ESI+): m/z [M + H]+ | $t_R$ [min] |
|---|---|---|---|---|---|
| 123 | (13'S)-9'-(2-chlorophenyl)-13'-[(2R,6R)-2,6-dimethylmorpholine-4-carbonyl]-3'-methyl-16'-thia-2',4',5',8'-tetraazaspiro[cyclopropane-1,7'-tetracyclo[8.6.0.0²,⁶.0¹¹,¹⁵]hexadecane]-1'(10'),3',5',8',11'(15')-pentaene | (2R,6R)-2,6-dimethylmorpholine | 5 | 522 | 0.89 |
| 124 | (13'S)-9'-(2-chlorophenyl)-N-[(1R)-3,3-difluorocyclopentyl]-3'-methyl-16'-thia-2',4',5',8'-tetraazaspiro[cyclopropane-1,7'-tetracyclo-[8.6.0.0²,⁶0¹¹,¹⁵]hexadecane]-1'(10'),3',5')8',11'(15')-pentaene-13'-carboxamide | (1R)-3,3-difluoro-cyclopentan-1-amine | 3 | 528 | 0.70 |
| 125 | (13'S)-9'-(2-chlorophenyl)-N-[(2S)-1-fluoropropan-2-yl]-3'-methyl-16'-thia-2',4',5',8'-tetraazaspiro[cyclopropane-1,7'-tetracyclo-[8.6.0.0²,⁶.0¹¹,¹⁵]hexadecane]-1'(10'),3',5')8',11'(15')-pentaene-13'-carboxamide | (2S)-1-fluoro-propan-2-amine | 3 | 484 | 0.62 |

| Ex. | Structure/Name | Amine Employed | LC-MS Method | MS (ESI+): m/z [M + H]+ | $t_R$ [min] |
|---|---|---|---|---|---|
| 126 | (13'S)-9'-(2-chlorophenyl)-3'-methyl-13'-{5-oxa-2-azaspiro[3.4]octane-2-carbonyl}-16'-thia-2',4',5',8'-tetraazaspiro[cyclopropane-1,7'-tetracyclo[8.6.0.0²,⁶.0¹¹,¹⁵]hexadecane]-1'(10'),3',5',8',11'(15')-pentaene | 5-oxa-2-azaspiro[3.4]octane | 3 | 520 | 0.64 |
| 127 | (13'S)-9'-(2-chlorophenyl)-3'-methyl-13'-{7-oxa-4-azaspiro[2.5]octane-4-carbonyl}-16'-thia-2',4',5',8'-tetraazaspiro[cyclopropane-1,7'-tetracyclo[8.6.0.0²,⁶.0¹¹,¹⁵]hexadecane]-1'(10'),3',5',8',11'(15')-pentaene | 7-oxa-4-azaspiro[2.5]octane | 3 | 520 | 0.64 |
| 128 | (13'S)-9'-(2-chlorophenyl)-N-(3,5-dimethyl-1,2-oxazol-4-yl)-3'-methyl-16'-thia-2',4',5',8'-tetraazaspiro[cyclopropane-1,7'-tetracyclo[8.6.0.0²,⁶.0¹¹,¹⁵]hexadecane]-1'(10'),3',5')8',11'(15')-pentaene-13'-carboxamide | dimethyl-1,2-oxazol-4-amine | 3 | 520 | 0.60 |

-continued

| Ex. | Structure/Name | Amine Employed | LC-MS Method | MS (ESI+): m/z [M + H]+ | $t_R$ [min] |
|---|---|---|---|---|---|
| 129 | 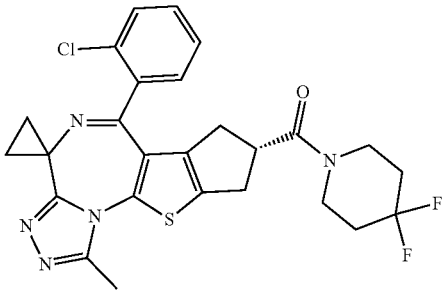 [SMILES: Cc1nnc2n1-c1sc3c(c1C(c1ccccc1Cl)=NC21CC1)C[C@H](C(=O)N1CCC(F)(F)CC1)C3](13'S)-9'-(2-chlorophenyl)-13'-(4,4-difluoropiperidine-1-carbonyl)-3'-methyl-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene | 4,4-difluoro-piperidine | 3 | 528 | 0.73 |

Example 130

(13'S)-9'-(2-methoxyphenyl)-3'-methyl-13'-(morpholine-4-carbonyl)-16'-thia-2',4',5',8'-tetraazaspiro[cyclopropane-1,7'-tetracyclo[8.6.0.0$^{2,6}$.0$^{11,15}$]hexadecane]-1'(10'),3',5',8',11'(15')-pentaene

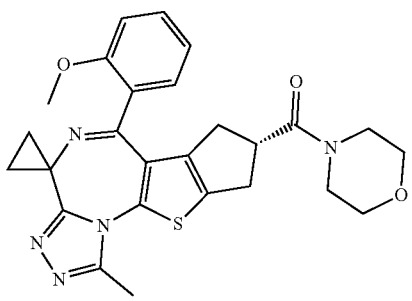 [SMILES: COc1ccccc1C1=NC2(CC2)c2nnc(C)n2-c2sc3c(c21)C[C@H](C(=O)N1CCOCC1)C3]

Sodium methoxide (25 wt % in methanol; 53.0 mg) is added to (13'S)-9'-(2-chlorophenyl)-3'-methyl-13'-(morpholine-4-carbonyl)-16'-thia-2',4',5',8'-tetraazaspiro[cyclopropane-1,7'-tetracyclo[8.6.0.0$^{2,6}$.0$^{11,15}$]hexadecane]-1'(10'),3',5',8', 11'(15')-pentaene (Example 114; 80 mg) in toluene (1 mL). The mixture is purged with Ar prior to the addition of Pd$_2$(dba)$_3$ (7.5 mg) and Tol-BINAP (13.5 mg). The mixture is stirred at 130° C. for 2 h and then concentrated in vacuo. The residue is chromatographed on reversed phase (HPLC; ACN/water/aqueous TFA) to give the title compound as a mixture with its enantiomer (ca. 3:1).

LC-MS (Method 1): $t_R$=0.72 min; Mass spectrum (ESI+): m/z=490 [M+H]+.

Chiral SFC [column: Chiral Art® Amylose-SA (4.6 mm×250 mm, 5 μm); column temperature: 40° C.; flow rate: 4.0 mL/min; BPR: 2175 bar; isocratic conditions: 75:25 CO$_2$:IPA (20 mM NH$_3$)]: $t_R$=4.72 min; Mass spectrum (ESI+): m/z=490.2 [M+H]+.

The invention claimed is:
1. A compound of formula (I)

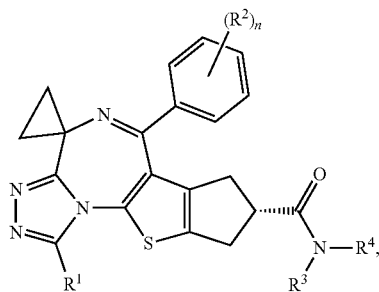

wherein
R$^1$ is selected from the group consisting of C$_{1-4}$-alkyl and C$_{3-4}$-cycloalkyl,
wherein the C$_{1-4}$-alkyl group of R$^1$ is optionally substituted with 1 to 3 F;
n is selected from the group consisting of 0, 1, 2, and 3;
R$^2$ is independently selected from the group consisting of F, Cl, Br, I, C$_{1-4}$-alkyl, C$_{3-4}$-cycloalkyl, —CN, —CONH$_2$, —CONH(C$_{1-4}$-alkyl), —CON(C$_{1-4}$-alkyl)$_2$, —COOH, —COO—C$_{1-4}$-alkyl, NH$_2$, OH, —O—C$_{1-4}$-alkyl, and —S(O)$_r$-C$_{1-4}$-alkyl with r=0, 1, or 2;
wherein the C$_{1-4}$-alkyl group of R$^2$ is optionally substituted with 1 to 3 F or with 1 —CN, with 1 OH, or with 1 O—C$_{1-4}$-alkyl, and
wherein the —O—C$_{1-4}$-alkyl group of R$^2$ is optionally substituted with 1 to 3 F;
R$^3$ is selected from the group consisting of H and C$_{1-4}$-alkyl optionally substituted with 1 to 5 F; and
R$^4$ is selected from the group consisting of C$_{1-6}$-alkyl optionally substituted with 1 to 3 F or optionally substituted with 1 to 2 substituents independently selected from
—CN, —CONH$_2$, —CONH(C$_{1-4}$-alkyl), —CON(C$_{1-4}$-alkyl)$_2$, —COOH, —COO—C$_{1-4}$-alkyl, C$_{1-3}$-alkyl-CO—NH—, C$_{1-3}$-alkyl-S(=O)$_2$—NH—, OH, and —O—C$_{1-3}$-alkyl optionally substituted with 1 to 3 F;

or $R^4$ is selected from the group consisting of —$C_{0-3}$-alkylene-$C_{3-10}$-cycloalkyl and —$C_{0-3}$-alkylene-$C_{3-10}$-heterocyclyl, wherein said alkylene moiety of the —$C_{0-3}$-alkylene-$C_{3-10}$-cycloalkyl and —$C_{0-3}$-alkylene-$C_{3-10}$-heterocyclyl groups of $R^4$ is optionally substituted with 1 to 2 substituents selected from F and $CH_3$, wherein 1 $CH_2$ group of said alkylene moiety of the —$C_{0-3}$-alkylene-$C_{3-10}$-cycloalkyl and —$C_{0-3}$-alkylene-$C_{3-10}$-heterocyclyl groups of $R^4$ is optionally replaced by a

moiety, wherein said cycloalkyl moiety of the —$C_{0-3}$-alkylene-$C_{3-10}$-cycloalkyl group of $R^4$ and said heterocyclyl moiety of the —$C_{0-3}$-alkylene-$C_{3-10}$-heterocyclyl group of $R^4$ are saturated mono- or bicyclic ring systems, wherein said heterocyclyl moiety of the —$C_{0-3}$-alkylene-$C_{3-10}$-heterocyclyl group of $R^4$ contains 1 to 2 ring members independently selected from N, NH, N($C_{1-4}$-alkyl), NCO($C_{1-4}$-alkyl), NCOO($C_{1-4}$-alkyl), NS(=O)$_2$($C_{1-4}$-alkyl), N-phenyl, N-pyridinyl, N-pyrimidinyl, and O, and optionally 1 ring member selected from C=O, and S(=O)$_r$, with r=0, 1, or 2, provided that said heterocyclyl moiety of the —$C_{0-3}$-alkylene-$C_{3-10}$-heterocyclyl group of $R^4$ does not contain any heteroatom-heteroatom bonds other than N—N, N—O, and N—S(=O)$_{r=1,2}$ between ring members, and wherein said cycloalkyl moiety of the —$C_{0-3}$-alkylene-$C_{3-10}$-cycloalkyl group of $R^4$ and said heterocyclyl moiety of the —$C_{0-3}$-alkylene-$C_{3-10}$-heterocyclyl group of $R^4$ are optionally substituted with 1 to 2 F and optionally substituted with 1 to 2 substituents independently selected from a) Cl,
b) —CN,
c) —$CONH_2$,
d) —CONH($C_{1-4}$-alkyl),
e) —CON($C_{1-4}$-alkyl)$_2$,
f) —COOH,
g) —COO—$C_{1-4}$-alkyl,
h) OH,
i) —O—$C_{1-3}$-alkyl optionally substituted with 1 to 3 F,
j) S(=O)$_2$—$C_{1-4}$-alkyl and
k) $C_{1-4}$-alkyl optionally substituted with 1 to 3 F or with 1 substituent selected from —CN, OH, —O—$C_{1-4}$-alkyl;

or $R^4$ is selected from the group consisting of —$C_{0-3}$-alkylene-phenyl and —$C_{0-3}$-alkylene-heteroaryl, wherein said alkylene moiety of the —$C_{0-3}$-alkylene-phenyl and —$C_{0-3}$-alkylene-heteroaryl groups of $R^4$ is optionally substituted with 1 to 2 substituents selected from F and $CH_3$, wherein 1 $CH_2$ group of said alkylene moiety of the —$C_{0-3}$-alkylene-phenyl and —$C_{0-3}$-alkylene-heteroaryl groups of $R^4$ is optionally replaced by a

moiety or by a

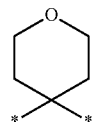

moiety, or wherein 1 —$CH_2$—$CH_2$— group of said alkylene moiety of the —$C_{0-3}$-alkylene-phenyl and —$C_{0-3}$-alkylene-heteroaryl groups of $R^4$ is optionally replaced by a

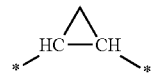

moiety or by a

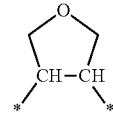

moiety, wherein said heteroaryl moiety of the —$C_{0-3}$-alkylene-heteroaryl group of $R^4$ is a 5-membered monocycle containing 1 ring member selected from N, NH, O, and S and optionally further containing 1 to 2 ring members N, or a 6-membered monocycle containing 1 to 2 ring members N, and wherein said phenyl moiety of the —$C_{0-3}$-alkylene-phenyl group of $R^4$ and said heteroaryl moiety of the —$C_{0-3}$-alkylene-heteroaryl group of $R^4$ are optionally substituted with 1 to 3 substituents independently selected from a) F, Cl, Br,
b) $C_{3-4}$-cycloalkyl,
c) —CN,
d) —$CONH_2$,
e) —CONH($C_{1-4}$-alkyl),
f) —CON($C_{1-4}$-alkyl)$_2$,
g) —COOH,
h) —COO—$C_{1-4}$-alkyl,
i) —NHCO—$C_{1-4}$-alkyl,
j) —NHS(=O)$_2$—$C_{1-4}$-alkyl,
k) —S(=O)$_r$-$C_{1-4}$-alkyl with r=0, 1, or 2,
l) —O—$C_{1-4}$-alkyl optionally substituted with 1 to 3 F, and
m) $C_{1-4}$-alkyl optionally substituted with 1 to 3 F or with 1 substituent selected from —CN, OH, and —O—$C_{1-4}$-alkyl, or $R^4$ is selected from the group consisting of 7- to 12-membered fused bicyclic aryl, heteroaryl, or heterocyclyl wherein said bicyclic aryl, heteroaryl, or heterocyclyl of $R^4$ consists of one non-aromatic ring that is attached to the amide N atom in formula (I) and optionally contains 1 to 2 ring members independently selected from N—, NH, N($C_{1-4}$-alkyl), N(CO—$C_{1-3}$-alkyl), N(S(=O)$_2$-$C_{1-3}$-alkyl), and O, and optionally contains 1 ring member selected from C=O and S(=O)$_r$, with r=0, 1, or 2, and of one aromatic ring selected from phenyl, pyrrole, furan, and thiophene in each of which 1 to 2 CH ring members are optionally replaced with N,
wherein said bicyclic aryl, heteroaryl, or heterocyclyl of $R^4$ is optionally substituted with 1 to 4 F,
is optionally substituted with 1 to 4 $C_{1-3}$-alkyl optionally substituted with 1 to 4 F, and
is optionally substituted with 1 to 2 substituents selected from the group consisting of Cl, —CN, —CONH$_2$, —CONH($C_{1-4}$-alkyl), —CON($C_{1-4}$-alkyl)$_2$, —COOH, —COO—$C_{1-4}$-alkyl, HO—$C_{1-3}$-alkylene-, $C_{1-3}$-alkyl-O—$C_{1-3}$-alkylene-, NH$_2$, $C_{1-3}$-alkyl-CO—NH—, $C_{1-3}$-alkyl-S(=O)$_2$-NH—, OH, and $C_{1-3}$-alkyl-O— optionally substituted with 1 to 3 F;

or $R^3$ and $R^4$ are selected from the group in which $R^3$ and $R^4$, together with the amide N atom they are attached to, form a saturated 3- to 8-membered monocyclic heterocyclyl optionally further containing 1 to 2 ring members independently selected from NH, N($C_{1-4}$-alkyl), N(CO—$C_{1-3}$-alkyl), N(S(=O)$_2$-$C_{1-3}$-alkyl), and O, and optionally containing 1 ring member selected from C=O and S(=O)$_r$, with r=0, 1, or 2, provided that said saturated 3- to 8-membered monocyclic heterocyclyl formed by $R^3$ and $R^4$ together with the amide N atom they are attached to does not contain any heteroatom-heteroatom bonds other than N—N, N—O, and N—S(=O)$_{r=1,2}$ between ring members,
wherein said heterocyclyl formed by $R^3$ and $R^4$ together with the amide N atom they are attached to is optionally substituted with 1 to 4 F,
is optionally substituted with 1 to 4 $C_{1-3}$-alkyl optionally substituted with 1 to 3 F, and
is optionally substituted with 1 to 2 substituents selected from Cl, —CN, —CONH$_2$, —CONH($C_{1-4}$-alkyl), —CON($C_{1-4}$-alkyl)$_2$, —COOH, —COO—$C_{1-4}$-alkyl, HO—$C_{1-3}$-alkylene-, $C_{1-3}$-alkyl-O—$C_{1-3}$-alkylene-, $C_{1-3}$-alkyl-CO—NH—, $C_{1-3}$-alkyl-S(=O)$_2$—NH—, OH, and $C_{1-3}$-alkyl-O— optionally substituted with 1 to 3 F;

or $R^3$ and $R^4$ are selected from the group in which $R^3$ and $R^4$, together with the amide N atom they are attached to, form a saturated 5- to 12-membered bicyclic heterocyclyl optionally further containing 1 to 3 ring members independently selected from N—, NH, N($C_{1-4}$-alkyl), N(CO—$C_{1-3}$-alkyl), N(S(=O)$_2$—$C_{1-3}$-alkyl), and O, and optionally containing 1 ring member selected from C=O and S(=O)$_r$, with r=0, 1, or 2, provided that said saturated 5- to 12-membered bicyclic heterocyclyl formed by $R^3$ and $R^4$ together with the amide N atom they are attached to does not contain any heteroatom-heteroatom bonds other than N—N, N—O, and N—S(=O)$_{r=1,2}$ between ring members wherein said saturated 5- to 12-membered bicyclic heterocyclyl formed by $R^3$ and $R^4$ together with the amide N atom they are attached to is optionally substituted with 1 to 6 F,
is optionally substituted with 1 to 4 $C_{1-3}$-alkyl optionally substituted with 1 to 3 F, or is optionally substituted with 1 to 2 substituents selected from Cl, —CN, —CONH$_2$, —CONH($C_{1-4}$-alkyl), —CON($C_{1-4}$-alkyl)$_2$, —COOH, —COO—$C_{1-4}$-alkyl, HO—$C_{1-3}$-alkylene-, $C_{1-3}$-alkyl-O—$C_{1-3}$-alkylene-, $C_{1-3}$-alkyl-CO—NH—, $C_{1-3}$-alkyl-S(=O)$_2$-NH—, OH, and $C_{1-3}$-alkyl-O—;

or a salt thereof.

2. The compound according to claim 1,
wherein $R^1$ is selected from the group consisting of CH$_3$, CH$_2$CH$_3$, CH$_2$CH$_2$CH$_3$, CHF$_2$, CF$_3$, and cyclopropyl
or a salt thereof.

3. The compound according to claim 1,
wherein $R^2$ is independently selected from the group consisting of
F, Cl, Br, $C_{1-3}$-alkyl, cyclopropyl, —CN, —$C_{1-3}$-alkylene-OH, —$C_{1-2}$-alkylene-O—$C_{1-2}$-alkyl, NH$_2$, OH, —O—$C_{1-3}$-alkyl, and —S—$C_{1-3}$-alkyl;
wherein the $C_{1-3}$-alkyl group of $R^2$ is optionally substituted with 2 or 3 F, and
wherein the —O—$C_{1-3}$-alkyl group of $R^2$ is optionally substituted with 2 or 3 F;
or a salt thereof.

4. The compound according to claim 1, wherein
$R^3$ is selected from the group consisting of H and $C_{1-3}$-alkyl optionally substituted with 1 to 3 F; and
$R^4$ is selected from the group consisting of $C_{1-6}$-alkyl optionally substituted with 1 to 3 F or
optionally substituted with 1 substituent selected from —CN, —CONH$_2$, —CONH($C_{1-2}$-alkyl), —CON($C_{1-2}$-alkyl)$_2$, —COOH, —COO—$C_{1-2}$-alkyl, $C_{1-2}$-alkyl-CO—NH—, $C_{1-2}$-alkyl-S(=O)$_2$—NH—, OH, and —O—$C_{1-2}$-alkyl optionally substituted with 1 to 3 F;

or $R^4$ is selected from the group consisting of —$C_{0-2}$-alkylene-$C_{3-8}$-cycloalkyl and —$C_{0-2}$-alkylene-$C_{3-9}$-heterocyclyl,
wherein said cycloalkyl moiety of the —$C_{0-2}$-alkylene-$C_{3-8}$-cycloalkyl group of $R^4$ and said heterocyclyl moiety of the —$C_{0-2}$-alkylene-$C_{3-9}$-heterocyclyl group of $R^4$ are saturated mono- or bicyclic ring systems,
wherein said heterocyclyl moiety of the —$C_{0-2}$-alkylene-$C_{3-9}$-heterocyclyl group of $R^4$ contains 1 ring member selected from N, NH, NCO(CH$_3$), NCOO($C_{1-2}$-alkyl), NS(=O)$_2$CH$_3$, N-pyrimidinyl, O, and S(=O)$_2$,
wherein said cycloalkyl moiety of the —$C_{0-2}$-alkylene-$C_{3-8}$-cycloalkyl group of $R^4$ and said heterocyclyl moiety of the —$C_{0-2}$-alkylene-$C_{3-9}$-heterocyclyl group of $R^4$ are optionally substituted with 1 to 2 F and are optionally substituted with 1 to 2 substituents independently selected from —CN, OH, —OCH$_3$, S(=O)$_2$CH$_3$ and $C_{1-3}$-alkyl optionally substituted with 2 to 3 F or with 1 group selected from —CN, OH, and —O—$C_{1-4}$-alkyl;

or $R^4$ is selected from the group consisting of —$C_{0-2}$-alkylene-phenyl and —$C_{0-2}$-alkylene-heteroaryl,
wherein said alkylene moiety of the —$C_{0-2}$-alkylene-phenyl and —$C_{0-2}$-alkylene-heteroaryl groups of $R^4$ is optionally substituted with 1 to 2 CH$_3$, wherein 1 $CH_2$ group of said alkylene moiety of the —$C_{0-2}$-alkylene-phenyl and —$C_{0-2}$-alkylene-heteroaryl groups of $R^4$ is optionally replaced by a

moiety or by a

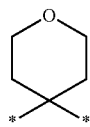

moiety or
wherein 1 —$CH_2$—$CH_2$— group of said alkylene moiety of the —$C_{0-2}$-alkylene-phenyl and —$C_{0-2}$-alkylene-heteroaryl groups of $R^4$ is optionally replaced by a

moiety or by a

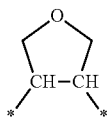

moiety,
wherein said heteroaryl moiety of the —$C_{0-2}$-alkylene-heteroaryl group of $R^4$ is a 5-membered monocycle containing 1 ring member selected from N, NH, O, and S and optionally further containing 1 ring member N, or a 6-membered monocycle containing 1 to 2 ring members N, and
wherein said phenyl moiety of the —$C_{0-2}$-alkylene-phenyl 1 group of $R^4$ and said heteroaryl moiety of the —$C_{0-2}$-alkylene-heteroaryl group of $R^4$ are optionally substituted with 1 to 2 substituents independently selected from
a) F, Cl, Br,
b) —CN,
c) —O—$C_{1-3}$-alkyl optionally substituted with 1 to 3 F, and
d) $C_{1-3}$-alkyl optionally substituted with 1 to 3 F or with 1 substituent selected from —CN and —O—$C_{1-2}$-alkyl;
or
$R^4$ is selected from the group consisting of 8- to 11-membered fused bicyclic aryl, heteroaryl, or heterocyclyl,
wherein said bicyclic aryl, heteroaryl, or heterocyclyl or $R^4$ consists of one non-aromatic ring that is attached to the amide N atom in formula (I) and optionally contains 1 ring member selected from N—, NH, $NCH_3$, $NCO(CH_3)$, $NS(=O)_2CH_3$, and O, and optionally contains 1 ring member selected from C=O and $S(=O)_2$,
and of
one aromatic ring selected from phenyl, pyrrole, furan, and thiophene in each of which 1 CH ring member is optionally replaced with N,
wherein said bicyclic aryl, heteroaryl, or heterocyclyl of $R^4$ is optionally substituted with 1 to 2 F,
is optionally substituted with 1 to 2 $C_{1-2}$-alkyl optionally substituted with 1 to 2 F, and
is optionally substituted with 1 to 2 substituents selected from Cl, —CN, —$CONH_2$, —$CONHCH_3$, —$CON(CH_3)_2$, —COOH, —COO—$C_{1-2}$-alkyl, HO—$C_{1-3}$-alkylene-, $CH_3$—O—$C_{1-3}$-alkylene-, $NH_2$, $CH_3$—CO—NH—, $CH_3$—$S(=O)_2$—NH—, OH, and $CH_3$—O— optionally substituted with 1 to 3 F;
or
$R^3$ and $R^4$ are selected from the group in which $R^3$ and $R^4$, together with the amide N atom they are attached to, form a saturated 4- to 7-membered monocyclic heterocyclyl optionally further containing 1 ring member selected from NH, N($C_{1-4}$-alkyl), N(CO—$C_1$-3-alkyl), N($S(=O)_2$—$C_{1-3}$-alkyl), and O, and optionally containing 1 ring member selected from C=O and $S(=O)_2$,
provided that said saturated 4- to 7-membered monocyclic heterocyclyl formed by $R^3$ and $R^4$ together with the amide N atom they are attached to does not contain any heteroatom-heteroatom bonds other than N—$S(=O)_{r=1,2}$ between ring members,
wherein said saturated 4- to 7-membered monocyclic heterocyclyl formed by $R^3$ and $R^4$ together with the amide N atom they are attached to is optionally substituted with 1 to 2 F,
is optionally substituted with 1 to 2 $C_{1-3}$-alkyl optionally substituted with 2 to 3 F, and
is optionally substituted with 1 substituent selected from Cl, —CN, —$CON(C_{1-3}$-alkyl)$_2$, —COO—$C_{1-3}$-alkyl, $C_{1-3}$-alkyl-O—$C_{1-3}$-alkylene-, and $C_{1-3}$-alkyl-O—;
or
$R^3$ and $R^4$ are selected from the group in which $R^3$ and $R^4$, together with the amide N atom they are attached to, form a saturated 6- to 11-membered bicyclic heterocyclyl optionally further containing 1 ring member selected from N—, NH, N($C_{1-4}$-alkyl), N(CO—$C_{1-3}$-alkyl), N($S(=O)_2$—$C_{1-3}$-alkyl), and O, and
optionally containing 1 ring member selected from C=O and $S(=O)_r$, with r=0, 1, or 2, provided that said saturated 6- to 11-membered bicyclic heterocyclyl formed by $R^3$ and $R^4$ together with the amide N atom they are attached to does not contain any O—S bonds between ring members
wherein said saturated 6- to 11-membered bicyclic heterocyclyl formed by $R^3$ and $R^4$ together with the amide N atom they are attached to is optionally substituted with 1 to 4 F,
is optionally substituted with 1 to 3 $C_{1-3}$-alkyl optionally substituted with 1 to 3 F, or is optionally substituted with 1 to 2 substituents independently selected from Cl, —CN, —$CONH_2$, —$CONH(C_{1-4}$-alkyl), —$CON(C_{1-4}$-alkyl)$_2$, —COOH, —COO—$C_{1-4}$-alkyl, HO—$C_{1-3}$-alkylene-, $C_{1-3}$-alkyl-O—$C_{1-3}$-alkylene-, $C_{1-3}$-alkyl-CO—NH—, $C_{1-3}$-alkyl-$S(=O)_2$—NH—, OH, and $C_{1-3}$-alkyl-O—;
or a salt thereof.

5. The compound according to claim 1, wherein
$R^3$ is selected from the group consisting of H and $C_{1-3}$-alkyl optionally substituted with 1 to 3 F; and
$R^4$ is selected from the group consisting of $C_{1-4}$-alkyl
optionally substituted with 1 to 3 F or
optionally substituted with 1 substituent selected from —CN, —CONH$_2$, —COOH, OH, and —O—$C_{1-2}$-alkyl optionally substituted with 1 to 3 F;
or
$R^4$ is selected from the group consisting of —$C_{0-1}$-alkylene-$C_{3-7}$-cycloalkyl and $C_{3-9}$-heterocyclyl,
wherein said cycloalkyl moiety of the —$C_{0-1}$-alkylene-$C_{3-7}$-cycloalkyl group of $R^4$ and said $C_{3-9}$-heterocyclyl group of $R^4$ are saturated mono- or bicyclic ring systems, wherein said $C_{3-9}$-heterocyclyl group of $R^4$ contains 1 ring member selected from N, NH, NCO(CH$_3$), NCOO($C_{1-2}$-alkyl), NS(=O)$_2$CH$_3$, N-pyrimidinyl, O, and S(=O)$_2$, wherein said cycloalkyl moiety of the —$C_{0-1}$-alkylene-$C_{3-7}$-cycloalkyl group of $R^4$ is optionally substituted with 1 to 2 F or optionally substituted with 1 to 2 CH$_3$ groups or optionally substituted with 1 substituent selected from CH$_2$CH$_3$, —CN, CH$_2$OH, C(CH$_3$)$_2$OH, CHF$_2$, CF$_3$, OH, —OCH$_3$, and S(=O)$_2$CH$_3$,
wherein said $C_{3-9}$-heterocyclyl group of $R^4$ is optionally substituted with 2 F or optionally substituted with 1 to 2 CH$_3$ groups or optionally substituted with 1 substituent selected from CH$_2$CH$_3$ and C(CH$_3$)$_2$H;
or
$R^4$ is selected from the group consisting of —$C_{1-2}$-alkylene-phenyl and —$C_{0-1}$-alkylene-heteroaryl,
wherein 1 CH$_2$ group of said alkylene moiety of the —$C_{1-2}$-alkylene-phenyl and —$C_{0-1}$-alkylene-heteroaryl groups of $R^4$ is optionally replaced by a

moiety or by a

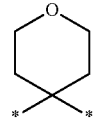

moiety, or
wherein 1 —CH$_2$—CH$_2$— group of said alkylene moiety of the —$C_{1-2}$-alkylene-phenyl and —$C_{0-1}$-alkylene-heteroaryl groups of $R^4$ is optionally replaced by a

moiety or by a

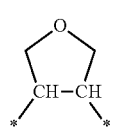

moiety, wherein said heteroaryl moiety of the —$C_{0-1}$-alkylene-heteroaryl group of $R^4$ is a 5-membered monocycle containing 1 ring member N and optionally containing 1 ring member independently selected from N and O, or a 6-membered monocycle containing 1 to 2 ring members N, and
wherein said phenyl moiety of the —$C_{1-2}$-alkylene-phenyl group of $R^4$ and said heteroaryl moiety of the —$C_{0-1}$-alkylene-heteroaryl group of $R^4$ are optionally substituted with 1 to 2 substituents independently selected from F, Cl, OCH$_3$, and CH$_3$;
or
$R^3$ and $R^4$ are selected from the group in which $R^3$ and $R^4$, together with the amide N atom they are attached to, form a saturated 4- to 6-membered monocyclic heterocyclyl optionally further containing 1 ring member O that is non-adjacent to the amide N atom, wherein said saturated 4- to 6-membered monocyclic heterocyclyl formed by $R^3$ and $R^4$ together with the amide N atom they are attached to is optionally substituted with 1 to 2 F or is optionally substituted with 1 to 2 CH$_3$;
or
$R^3$ and $R^4$ are selected from the group in which $R^3$ and $R^4$, together with the amide N atom they are attached to, form a saturated 6- to 11-membered bridged or spiro bicyclic heterocyclyl
optionally further containing 1 ring member selected from N—, NH, N($C_{1-4}$-alkyl), and O that is non-adjacent to the amide N atom,
wherein said saturated 6- to 11-membered bridged or spiro bicyclic heterocyclyl $R^3$ and $R^4$, together with the amide N atom they are attached to is optionally substituted with 1 to 2 F,
is optionally substituted with 1 to 2 $C_{1-3}$-alkyl optionally substituted with 1 to 3 F, or is optionally substituted with 1 substituent selected from Cl, —CN, —CON($C_{1-3}$-alkyl)$_2$, —COO—$C_{1-3}$-alkyl, $C_{1-3}$-alkyl-O—$C_{1-3}$-alkylene-, and $C_{1-3}$-alkyl-O—;
or a salt thereof.

6. The compound according to claim 1, wherein
$R^3$ is selected from the group consisting of H and $C_{1-3}$-alkyl optionally substituted with 1 to 3 F; and
$R^4$ is selected from the group consisting of $C_{1-4}$-alkyl optionally substituted with 1 group selected from F and OCF$_3$;
or
$R^4$ is selected from the group consisting of —$C_{0-1}$-alkylene-$C_{3-7}$-cycloalkyl and $C_{3-9}$-heterocyclyl,
wherein said cycloalkyl moiety of the —$C_{0-1}$-alkylene-$C_{3-7}$-cycloalkyl group of $R^4$ and said $C_{3-9}$-heterocyclyl group of $R^4$ are saturated mono- or bicyclic ring systems, wherein said $C_{3-9}$-heterocyclyl group of $R^4$ contains 1 ring member selected from N, NH, NCO(CH$_3$), NCOO($C_{1-2}$-alkyl), NS(=O)$_2$CH$_3$, N-pyrimidinyl, O, and S(=O)$_2$, wherein said cycloalkyl moiety of the —$C_{0-1}$-alkylene-$C_{3-7}$-cycloalkyl group of $R^4$ is optionally substituted with 1 to 2 F or optionally substituted with 1 to 2 CH$_3$ groups or optionally substituted with 1 substituent selected from CH$_2$CH$_3$, —CN, CH$_2$OH, C(CH$_3$)$_2$OH, CHF$_2$, CF$_3$, OH, —OCH$_3$, and S(=O)$_2$CH$_3$,
wherein said $C_{3-9}$-heterocyclyl group of $R^4$ is optionally substituted with 2 F or optionally substituted with 1 to 2 CH$_3$ groups or optionally substituted with 1 substituent selected from CH$_2$CH$_3$ and C(CH$_3$)$_2$H;

or
R⁴ is selected from the group consisting of —C₁₋₂-alkylene-phenyl and —C₀₋₁-alkylene-heteroaryl,
wherein 1 CH₂ group of said alkylene moiety of the —C₁₋₂-alkylene-phenyl and —C₀₋₁-alkylene-heteroaryl groups of R⁴ is optionally replaced by a

moiety or by a

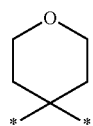

moiety or
wherein 1 —CH₂—CH₂— group of said alkylene moiety of the —C₁₋₂-alkylene-phenyl and —C₀₋₁-alkylene-heteroaryl groups of R⁴ is optionally replaced by a

moiety or by a

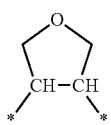

moiety,
wherein said heteroaryl moiety of the —C₀₋₁-alkylene-heteroaryl group of R⁴ is a 5-membered monocycle containing 1 ring member N and optionally containing 1 ring member independently selected from N and O, or a 6-membered monocycle containing 1 to 2 ring members N, and
wherein said phenyl moiety of the —C₁₋₂-alkylene-phenyl group of R⁴ and said heteroaryl moiety of the —C₀₋₁-alkylene-heteroaryl group of R⁴ are optionally substituted with 1 to 2 substituents independently selected from F, Cl, OCH₃, and CH₃;
or
R³ and R⁴ are selected from the group in which R³ and R⁴, together with the amide N atom they are attached to, form a saturated 4- to 6-membered monocyclic heterocyclyl optionally further containing 1 ring member O that is non-adjacent to the amide N atom,
wherein said saturated 4- to 6-membered monocyclic heterocyclyl formed by R³ and R⁴ together with the amide N atom they are attached to is optionally substituted with 1 to 2 F or is optionally substituted with 1 to 2 CH₃;
or
R³ and R⁴ are selected from the group in which R³ and R⁴, together with the amide N atom they are attached to,
form a saturated 6- to 8-membered bridged or spiro bicyclic heterocyclyl optionally containing 1 ring member O that is non-adjacent to the amide N atom;
or a salt thereof.

7. The compound according to claim 1,
wherein
R³ is selected from the group consisting of H, CH₃, CH₂CH₃, and CH₂CH₂CH₃; and
R⁴ is selected from the group consisting of

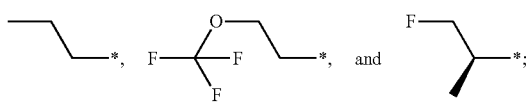

or
R⁴ is selected from the group consisting of

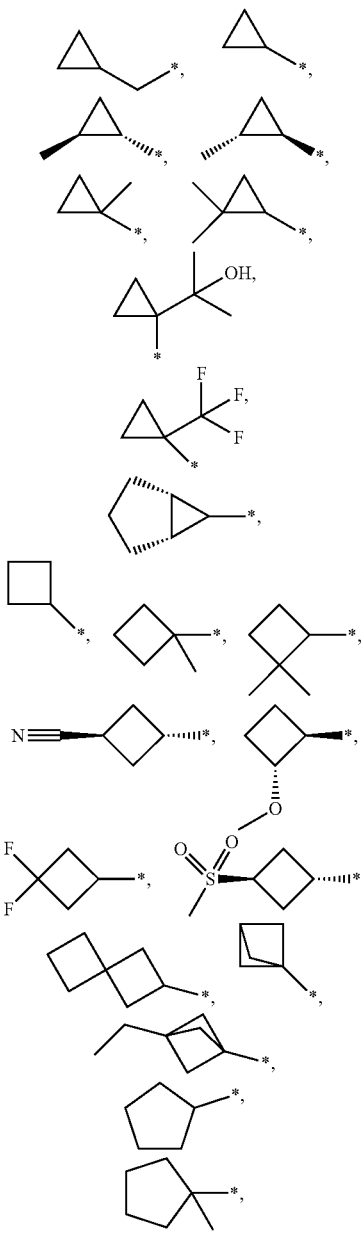

-continued
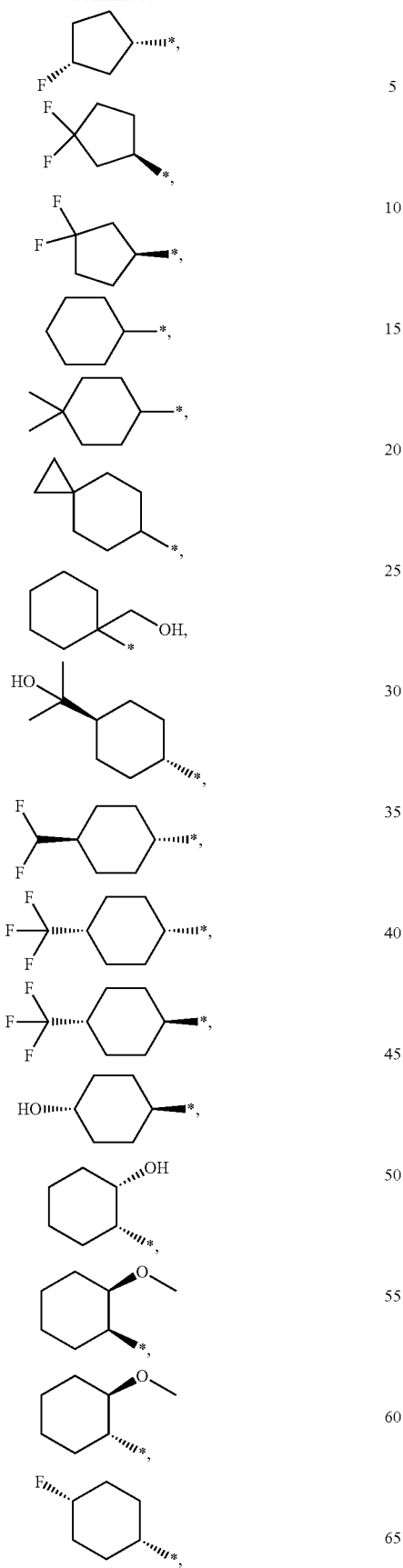
-continued
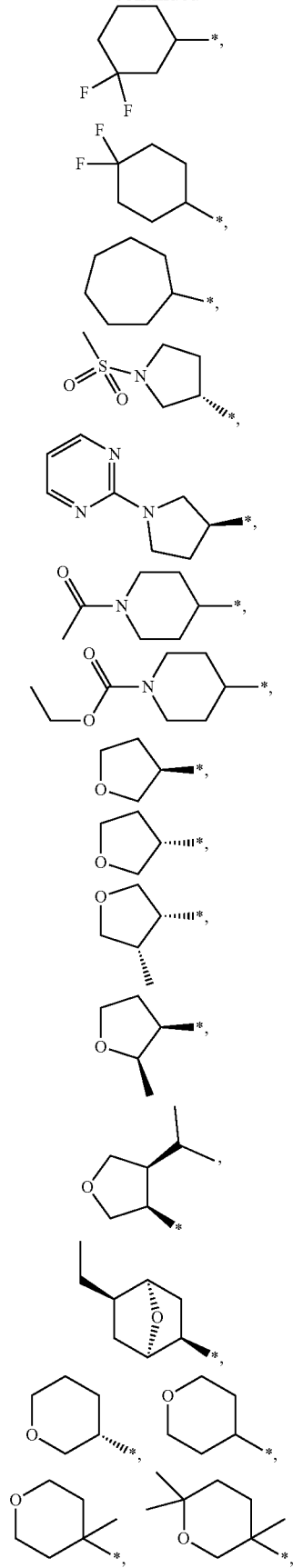

-continued
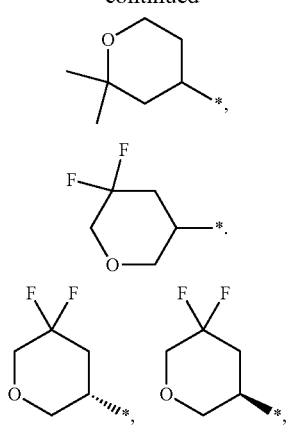
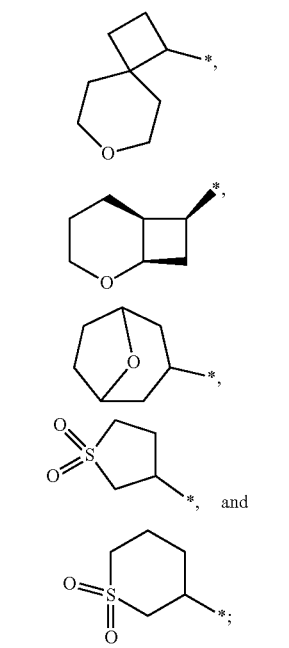
or
R⁴ is selected from the group consisting of
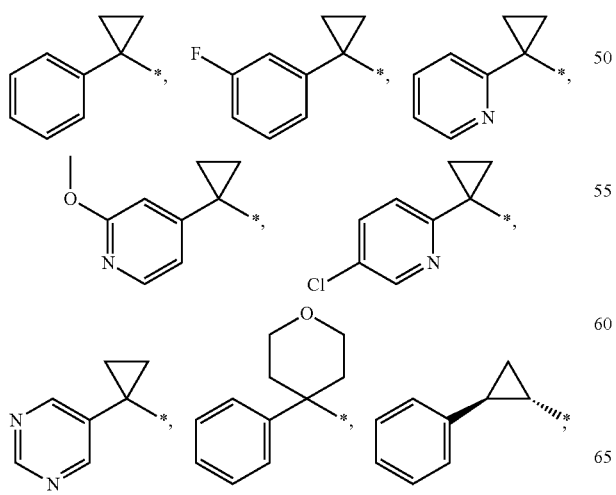
-continued
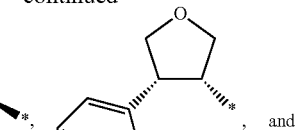, and
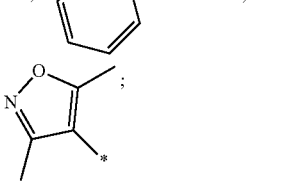;
or
R⁴ is selected from the group consisting of
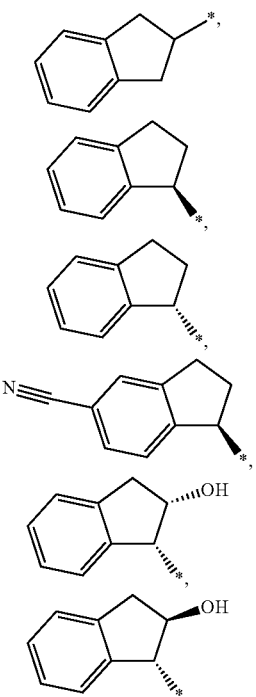
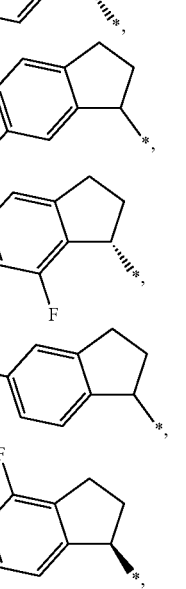

-continued

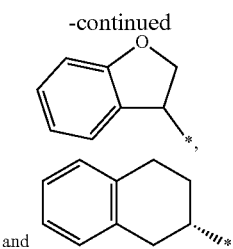
and or
$R^3$ and $R^4$ are selected from the group in which $R^3$ and $R^4$, together with the amide N atom they are attached to, form a heterocyclyl selected from the group consisting of

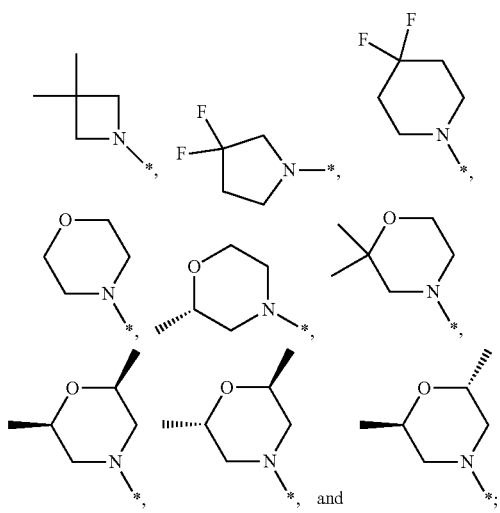

or
$R^3$ and $R^4$ are selected from the group in which $R^3$ and $R^4$, together with the amide N atom they are attached to, form a heterocyclyl selected from the group consisting of

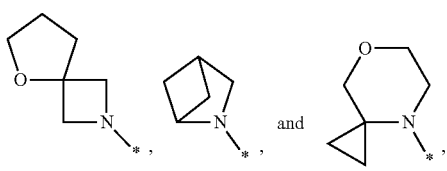

or a salt thereof.

8. The compound according to claim 7, wherein
$R^3$ and $R^4$ are selected from the group in which $R^3$ and $R^4$, together with the amide N atom they are attached to, form a heterocyclyl selected from the group consisting of

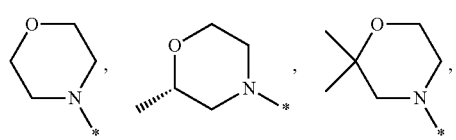

-continued

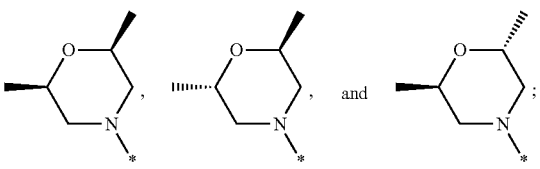

or a salt thereof.

9. The compound according to claim 1, wherein said compound is selected from the group consisting of:

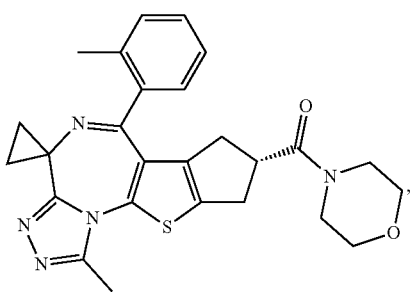

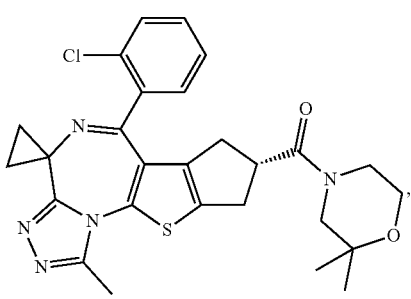

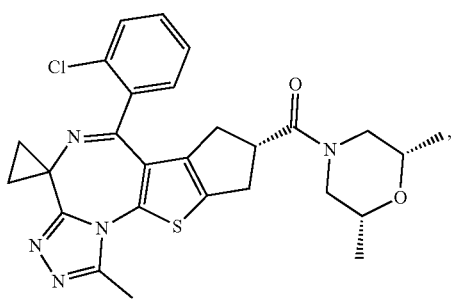

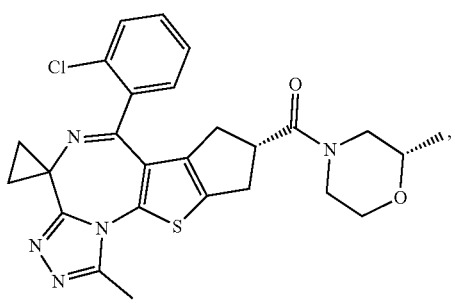

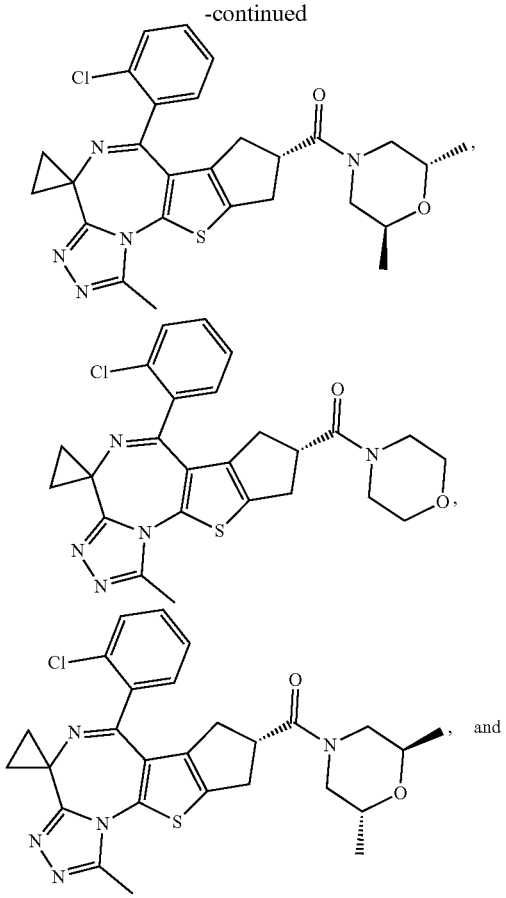

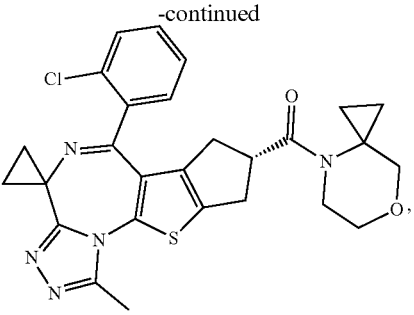

or a salt thereof.

10. A pharmaceutically acceptable salt of the compound according to claim 1.

11. A pharmaceutical composition comprising one or more compounds according to claim 1, or pharmaceutically acceptable salts thereof, optionally together with one or more inert carriers and/or diluents.

12. A pharmaceutical composition comprising one or more compounds according to claim 1, or pharmaceutically acceptable salts thereof, and one or more additional therapeutic agents, optionally together with one or more inert carriers and/or diluents.

13. The pharmaceutical composition according to claim 12, wherein the one or more additional therapeutic agents are selected from the group consisting of antidiabetic agents, agents for the treatment of overweight and/or obesity, agents for the treatment of high blood pressure, heart failure and/or atherosclerosis, agents for the treatment of ocular diseases, and agents for the treatment of allergies and inflammation-related conditions and diseases.

* * * * *